US011013756B2

(12) United States Patent
Haruta et al.

(10) Patent No.: US 11,013,756 B2
(45) Date of Patent: May 25, 2021

(54) ANTI-IL-17 APTAMER HAVING IMPROVED RETENTION IN BLOOD

(71) Applicant: ZENYAKU KOGYO CO., LTD., Tokyo (JP)

(72) Inventors: Kazuhiko Haruta, Tokyo (JP); Hiroaki Yamazaki, Tokyo (JP)

(73) Assignee: ZENYAKU KOGYO CO., LTD., Tokyo (JP)

( * ) Notice: Subject to any disclaimer, the term of this patent is extended or adjusted under 35 U.S.C. 154(b) by 127 days.

(21) Appl. No.: 15/780,464

(22) PCT Filed: Dec. 2, 2016

(86) PCT No.: PCT/JP2016/085948
§ 371 (c)(1),
(2) Date: May 31, 2018

(87) PCT Pub. No.: WO2017/094897
PCT Pub. Date: Jun. 8, 2017

(65) Prior Publication Data
US 2019/0381088 A1  Dec. 19, 2019

(30) Foreign Application Priority Data
Dec. 4, 2015 (JP) .............................. JP2015-237491

(51) Int. Cl.
*C07H 21/04* (2006.01)
*A61K 31/712* (2006.01)
*A61K 47/60* (2017.01)
*C12N 15/115* (2010.01)

(52) U.S. Cl.
CPC ............ *A61K 31/712* (2013.01); *A61K 47/60* (2017.08); *C12N 15/115* (2013.01); *C12N 2310/16* (2013.01); *C12N 2310/315* (2013.01); *C12N 2310/321* (2013.01); *C12N 2310/322* (2013.01); *C12N 2310/3231* (2013.01)

(58) Field of Classification Search
None
See application file for complete search history.

(56) References Cited

U.S. PATENT DOCUMENTS

| 2003/0114647 A1 | 6/2003 | Harris et al. |
| 2004/0253243 A1 | 12/2004 | Epstein et al. |
| 2010/0261245 A1 | 10/2010 | Hahn et al. |
| 2011/0098345 A1 | 4/2011 | Schaub et al. |
| 2016/0046944 A1 | 2/2016 | Ishiguro et al. |

FOREIGN PATENT DOCUMENTS

| JP | 2006-516288 A | 6/2006 |
| JP | 2009-517414 A | 4/2009 |
| JP | 2013-502218 A | 1/2013 |
| WO | 2006/029258 A2 | 3/2006 |
| WO | 2008/048079 A1 | 4/2008 |
| WO | 2014/148638 A1 | 9/2014 |

OTHER PUBLICATIONS

Haruta et al., "A Novel PEGylation Method for Improving the Pharmacokinetic Properties of Anti-Interleukin-17A RNA Aptamers", Nucleic Acid Therapeutics, vol. 27, No. 1, pp. 36-44 (2017).
Hiramoto et al., "Improvements of pharmacokinetic properties of anti-Interleukin-17A aptamer by a novel PEGylation method", the 39th Annual Meeting of the Molecular Biology Society of Japan online Summary, par. 1P-0795, Nov. 16, 2016.
International Search Report for PCT/JP2016/085948, dated Feb. 28, 2017, along with an English language translation.
Written Opinion of the ISA for PCT/JP2016/085948, dated Feb. 28, 2017, along with an English language translation.

*Primary Examiner* — Kimberly Chong
(74) *Attorney, Agent, or Firm* — Greenblum & Bernstein, P.L.C.

(57) ABSTRACT

The present invention provides an anti-IL-17 aptamer comprising a compound represented by the following formula (I):

$$\text{bPEG}_1\text{-}T_1\text{-}X_1\text{-}(Y_1)n_1\text{-}O\text{-}\overset{O^-}{\underset{O}{\overset{|}{P}}}\text{-}O\text{-}(CH_2)L_1$$
$$(CH_2)q\text{-}O\text{-}\overset{O}{\underset{O^-}{\overset{||}{P}}}\text{-}O\text{-}(W)m\text{-}Z$$
$$\text{bPEG}_2\text{-}T_2\text{-}X_2\text{-}(Y_2)n_2\text{-}O\text{-}\overset{O}{\underset{O^-}{\overset{||}{P}}}\text{-}O\text{-}(CH_2)L_2$$

(each symbol is as defined in the DESCRIPTION)
or a pharmaceutically acceptable salt, solvate or hydrate thereof, and showing improved in vivo stability.

13 Claims, 7 Drawing Sheets
Specification includes a Sequence Listing.

FIG. 1

Structure 1. nucleic acid part is Example sequence 1 (Experimental Examples 1, 4 to 7-1, 7-2), Example sequence 2 (Experimental Examples 1, 2, 4, 6), Example sequence 3 (Experimental Examples 3, 4 to 7-1), Example sequence 4 (Experimental Examples 1, 4 to 6, 7-1)

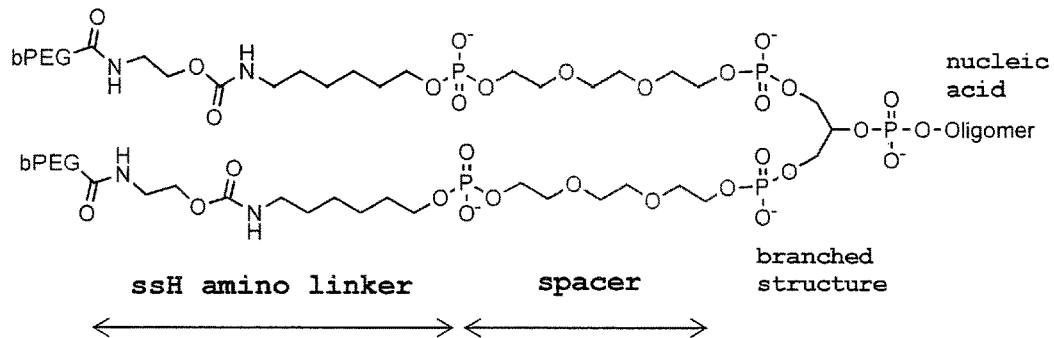

Structure 2. nucleic acid part is Example sequence 2 (Experimental Example 2)

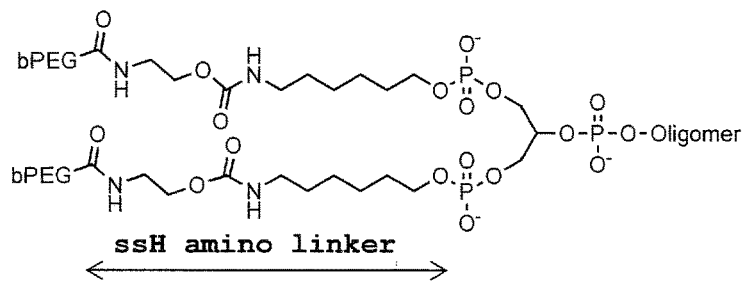

Structure 3: nucleic acid part is Example sequence 2 (Experimental Example 2)

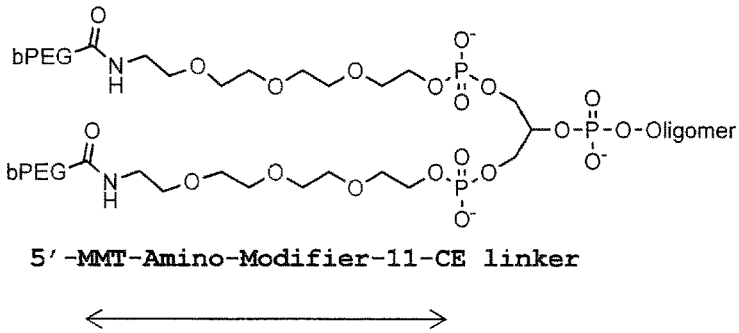

Structure 4: nucleic acid part is Example sequence 1 (Experimental Example 1), Example sequence 2 (Experimental Example 1), Example sequence 3 (Experimental Example 1), Example sequence 4 (Experimental Example 1)

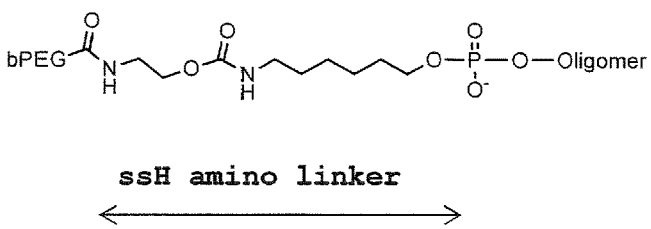

FIG. 2-1

(1) Outline of synthesis procedure

Example nucleic acids 1-4: 3'-terminal nucleotide 150 μmol (synthesis column)

| nucleic acid synthesis by phosphoramidite method (on automatic synthesizer) | ↓ |

5'-nucleic acid sequence-3'

| addition by phosphodiester bond (on automatic synthesizer) | ↓ ← brancher 900 μmol |

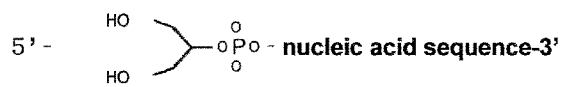

| addition by phosphodiester bond (on automatic synthesizer) | ↓ ← spacer 1350 μmol<br>← linker 1350 μmol |

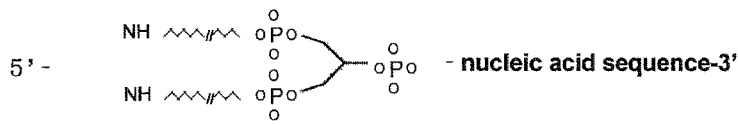

| cleaving out from synthesis column | ↓ deprotection, purification |

5'-aminated oligonucleotide (13.68 μmol)

| PEGylation | ← succinimidyl PEG<br>↓ 0.1M sodium carbonate buffer (pH 9.0) 25°C, 2 hr | purification

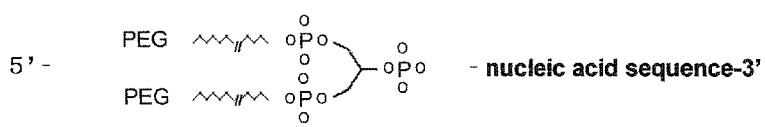

PEGylated oligonucleotide

In Fig., 5'-, 3'- show direction of oligonucleotide (nucleic acid)

$\overset{O}{\underset{O}{\text{oPo}}}$ shows phosphodiester bond (2) confirmation example of final product MALDI-TOF-MS analysis results of PEGylated oligonucleotide of Example sequence 4

SEQUENCE LISTING

<160> NUMBER OF SEQ ID NOS: 114

<210> SEQ ID NO 1
<211> LENGTH: 31
<212> TYPE: RNA
<213> ORGANISM: Artificial Sequence
<220> FEATURE:

<223> OTHER INFORMATION: Aptamer against interleukin-17
<220> FEATURE:
<221> NAME/KEY: misc_feature
<222> LOCATION: (1)..(3)
<223> OTHER INFORMATION: Modification with LNA
<220> FEATURE:
<221> NAME/KEY: misc_feature
<222> LOCATION: (4)..(4)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (9)..(9)
<223> OTHER INFORMATION: Nucleotide is phosphorothioated.
<220> FEATURE:
<221> NAME/KEY: misc_feature
<222> LOCATION: (16)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (23)..(24)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (29)..(31)
<223> OTHER INFORMATION: LNA wherein the base is methylcytosine.

<400> SEQUENCE: 1
ggguagccgg aggagucagu aaucgguacc c                              31

<210> SEQ ID NO 2
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(3)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (4)..(4)
<223> OTHER INFORMATION: When the nucleotide is a ribonucleotide, a

```
        hydroxyl group at the 2'-position of ribose therein is substituted
        by a fluorine atom.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(28)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (16)..(17)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (20)..(20)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (23)..(24)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (27)..(27)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (29)..(31)
<223> OTHER INFORMATION: deoxyribonucleotide

<400> SEQUENCE: 2
ggguagccgg aggagucagu aaucgguacc c                                          31

<210> SEQ ID NO 3
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (7)..(8)
```

<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(27)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: deoxyribonucleotide

<400> SEQUENCE: 3
ggguagccgg aggagucagu aaucgguacc c                                          31

<210> SEQ ID NO 4
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.

```
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(28)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 4
ggguagccgg aggagucagu aaucgguacc c                                    31

<210> SEQ ID NO 5
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(9)
<223> OTHER INFORMATION: ribonucleotide
<220> FEATURE:
<221> NAME/KEY: misc_feature
<222> LOCATION: (1)..(6)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(7)
<223> OTHER INFORMATION: Nucleotide is phosphorothioated.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: deoxyribonucleotide
<220> FEATURE:
<221> NAME/KEY: misc_feature
<222> LOCATION: (11)..(16)
<223> OTHER INFORMATION: ribonucleotide
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (12)..(12)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(20)
<223> OTHER INFORMATION: ribonucleotide
<220> FEATURE:
<221> NAME/KEY: misc_feature
<222> LOCATION: (18)..(19)
<223> OTHER INFORMATION: When the nucleotide is a ribonucleotide, a
      hydroxyl group at the 2'-position of ribose therein is substituted
      by a fluorine atom.
```

```
-continued

<220> FEATURE:
<221> NAME/KEY: misc_feature
<222> LOCATION: (21)..(21)
<223> OTHER INFORMATION: deoxyribonucleotide
<220> FEATURE:
<221> NAME/KEY: misc_feature
<222> LOCATION: (22)..(28)
<223> OTHER INFORMATION: ribonucleotide
<220> FEATURE:
<221> NAME/KEY: misc_feature
<222> LOCATION: (22)..(27)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (29)..(33)
<223> OTHER INFORMATION: deoxyribonucleotide

<400> SEQUENCE: 5
gggguagccg gaggagtcag taaucgguac ccc                                 33

<210> SEQ ID NO 6
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
```

```
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(27)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: deoxyribonucleotide

<400> SEQUENCE: 6
ggguagccgg aggagtcagt aaucgguacc c                                    31

<210> SEQ ID NO 7
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
```

```
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(28)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 7
ggguagccgg aggagucagu aaucgguacc c                                    31

<210> SEQ ID NO 8
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
```

```
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
```

```
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 8
ggguagccgg aggagtcagt aaucgguacc c                                         31

<210> SEQ ID NO 9
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 9
ggguagccgg aggagtcagt aaucgguacc c                                        31

<210> SEQ ID NO 10
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
```

-continued

```
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(27)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: deoxyribonucleotide
```

<400> SEQUENCE: 10
ggguagccgg aggagtcagt aaucgguacc c        31

<210> SEQ ID NO 11
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.

```
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 11
ggguagccgg aggagtcagt aaucgguacc c                                31

<210> SEQ ID NO 12
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
```

```
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 12
ggguagccgg aggagtcagt aaucgguacc c                                      31

<210> SEQ ID NO 13
<211> LENGTH: 31
```

```
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 13
ggguagccgg aggagtcagt aaucgguacc c                                     31

<210> SEQ ID NO 14
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
```

<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 14
ggguagccgg aggagtcagt aaucgguacc c                          31

<210> SEQ ID NO 15
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:

```
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
```

-continued

```
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 15
ggguagccgg aggagtcagt aaucgguacc c                                     31

<210> SEQ ID NO 16
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(5)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(9)
<223> OTHER INFORMATION: ribonucleotide
<220> FEATURE:
<221> NAME/KEY: misc_feature
<222> LOCATION: (7)..(7)
<223> OTHER INFORMATION: Nucleotide is phosphorothioated.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: deoxyribonucleotide
<220> FEATURE:
```

<220> FEATURE:
<221> NAME/KEY: misc_feature
<222> LOCATION: (11)..(16)
<223> OTHER INFORMATION: ribonucleotide
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (12)..(12)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(20)
<223> OTHER INFORMATION: ribonucleotide
<220> FEATURE:
<221> NAME/KEY: misc_feature
<222> LOCATION: (18)..(19)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(21)
<223> OTHER INFORMATION: deoxyribonucleotide
<220> FEATURE:
<221> NAME/KEY: misc_feature
<222> LOCATION: (22)..(29)
<223> OTHER INFORMATION: ribonucleotide
<220> FEATURE:
<221> NAME/KEY: misc_feature
<222> LOCATION: (22)..(27)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (29)..(29)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (30)..(33)
<223> OTHER INFORMATION: deoxyribonucleotide

<400> SEQUENCE: 16
gggguagccg gaggagtcag taaucgguac ccc                                33

<210> SEQ ID NO 17
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature

```
<222> LOCATION: (1)..(5)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(9)
<223> OTHER INFORMATION: ribonucleotide
<220> FEATURE:
<221> NAME/KEY: misc_feature
<222> LOCATION: (7)..(7)
<223> OTHER INFORMATION: Nucleotide is phosphorothioated.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: deoxyribonucleotide
<220> FEATURE:
<221> NAME/KEY: misc_feature
<222> LOCATION: (11)..(16)
<223> OTHER INFORMATION: ribonucleotide
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (12)..(12)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(20)
<223> OTHER INFORMATION: ribonucleotide
<220> FEATURE:
<221> NAME/KEY: misc_feature
<222> LOCATION: (18)..(19)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(21)
<223> OTHER INFORMATION: deoxyribonucleotide
<220> FEATURE:
<221> NAME/KEY: misc_feature
<222> LOCATION: (22)..(22)
<223> OTHER INFORMATION: ribonucleotide
<220> FEATURE:
<221> NAME/KEY: misc_feature
<222> LOCATION: (22)..(22)
<223> OTHER INFORMATION: When the nucleotide is a ribonucleotide, a
      hydroxyl group at the 2'-position of ribose therein is substituted
```

```
      by an O-methyl group.
<220> FEATURE:
<221> NAME/KEY: misc_feature
<222> LOCATION: (23)..(23)
<223> OTHER INFORMATION: deoxyribonucleotide
<220> FEATURE:
<221> NAME/KEY: misc_feature
<222> LOCATION: (24)..(29)
<223> OTHER INFORMATION: ribonucleotide
<220> FEATURE:
<221> NAME/KEY: misc_feature
<222> LOCATION: (24)..(27)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (29)..(29)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (30)..(33)
<223> OTHER INFORMATION: deoxyribonucleotide

<400> SEQUENCE: 17
gggguagccg gaggagtcag taaucgguac ccc                                33

<210> SEQ ID NO 18
<211> LENGTH: 33
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(5)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(9)
<223> OTHER INFORMATION: ribonucleotide
<220> FEATURE:
<221> NAME/KEY: misc_feature
<222> LOCATION: (7)..(7)
<223> OTHER INFORMATION: Nucleotide is phosphorothioated.
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: deoxyribonucleotide
<220> FEATURE:
<221> NAME/KEY: misc_feature
<222> LOCATION: (11)..(16)
<223> OTHER INFORMATION: ribonucleotide
```

```
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (12)..(12)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(20)
<223> OTHER INFORMATION: ribonucleotide
<220> FEATURE:
<221> NAME/KEY: misc_feature
<222> LOCATION: (18)..(19)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(21)
<223> OTHER INFORMATION: deoxyribonucleotide
<220> FEATURE:
<221> NAME/KEY: misc_feature
<222> LOCATION: (22)..(29)
<223> OTHER INFORMATION: ribonucleotide
<220> FEATURE:
<221> NAME/KEY: misc_feature
<222> LOCATION: (24)..(27)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (29)..(29)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (30)..(33)
<223> OTHER INFORMATION: deoxyribonucleotide

<400> SEQUENCE: 18
gggguagccg gaggagtcag taaucgguac ccc                                  33

<210> SEQ ID NO 19
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
```

```
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
```

```
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 19
ggguagccgg aggagtcagt aaucgguacc c                                   31

<210> SEQ ID NO 20
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
```

```
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 20
ggguagccgg aggagtcagt aaucgguacc c                                    31

<210> SEQ ID NO 21
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
```

-continued

```
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
```

<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 21
ggguagccgg aggagtcagt aaucggtacc c                                        31

<210> SEQ ID NO 22
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 22
ggguagccgg aggagtcagt aaucggtacc c                                      31

<210> SEQ ID NO 23
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)

<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 23
ggguagccgg aggagtcagt aaucggtacc c                                    31

<210> SEQ ID NO 24
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide

```
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 24
ggguagccgg aggagtcagt aaucggtacc c                                    31

<210> SEQ ID NO 25
<211> LENGTH: 31
<212> TYPE: DNA
<213> ORGANISM: Artificial Sequence
<220> FEATURE:
```

```
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
```

<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 25
ggguagccgg aggagtcagt aaucggtacc c                                    31

<210> SEQ ID NO 26
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)

```
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 26
ggguagccgg aggagtcagt aaucggtacc c                             31

<210> SEQ ID NO 27
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
```

```
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
```

-continued

```
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 27
ggguagccgg aggagtcagt aaucggtacc c                                      31

<210> SEQ ID NO 28
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
```

```
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 28
ggguagccgg aggagtcagt aaucggtacc c                                    31

<210> SEQ ID NO 29
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 29
ggguagccgg aggagtcagt aaucggtacc c                              31
```

```
<210> SEQ ID NO 30
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
```

```
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 30
ggguagccgg aggagtcagt aaucggtacc c                                  31

<210> SEQ ID NO 31
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
```

```
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 31
ggguagccgg aggagtcagt aaucggtacc c                          31

<210> SEQ ID NO 32
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
```

```
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(31)
<223> OTHER INFORMATION: deoxyribonucleotide

<400> SEQUENCE: 32
ggguagccgg aggagtcagt aaucggtacc c                                    31
```

```
<210> SEQ ID NO 33
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(10)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
``` by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(31)
<223> OTHER INFORMATION: deoxyribonucleotide

<400> SEQUENCE: 33
ggguagccgg aggagtcagt aaucggtacc c                                      31

<210> SEQ ID NO 34
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature

```
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 34
ggguagccgg aggagtcagt aaucggtacc c                                   31

<210> SEQ ID NO 35
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
```

```
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
```

```
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 35
ggguagccgg aggagtcagt aaucggtacc c                                    31

<210> SEQ ID NO 36
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(6)
<223> OTHER INFORMATION: deoxyribonucleotide
<220> FEATURE:
<221> NAME/KEY: misc_feature
<222> LOCATION: (7)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
```

```
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 36
ggguagccgg aggagtcagt aaucggtacc c                                31

<210> SEQ ID NO 37
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
```

```
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
```

<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 37
ggguagccgg aggagtcagt aaucggtacc c                                      31

<210> SEQ ID NO 38
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide

```
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 38
ggguagccgg aggagtcagt aaucggtacc c                              31

<210> SEQ ID NO 39
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
```

```
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (22)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
```

```
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 39
ggguagccgg aggagtcagt aaucggtacc c                                    31

<210> SEQ ID NO 40
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
```

```
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 40
ggguagccgg aggagtcagt aaucggtacc c                              31

<210> SEQ ID NO 41
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
```

<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 41
ggguagccgg aggagtcagt aaucggtacc c                                    31

<210> SEQ ID NO 42
<211> LENGTH: 31
<212> TYPE: DNA

-continued

```
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (22)..(22)
<223> OTHER INFORMATION: deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
```

```
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 42
ggguagccgg aggagtcagt aaucggtacc c                                     31

<210> SEQ ID NO 43
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
```

```
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 43
ggguagccgg aggagtcagt aaucggtacc c                                    31

<210> SEQ ID NO 44
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
```

-continued

```
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(26)
<223> OTHER INFORMATION: ribonucleotide
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide
<220> FEATURE:
<221> NAME/KEY: misc_feature
<222> LOCATION: (28)..(31)
<223> OTHER INFORMATION: ribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 44
```
ggguagccgg aggagtcagt aaucggtacc c                31

<210> SEQ ID NO 45
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide -continued

```
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 45
ggguagccgg aggagtcagt aaucgguacc c                                   31

<210> SEQ ID NO 46
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
```

```
<223> OTHER INFORMATION: deoxyribonucleotide
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 46
ggguagccgg aggagtcagt aaucgguacc c                                 31

<210> SEQ ID NO 47
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

```
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
```

<221> NAME/KEY: misc_feature
<222> LOCATION: (29)..(31)
<223> OTHER INFORMATION: deoxyribonucleotide

<400> SEQUENCE: 47
ggguagccgg aggagtcagt aaucgguacc c                                31

<210> SEQ ID NO 48
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature

```
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 48
ggguagccgg aggagtcagt aaucgguacc c                                 31

<210> SEQ ID NO 49
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: deoxyribonucleotide
<220> FEATURE:
```

```
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 49
ggguagccgg aggagtcagt aaucgguacc c                                31

<210> SEQ ID NO 50
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
```

```
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
```

```
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 50
ggguagccgg aggagtcagt aaucgguacc c                                       31

<210> SEQ ID NO 51
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
```

```
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 51
ggguagccgg aggagtcagt aaucgguacc c                              31

<210> SEQ ID NO 52
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
```

```
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 52
ggguagccgg aggagucagu aaucgguacc c                                31
```

```
<210> SEQ ID NO 53
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
```

```
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 53
ggguagccgg aggagtcagt gaucgguacc c                                        31

<210> SEQ ID NO 54
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
``` hydroxyl group at the 2'-position of ribose therein is substituted
        by an O-methyl group.
<220> FEATURE:
<221> NAME/KEY: misc_feature
<222> LOCATION: (11)..(11)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (13)..(14)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (27)..(27)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (28)..(28)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 54
ggguagccgg aggagtcagt aaucgguacc c                                    31

<210> SEQ ID NO 55
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:

```
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

```
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 55
ggguagccgg aggagtcagt aaucgguacc c                                31

<210> SEQ ID NO 56
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (12)..(12)
<223> OTHER INFORMATION: Nucleotide is phosphorothioated.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 56
ggguagccgg aggagtcagt aaucgguacc c                                    31
```

```
<210> SEQ ID NO 57
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
```

-continued

```
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 57
ggguagccgg aggagtcagt aaucgguacc c                                      31

<210> SEQ ID NO 58
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

-continued

```
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 58
ggguagccgg aggagtcagt aaucgguacc c                                        31

<210> SEQ ID NO 59
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
```

<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (29)..(31)
<223> OTHER INFORMATION: deoxyribonucleotide

<400> SEQUENCE: 59
ggguagccgg aggagtcagt aaucgguacc c                                    31

<210> SEQ ID NO 60
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:

<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a hydroxyl group at the 2'-position of ribose therein is substituted by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a hydroxyl group at the 2'-position of ribose therein is substituted by an O-methyl group.
<220> FEATURE:
<221> NAME/KEY: misc_feature
<222> LOCATION: (27)..(27)
<223> OTHER INFORMATION: When the nucleotide is a ribonucleotide, a hydroxyl group at the 2'-position of ribose therein is substituted by a fluorine atom.
<220> FEATURE:
<221> NAME/KEY: misc_feature
<222> LOCATION: (28)..(31)
<223> OTHER INFORMATION: When the nucleotide is a ribonucleotide, a hydroxyl group at the 2'-position of ribose therein is substituted by an O-methyl group.

<400> SEQUENCE: 60
ggguagccgg aggagtcagt aaucgguacc c                             31

<210> SEQ ID NO 61
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a hydroxyl group at the 2'-position of ribose therein is substituted by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a hydroxyl group at the 2'-position of ribose therein is substituted by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 61
ggguagccgg aggagtcagt aaucgguacc c                          31

<210> SEQ ID NO 62
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:

```
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
```

-continued

<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 62
ggguagccgg aggagtcagt aaucgguacc c                                  31

<210> SEQ ID NO 63
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:

```
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 63
ggguagccgg aggagtcagt aaucgguacc c                                        31

<210> SEQ ID NO 64
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
```

```
       hydroxyl group at the 2'-position of ribose therein is substituted
       by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
       hydroxyl group at the 2'-position of ribose therein is substituted
       by an O-methyl group.

<400> SEQUENCE: 64
ggguagccgg aggagtcagt aaucgguacc c                                31

<210> SEQ ID NO 65
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
```

```
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 65
ggguagccgg aggagtcagt aaucgguacc c                                    31

<210> SEQ ID NO 66
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
```

```
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(27)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
```

<221> NAME/KEY: misc_feature
<222> LOCATION: (29)..(31)
<223> OTHER INFORMATION: When the nucleotide is a ribonucleotide, a
hydroxyl group at the 2'-position of ribose therein is substituted
by an O-methyl group.

<400> SEQUENCE: 66
ggguagccgg aggagucagu aaucgguacc c                          31

<210> SEQ ID NO 67
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
hydroxyl group at the 2'-position of ribose therein is substituted
by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
hydroxyl group at the 2'-position of ribose therein is substituted
by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
hydroxyl group at the 2'-position of ribose therein is substituted
by an O-methyl group.
<220> FEATURE:
<221> NAME/KEY: misc_feature
<222> LOCATION: (11)..(11)
<223> OTHER INFORMATION: When the nucleotide is a ribonucleotide, a
hydroxyl group at the 2'-position of ribose therein is substituted
by a fluorine atom.
<220> FEATURE:
<221> NAME/KEY: misc_feature
<222> LOCATION: (13)..(14)
<223> OTHER INFORMATION: When the nucleotide is a ribonucleotide, a
hydroxyl group at the 2'-position of ribose therein is substituted
by an O-methyl group.
<220> FEATURE:
<221> NAME/KEY: misc_feature
<222> LOCATION: (16)..(18)
<223> OTHER INFORMATION: When the nucleotide is a ribonucleotide, a
hydroxyl group at the 2'-position of ribose therein is substituted
by a fluorine atom.
<220> FEATURE:
<221> NAME/KEY: misc_feature
<222> LOCATION: (20)..(20)
<223> OTHER INFORMATION: When the nucleotide is a ribonucleotide, a
hydroxyl group at the 2'-position of ribose therein is substituted
by a fluorine atom.
<220> FEATURE:
<221> NAME/KEY: misc_feature
<222> LOCATION: (21)..(26)
<223> OTHER INFORMATION: When the nucleotide is a ribonucleotide, a hydroxyl group at the 2'-position of ribose therein is substituted
        by an O-methyl group.
<220> FEATURE:
<221> NAME/KEY: misc_feature
<222> LOCATION: (27)..(27)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (28)..(31)
<223> OTHER INFORMATION: When the nucleotide is a ribonucleotide, a
        hydroxyl group at the 2'-position of ribose therein is substituted
        by an O-methyl group.

<400> SEQUENCE: 67
ggguagccgg aggagucagu aaucgguacc c                                    31

<210> SEQ ID NO 68
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (11)..(11)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (13)..(14)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)

```
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 68
ggguagccgg aggagucagu aaucgguacc c                               31

<210> SEQ ID NO 69
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

-continued

```
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 69
ggguagccgg aggagucagu aaucgguacc c                                    31

<210> SEQ ID NO 70
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 70
ggguagccgg aggagucagu aaucgguacc c                                    31

<210> SEQ ID NO 71
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
```

```
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 71
ggguagccgg aggagucagu aaucgguacc c                                     31

<210> SEQ ID NO 72
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
```

-continued

```
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 72
```
ggguagccgg aggagtcagt aaucgguacc c                                    31

<210> SEQ ID NO 73
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(15)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:

```
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 73
ggguagccgg aggagtcagt aaucgguacc c                                      31

<210> SEQ ID NO 74
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(27)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

<222> LOCATION: (27)..(27)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (28)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
       hydroxyl group at the 2'-position of ribose therein is substituted
       by an O-methyl group.

<400> SEQUENCE: 74
ggguagccgg aggagucagu aaucgguacc c                                      31

<210> SEQ ID NO 75
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(27)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (7)..(8)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (10)..(10)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (11)..(11)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (13)..(14)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (16)..(18)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (20)..(20)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (21)..(26)

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 75
ggguagccgg aggagucagu aaucgguacc c                                      31

<210> SEQ ID NO 76
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

```
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 76
ggguagccgg aggagtcagt aaucgguacc c                                      31

<210> SEQ ID NO 77
<211> LENGTH: 31
<212> TYPE: RNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
```

```
                  by a fluorine atom.
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 77
ggguagccgg aggagucagu aaucgguacc c                                          31

<210> SEQ ID NO 78
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(27)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
```

```
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(28)
<223> OTHER INFORMATION: deoxyribonucleotide
<220> FEATURE:
<221> NAME/KEY: misc_feature
<222> LOCATION: (29)..(31)
<223> OTHER INFORMATION: ribonucleotide
<220> FEATURE:
<221> NAME/KEY: misc_feature
<222> LOCATION: (29)..(31)
<223> OTHER INFORMATION: When the nucleotide is a ribonucleotide, a
      hydroxyl group at the 2'-position of ribose therein is substituted
      by an O-methyl group.

<400> SEQUENCE: 78
ggguagccgg aggagucagu aaucgguacc c                                31

<210> SEQ ID NO 79
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
```

<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 79
ggguagccgg aggagtcagt aaucgguacc c                                     31

<210> SEQ ID NO 80
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide

```
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 80
ggguagccgg aggagtcagt aaucgguacc c                                   31

<210> SEQ ID NO 81
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
```

-continued by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 81
ggguagccgg aggagucagu aaucgguacc c          31

<210> SEQ ID NO 82
<211> LENGTH: 31

```
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 82
ggguagccgg aggagucagu aaucgguacc c                                31

<210> SEQ ID NO 83
<211> LENGTH: 31
<212> TYPE: DNA
```

-continued

```
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
``` hydroxyl group at the 2'-position of ribose therein is substituted by an O-methyl group.

<400> SEQUENCE: 83
ggguagccgg aggagucagu aaucgguacc c          31

<210> SEQ ID NO 84
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:

<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (21)..(31)
<223> OTHER INFORMATION: When the nucleotide is a ribonucleotide, a
      hydroxyl group at the 2'-position of ribose therein is substituted
      by an O-methyl group.

<400> SEQUENCE: 84
ggguagccgg aggagtcagt gaucgguacc c                                  31

<210> SEQ ID NO 85
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature

```
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (22)..(31)
<223> OTHER INFORMATION: When the nucleotide is a ribonucleotide, a
      hydroxyl group at the 2'-position of ribose therein is substituted
      by an O-methyl group.

<400> SEQUENCE: 85
ggguagccgg aggagtcagt gaucgguacc c                                 31

<210> SEQ ID NO 86
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
```

<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (22)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 86
ggguagccgg aggagucagu gaucgguacc c                                      31

<210> SEQ ID NO 87
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature

```
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (22)..(31)
<223> OTHER INFORMATION: When the nucleotide is a ribonucleotide, a
      hydroxyl group at the 2'-position of ribose therein is substituted
      by an O-methyl group.

<400> SEQUENCE: 87
ggguagccgg aggagtcagt aaucgguacc c                                    31

<210> SEQ ID NO 88
<211> LENGTH: 31
<212> TYPE: DNA
```

```
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
```

-continued

```
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (23)..(31)
<223> OTHER INFORMATION: When the nucleotide is a ribonucleotide, a
      hydroxyl group at the 2'-position of ribose therein is substituted
      by an O-methyl group.

<400> SEQUENCE: 88
ggguagccgg aggagtcagt aaucgguacc c                                  31

<210> SEQ ID NO 89
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (23)..(31)
<223> OTHER INFORMATION: When the nucleotide is a ribonucleotide, a
      hydroxyl group at the 2'-position of ribose therein is substituted
      by an O-methyl group.

<400> SEQUENCE: 89
ggguagccgg aggagtcagt aaucgguacc c                                 31

<210> SEQ ID NO 90
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
```

```
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (22)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 90
ggguagccgg aggagucagu aaucgguacc c                                  31

<210> SEQ ID NO 91
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
```

```
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(21)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 91
ggguagccgg aggagucagu aaucgguacc c                                    31

<210> SEQ ID NO 92
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

```
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(31)
<223> OTHER INFORMATION: ribonucleotide
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is phosphorothioated.
<220> FEATURE:
<221> NAME/KEY: misc_feature
<222> LOCATION: (16)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is phosphorothioated.
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 92
ggguagccgg aggagucagu aaucgguacc c                                    31

<210> SEQ ID NO 93
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
```

-continued

```
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: deoxyribonucleotide
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: deoxyribonucleotide
<220> FEATURE:
<221> NAME/KEY: misc_feature
<222> LOCATION: (21)..(31)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
``` hydroxyl group at the 2'-position of ribose therein is substituted
        by an O-methyl group.
<220> FEATURE:
<221> NAME/KEY: misc_feature
<222> LOCATION: (27)..(27)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (28)..(31)
<223> OTHER INFORMATION: When the nucleotide is a ribonucleotide, a
        hydroxyl group at the 2'-position of ribose therein is substituted
        by an O-methyl group.

<400> SEQUENCE: 93
ggguagccgg aggagtcagt aaucgguacc c                                              31

<210> SEQ ID NO 94
<211> LENGTH: 29
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(3)
<223> OTHER INFORMATION: ribonucleotide
<220> FEATURE:
<221> NAME/KEY: misc_feature
<222> LOCATION: (1)..(3)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (4)..(4)
<223> OTHER INFORMATION: deoxyribonucleotide
<220> FEATURE:
<221> NAME/KEY: misc_feature
<222> LOCATION: (5)..(7)
<223> OTHER INFORMATION: ribonucleotide
<220> FEATURE:
<221> NAME/KEY: misc_feature
<222> LOCATION: (5)..(5)
<223> OTHER INFORMATION: Nucleotide is phosphorothioated.
<220> FEATURE:
<221> NAME/KEY: misc_feature
<222> LOCATION: (6)..(7)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (8)..(8)
<223> OTHER INFORMATION: deoxyribonucleotide
<220> FEATURE:
<221> NAME/KEY: misc_feature
<222> LOCATION: (9)..(14)
<223> OTHER INFORMATION: ribonucleotide
<220> FEATURE:
<221> NAME/KEY: misc_feature
<222> LOCATION: (9)..(9)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (10)..(10)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (12)..(13)
<223> OTHER INFORMATION: When the nucleotide is a ribonucleotide, a
        hydroxyl group at the 2'-position of ribose therein is substituted

```
      by an O-methyl group.
<220> FEATURE:
<221> NAME/KEY: misc_feature
<222> LOCATION: (15)..(15)
<223> OTHER INFORMATION: deoxyribonucleotide
<220> FEATURE:
<221> NAME/KEY: misc_feature
<222> LOCATION: (16)..(18)
<223> OTHER INFORMATION: ribonucleotide
<220> FEATURE:
<221> NAME/KEY: misc_feature
<222> LOCATION: (16)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: deoxyribonucleotide
<220> FEATURE:
<221> NAME/KEY: misc_feature
<222> LOCATION: (20)..(27)
<223> OTHER INFORMATION: ribonucleotide
<220> FEATURE:
<221> NAME/KEY: misc_feature
<222> LOCATION: (22)..(25)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (26)..(26)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (28)..(29)
<223> OTHER INFORMATION: deoxyribonucleotide

<400> SEQUENCE: 94
gguagccgga ggagtcagta aucgguacc                                        29

<210> SEQ ID NO 95
<211> LENGTH: 27
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(2)
<223> OTHER INFORMATION: ribonucleotide
<220> FEATURE:
<221> NAME/KEY: misc_feature
<222> LOCATION: (1)..(2)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (3)..(3)
<223> OTHER INFORMATION: deoxyribonucleotide
<220> FEATURE:
<221> NAME/KEY: misc_feature
<222> LOCATION: (4)..(6)
<223> OTHER INFORMATION: ribonucleotide
<220> FEATURE:
<221> NAME/KEY: misc_feature
<222> LOCATION: (4)..(4)
<223> OTHER INFORMATION: Nucleotide is phosphorothioated.
```

-continued

```
<220> FEATURE:
<221> NAME/KEY: misc_feature
<222> LOCATION: (5)..(6)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(7)
<223> OTHER INFORMATION: deoxyribonucleotide
<220> FEATURE:
<221> NAME/KEY: misc_feature
<222> LOCATION: (8)..(13)
<223> OTHER INFORMATION: ribonucleotide
<220> FEATURE:
<221> NAME/KEY: misc_feature
<222> LOCATION: (8)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (11)..(12)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (14)..(14)
<223> OTHER INFORMATION: deoxyribonucleotide
<220> FEATURE:
<221> NAME/KEY: misc_feature
<222> LOCATION: (15)..(17)
<223> OTHER INFORMATION: ribonucleotide
<220> FEATURE:
<221> NAME/KEY: misc_feature
<222> LOCATION: (15)..(16)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(26)
<223> OTHER INFORMATION: ribonucleotide
<220> FEATURE:
<221> NAME/KEY: misc_feature
<222> LOCATION: (21)..(24)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (25)..(25)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (26)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: deoxyribonucleotide

<400> SEQUENCE: 95
```
guagccggag gagtcagtaa ucgguac							27

<210> SEQ ID NO 96
<211> LENGTH: 25
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(1)
<223> OTHER INFORMATION: ribonucleotide
<220> FEATURE:
<221> NAME/KEY: misc_feature
<222> LOCATION: (1)..(1)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (2)..(2)
<223> OTHER INFORMATION: deoxyribonucleotide
<220> FEATURE:
<221> NAME/KEY: misc_feature
<222> LOCATION: (3)..(5)
<223> OTHER INFORMATION: ribonucleotide
<220> FEATURE:
<221> NAME/KEY: misc_feature
<222> LOCATION: (3)..(3)
<223> OTHER INFORMATION: Nucleotide is phosphorothioated.
<220> FEATURE:
<221> NAME/KEY: misc_feature
<222> LOCATION: (4)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(12)
<223> OTHER INFORMATION: ribonucleotide
<220> FEATURE:
<221> NAME/KEY: misc_feature
<222> LOCATION: (7)..(7)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (8)..(8)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(13)
<223> OTHER INFORMATION: deoxyribonucleotide
<220> FEATURE:
<221> NAME/KEY: misc_feature
<222> LOCATION: (14)..(16)
<223> OTHER INFORMATION: ribonucleotide
<220> FEATURE:
<221> NAME/KEY: misc_feature
<222> LOCATION: (14)..(15)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature

```
<222> LOCATION: (17)..(17)
<223> OTHER INFORMATION: deoxyribonucleotide
<220> FEATURE:
<221> NAME/KEY: misc_feature
<222> LOCATION: (18)..(25)
<223> OTHER INFORMATION: ribonucleotide
<220> FEATURE:
<221> NAME/KEY: misc_feature
<222> LOCATION: (20)..(23)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (24)..(24)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (25)..(25)
<223> OTHER INFORMATION: When the nucleotide is a ribonucleotide, a
      hydroxyl group at the 2'-position of ribose therein is substituted
      by an O-methyl group.

<400> SEQUENCE: 96
uagccggagg agtcagtaau cggua                                          25

<210> SEQ ID NO 97
<211> LENGTH: 29
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(3)
<223> OTHER INFORMATION: ribonucleotide
<220> FEATURE:
<221> NAME/KEY: misc_feature
<222> LOCATION: (1)..(3)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (4)..(4)
<223> OTHER INFORMATION: deoxyribonucleotide
<220> FEATURE:
<221> NAME/KEY: misc_feature
<222> LOCATION: (5)..(7)
<223> OTHER INFORMATION: ribonucleotide
<220> FEATURE:
<221> NAME/KEY: misc_feature
<222> LOCATION: (6)..(7)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (8)..(8)
<223> OTHER INFORMATION: deoxyribonucleotide
<220> FEATURE:
<221> NAME/KEY: misc_feature
<222> LOCATION: (9)..(14)
<223> OTHER INFORMATION: ribonucleotide
<220> FEATURE:
<221> NAME/KEY: misc_feature
<222> LOCATION: (9)..(9)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (12)..(13)
<223> OTHER INFORMATION: When the nucleotide is a ribonucleotide, a
      hydroxyl group at the 2'-position of ribose therein is substituted
```

```
      by an O-methyl group.
<220> FEATURE:
<221> NAME/KEY: misc_feature
<222> LOCATION: (15)..(15)
<223> OTHER INFORMATION: deoxyribonucleotide
<220> FEATURE:
<221> NAME/KEY: misc_feature
<222> LOCATION: (16)..(18)
<223> OTHER INFORMATION: ribonucleotide
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: deoxyribonucleotide
<220> FEATURE:
<221> NAME/KEY: misc_feature
<222> LOCATION: (20)..(27)
<223> OTHER INFORMATION: ribonucleotide
<220> FEATURE:
<221> NAME/KEY: misc_feature
<222> LOCATION: (22)..(25)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (26)..(26)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (28)..(29)
<223> OTHER INFORMATION: deoxyribonucleotide

<400> SEQUENCE: 97
gguagccgga ggagtcagta aucgguacc                                          29

<210> SEQ ID NO 98
<211> LENGTH: 27
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(2)
<223> OTHER INFORMATION: ribonucleotide
<220> FEATURE:
<221> NAME/KEY: misc_feature
<222> LOCATION: (1)..(2)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (3)..(3)
<223> OTHER INFORMATION: deoxyribonucleotide
<220> FEATURE:
<221> NAME/KEY: misc_feature
<222> LOCATION: (4)..(6)
<223> OTHER INFORMATION: ribonucleotide
<220> FEATURE:
<221> NAME/KEY: misc_feature
<222> LOCATION: (5)..(6)
<223> OTHER INFORMATION: When the nucleotide is a ribonucleotide, a
```

```
       hydroxyl group at the 2'-position of ribose therein is substituted
       by an O-methyl group.
<220> FEATURE:
<221> NAME/KEY: misc_feature
<222> LOCATION: (7)..(7)
<223> OTHER INFORMATION: deoxyribonucleotide
<220> FEATURE:
<221> NAME/KEY: misc_feature
<222> LOCATION: (8)..(13)
<223> OTHER INFORMATION: ribonucleotide
<220> FEATURE:
<221> NAME/KEY: misc_feature
<222> LOCATION: (8)..(8)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (11)..(12)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (14)..(14)
<223> OTHER INFORMATION: deoxyribonucleotide
<220> FEATURE:
<221> NAME/KEY: misc_feature
<222> LOCATION: (15)..(17)
<223> OTHER INFORMATION: ribonucleotide
<220> FEATURE:
<221> NAME/KEY: misc_feature
<222> LOCATION: (15)..(15)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(26)
<223> OTHER INFORMATION: ribonucleotide
<220> FEATURE:
<221> NAME/KEY: misc_feature
<222> LOCATION: (21)..(24)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (25)..(25)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (26)..(26)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (27)..(27)
<223> OTHER INFORMATION: deoxyribonucleotide

<400> SEQUENCE: 98
guagccggag gagtcagtaa ucgguac                                          27

<210> SEQ ID NO 99
<211> LENGTH: 25
<212> TYPE: DNA
<213> ORGANISM: Artificial Sequence
<220> FEATURE:
<223> OTHER INFORMATION: Aptamer against interleukin-17
<220> FEATURE:
```

```
<221> NAME/KEY: misc_feature
<222> LOCATION: (1)..(1)
<223> OTHER INFORMATION: ribonucleotide
<220> FEATURE:
<221> NAME/KEY: misc_feature
<222> LOCATION: (1)..(1)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (2)..(2)
<223> OTHER INFORMATION: deoxyribonucleotide
<220> FEATURE:
<221> NAME/KEY: misc_feature
<222> LOCATION: (3)..(5)
<223> OTHER INFORMATION: ribonucleotide
<220> FEATURE:
<221> NAME/KEY: misc_feature
<222> LOCATION: (4)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(12)
<223> OTHER INFORMATION: ribonucleotide
<220> FEATURE:
<221> NAME/KEY: misc_feature
<222> LOCATION: (7)..(7)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (13)..(13)
<223> OTHER INFORMATION: deoxyribonucleotide
<220> FEATURE:
<221> NAME/KEY: misc_feature
<222> LOCATION: (14)..(16)
<223> OTHER INFORMATION: ribonucleotide
<220> FEATURE:
<221> NAME/KEY: misc_feature
<222> LOCATION: (14)..(14)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(25)
<223> OTHER INFORMATION: ribonucleotide
<220> FEATURE:
<221> NAME/KEY: misc_feature
<222> LOCATION: (20)..(23)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (24)..(24)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
```

```
<222> LOCATION: (25)..(25)
<223> OTHER INFORMATION: When the nucleotide is a ribonucleotide, a
      hydroxyl group at the 2'-position of ribose therein is substituted
      by an O-methyl group.

<400> SEQUENCE: 99
uagccggagg agtcagtaau cggua                                          25

<210> SEQ ID NO 100
<211> LENGTH: 29
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(7)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: Nucleotide is phosphorothioated.
<220> FEATURE:
<221> NAME/KEY: misc_feature
<222> LOCATION: (6)..(7)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (8)..(8)
<223> OTHER INFORMATION: deoxyribonucleotide
<220> FEATURE:
<221> NAME/KEY: misc_feature
<222> LOCATION: (9)..(14)
<223> OTHER INFORMATION: ribonucleotide
<220> FEATURE:
<221> NAME/KEY: misc_feature
<222> LOCATION: (9)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (12)..(13)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (14)..(14)
<223> OTHER INFORMATION: Nucleotide is phosphorothioated.
<220> FEATURE:
<221> NAME/KEY: misc_feature
<222> LOCATION: (15)..(15)
<223> OTHER INFORMATION: deoxyribonucleotide
<220> FEATURE:
<221> NAME/KEY: misc_feature
<222> LOCATION: (16)..(18)
<223> OTHER INFORMATION: ribonucleotide
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (17)..(17)
<223> OTHER INFORMATION: When the nucleotide is a ribonucleotide, a
      hydroxyl group at the 2'-position of ribose therein is substituted
```

```
      by a fluorine atom.
<220> FEATURE:
<221> NAME/KEY: misc_feature
<222> LOCATION: (18)..(18)
<223> OTHER INFORMATION: Nucleotide is phosphorothioated.
<220> FEATURE:
<221> NAME/KEY: misc_feature
<222> LOCATION: (19)..(19)
<223> OTHER INFORMATION: deoxyribonucleotide
<220> FEATURE:
<221> NAME/KEY: misc_feature
<222> LOCATION: (20)..(29)
<223> OTHER INFORMATION: ribonucleotide
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (22)..(29)
<223> OTHER INFORMATION: When the nucleotide is a ribonucleotide, a
      hydroxyl group at the 2'-position of ribose therein is substituted
      by an O-methyl group.

<400> SEQUENCE: 100
gguagccgga ggagtcagta aucgguacc                                           29

<210> SEQ ID NO 101
<211> LENGTH: 27
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(6)
<223> OTHER INFORMATION: ribonucleotide
<220> FEATURE:
<221> NAME/KEY: misc_feature
<222> LOCATION: (1)..(3)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (4)..(4)
<223> OTHER INFORMATION: Nucleotide is phosphorothioated.
<220> FEATURE:
<221> NAME/KEY: misc_feature
<222> LOCATION: (5)..(6)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(7)
<223> OTHER INFORMATION: deoxyribonucleotide
<220> FEATURE:
<221> NAME/KEY: misc_feature
<222> LOCATION: (8)..(13)
<223> OTHER INFORMATION: ribonucleotide
<220> FEATURE:
<221> NAME/KEY: misc_feature
<222> LOCATION: (8)..(9)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(12)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
```

```
<222> LOCATION: (13)..(13)
<223> OTHER INFORMATION: Nucleotide is phosphorothioated.
<220> FEATURE:
<221> NAME/KEY: misc_feature
<222> LOCATION: (14)..(14)
<223> OTHER INFORMATION: deoxyribonucleotide
<220> FEATURE:
<221> NAME/KEY: misc_feature
<222> LOCATION: (15)..(17)
<223> OTHER INFORMATION: ribonucleotide
<220> FEATURE:
<221> NAME/KEY: misc_feature
<222> LOCATION: (15)..(15)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (17)..(17)
<223> OTHER INFORMATION: Nucleotide is phosphorothioated.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(28)
<223> OTHER INFORMATION: ribonucleotide
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (21)..(27)
<223> OTHER INFORMATION: When the nucleotide is a ribonucleotide, a
      hydroxyl group at the 2'-position of ribose therein is substituted
      by an O-methyl group.

<400> SEQUENCE: 101
guagccggag gagtcagtaa ucgguac                                            27

<210> SEQ ID NO 102
<211> LENGTH: 25
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(5)
<223> OTHER INFORMATION: ribonucleotide
<220> FEATURE:
<221> NAME/KEY: misc_feature
<222> LOCATION: (1)..(2)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (3)..(3)
<223> OTHER INFORMATION: Nucleotide is phosphorothioated.
<220> FEATURE:
<221> NAME/KEY: misc_feature
<222> LOCATION: (4)..(5)
<223> OTHER INFORMATION: When the nucleotide is a ribonucleotide, a
      hydroxyl group at the 2'-position of ribose therein is substituted
      by an O-methyl group.
<220> FEATURE:
```

```
<221> NAME/KEY: misc_feature
<222> LOCATION: (6)..(6)
<223> OTHER INFORMATION: deoxyribonucleotide
<220> FEATURE:
<221> NAME/KEY: misc_feature
<222> LOCATION: (7)..(12)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(11)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (12)..(12)
<223> OTHER INFORMATION: Nucleotide is phosphorothioated.
<220> FEATURE:
<221> NAME/KEY: misc_feature
<222> LOCATION: (13)..(13)
<223> OTHER INFORMATION: deoxyribonucleotide
<220> FEATURE:
<221> NAME/KEY: misc_feature
<222> LOCATION: (14)..(16)
<223> OTHER INFORMATION: ribonucleotide
<220> FEATURE:
<221> NAME/KEY: misc_feature
<222> LOCATION: (14)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (16)..(16)
<223> OTHER INFORMATION: Nucleotide is phosphorothioated.
<220> FEATURE:
<221> NAME/KEY: misc_feature
<222> LOCATION: (17)..(17)
<223> OTHER INFORMATION: deoxyribonucleotide
<220> FEATURE:
<221> NAME/KEY: misc_feature
<222> LOCATION: (18)..(27)
<223> OTHER INFORMATION: ribonucleotide
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(26)
<223> OTHER INFORMATION: When the nucleotide is a ribonucleotide, a
      hydroxyl group at the 2'-position of ribose therein is substituted
      by an O-methyl group.

<400> SEQUENCE: 102
uagccggagg agtcagtaau cggua                                              25

<210> SEQ ID NO 103
<211> LENGTH: 29
<212> TYPE: DNA
<213> ORGANISM: Artificial Sequence
<220> FEATURE:
<223> OTHER INFORMATION: Aptamer against interleukin-17
```

```
<220> FEATURE:
<221> NAME/KEY: misc_feature
<222> LOCATION: (1)..(3)
<223> OTHER INFORMATION: ribonucleotide
<220> FEATURE:
<221> NAME/KEY: misc_feature
<222> LOCATION: (1)..(3)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (4)..(4)
<223> OTHER INFORMATION: deoxyribonucleotide
<220> FEATURE:
<221> NAME/KEY: misc_feature
<222> LOCATION: (5)..(7)
<223> OTHER INFORMATION: ribonucleotide
<220> FEATURE:
<221> NAME/KEY: misc_feature
<222> LOCATION: (5)..(5)
<223> OTHER INFORMATION: Nucleotide is phosphorothioated.
<220> FEATURE:
<221> NAME/KEY: misc_feature
<222> LOCATION: (6)..(7)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (8)..(8)
<223> OTHER INFORMATION: deoxyribonucleotide
<220> FEATURE:
<221> NAME/KEY: misc_feature
<222> LOCATION: (9)..(14)
<223> OTHER INFORMATION: ribonucleotide
<220> FEATURE:
<221> NAME/KEY: misc_feature
<222> LOCATION: (9)..(9)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (12)..(13)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: deoxyribonucleotide
<220> FEATURE:
<221> NAME/KEY: misc_feature
<222> LOCATION: (16)..(18)
<223> OTHER INFORMATION: ribonucleotide
<220> FEATURE:
<221> NAME/KEY: misc_feature
<222> LOCATION: (16)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: deoxyribonucleotide
<220> FEATURE:
<221> NAME/KEY: misc_feature
<222> LOCATION: (20)..(29)
<223> OTHER INFORMATION: ribonucleotide
<220> FEATURE:
<221> NAME/KEY: misc_feature
<222> LOCATION: (22)..(25)
```

```
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (26)..(26)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (27)..(29)
<223> OTHER INFORMATION: When the nucleotide is a ribonucleotide, a
      hydroxyl group at the 2'-position of ribose therein is substituted
      by an O-methyl group.

<400> SEQUENCE: 103
gguagccgga ggagtcagta aucgguacc                                          29

<210> SEQ ID NO 104
<211> LENGTH: 27
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(2)
<223> OTHER INFORMATION: ribonucleotide
<220> FEATURE:
<221> NAME/KEY: misc_feature
<222> LOCATION: (1)..(2)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (3)..(3)
<223> OTHER INFORMATION: deoxyribonucleotide
<220> FEATURE:
<221> NAME/KEY: misc_feature
<222> LOCATION: (4)..(6)
<223> OTHER INFORMATION: ribonucleotide
<220> FEATURE:
<221> NAME/KEY: misc_feature
<222> LOCATION: (4)..(4)
<223> OTHER INFORMATION: Nucleotide is phosphorothioated.
<220> FEATURE:
<221> NAME/KEY: misc_feature
<222> LOCATION: (5)..(6)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (7)..(7)
<223> OTHER INFORMATION: deoxyribonucleotide
<220> FEATURE:
<221> NAME/KEY: misc_feature
<222> LOCATION: (8)..(13)
<223> OTHER INFORMATION: ribonucleotide
<220> FEATURE:
<221> NAME/KEY: misc_feature
<222> LOCATION: (8)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (11)..(12)
<223> OTHER INFORMATION: When the nucleotide is a ribonucleotide, a
``` hydroxyl group at the 2'-position of ribose therein is substituted
        by an O-methyl group.
<220> FEATURE:
<221> NAME/KEY: misc_feature
<222> LOCATION: (14)..(14)
<223> OTHER INFORMATION: deoxyribonucleotide
<220> FEATURE:
<221> NAME/KEY: misc_feature
<222> LOCATION: (15)..(17)
<223> OTHER INFORMATION: ribonucleotide
<220> FEATURE:
<221> NAME/KEY: misc_feature
<222> LOCATION: (15)..(16)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (18)..(18)
<223> OTHER INFORMATION: deoxyribonucleotide
<220> FEATURE:
<221> NAME/KEY: misc_feature
<222> LOCATION: (19)..(27)
<223> OTHER INFORMATION: ribonucleotide
<220> FEATURE:
<221> NAME/KEY: misc_feature
<222> LOCATION: (21)..(24)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (25)..(25)
<223> OTHER INFORMATION: When the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (26)..(27)
<223> OTHER INFORMATION: When the nucleotide is a ribonucleotide, a
        hydroxyl group at the 2'-position of ribose therein is substituted
        by an O-methyl group.

<400> SEQUENCE: 104
guagccggag gagtcagtaa ucgguac                                          27

<210> SEQ ID NO 105
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
        hydroxyl group at the 2'-position of ribose therein is substituted
        by an O-methyl group.
<220> FEATURE:
<221> NAME/KEY: misc_feature
<222> LOCATION: (5)..(6)
<223> OTHER INFORMATION: ribonucleotide or deoxyribonucleotide
<220> FEATURE:
<221> NAME/KEY: misc_feature
<222> LOCATION: (6)..(6)
<223> OTHER INFORMATION: Nucleotide is non-modified or
        phosphorothioated, or when the nucleotide is a ribonucleotide, a
        hydroxyl group at the 2'-position of ribose therein is substituted
        by a fluorine atom.
<220> FEATURE:
<221> NAME/KEY: misc_feature
<222> LOCATION: (7)..(8)
<223> OTHER INFORMATION: ribonucleotide

```
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: ribonucleotide or deoxyribonucleotide
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: ribonucleotide or deoxyribonucleotide
<220> FEATURE:
<221> NAME/KEY: misc_feature
<222> LOCATION: (11)..(11)
<223> OTHER INFORMATION: Nucleotide is non-modified, or when the
      nucleotide is a ribonucleotide, a hydroxyl group at the 2'-
      position of ribose therein is substituted by a fluorine atom or an
      O-methyl group.
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (12)..(12)
<223> OTHER INFORMATION: Nucleotide is non-modified or
      phosphorothioated.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is non-modified or
      phosphorothioated.
<220> FEATURE:
<221> NAME/KEY: misc_feature
<222> LOCATION: (16)..(16)
<223> OTHER INFORMATION: ribonucleotide or deoxyribonucleotide
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (16)..(16)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
```

-continued

```
<222> LOCATION: (18)..(18)
<223> OTHER INFORMATION: ribonucleotide or deoxyribonucleotide
<220> FEATURE:
<221> NAME/KEY: misc_feature
<222> LOCATION: (18)..(18)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (19)..(19)
<223> OTHER INFORMATION: ucleotide is non-modified or phosphorothioated,
      or when the nucleotide is a ribonucleotide, a hydroxyl group at
      the 2'-position of ribose therein is substituted by an O-methyl
      group.
<220> FEATURE:
<221> NAME/KEY: misc_feature
<222> LOCATION: (20)..(20)
<223> OTHER INFORMATION: ribonucleotide or deoxyribonucleotide
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (20)..(20)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(21)
<223> OTHER INFORMATION: The base is adenine or guanine.
<220> FEATURE:
<221> NAME/KEY: misc_feature
<222> LOCATION: (21)..(22)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (22)..(22)
<223> OTHER INFORMATION: ribonucleotide or deoxyribonucleotide
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(31)
<223> OTHER INFORMATION: ribonucleotide or deoxyribonucleotide
<220> FEATURE:
<221> NAME/KEY: misc_feature
<222> LOCATION: (27)..(27)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (27)..(27)
<223> OTHER INFORMATION: a ribonucleotide wherein the base is uracil, a
      deoxyribonucleotide wherein the base is uracil or a
      deoxyribonucleotide wherein the base is thymine
```

```
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 105
ggguagccgg aggagncagn raucgguacc c                                  31

<210> SEQ ID NO 106
<211> LENGTH: 29
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(3)
<223> OTHER INFORMATION: ribonucleotide
<220> FEATURE:
<221> NAME/KEY: misc_feature
<222> LOCATION: (1)..(4)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (4)..(5)
<223> OTHER INFORMATION: ribonucleotide or deoxyribonucleotide
<220> FEATURE:
<221> NAME/KEY: misc_feature
<222> LOCATION: (5)..(5)
<223> OTHER INFORMATION: Nucleotide is non-modified or
      phosphorothioated, or when the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (6)..(7)
<223> OTHER INFORMATION: ribonucleotide
<220> FEATURE:
<221> NAME/KEY: misc_feature
<222> LOCATION: (6)..(7)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (8)..(8)
<223> OTHER INFORMATION: ribonucleotide or deoxyribonucleotide
<220> FEATURE:
<221> NAME/KEY: misc_feature
<222> LOCATION: (9)..(9)
<223> OTHER INFORMATION: ribonucleotide
<220> FEATURE:
<221> NAME/KEY: misc_feature
<222> LOCATION: (9)..(9)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (10)..(10)
<223> OTHER INFORMATION: ribonucleotide or deoxyribonucleotide
<220> FEATURE:
<221> NAME/KEY: misc_feature
<222> LOCATION: (10)..(10)
<223> OTHER INFORMATION: Nucleotide is non-modified, or when the
      nucleotide is a ribonucleotide, a hydroxyl group at the 2'-
      position of ribose therein is substituted by a fluorine atom or an
      O-methyl group.
<220> FEATURE:
<221> NAME/KEY: misc_feature
<222> LOCATION: (11)..(14)
<223> OTHER INFORMATION: ribonucleotide
<220> FEATURE:
```

```
<221> NAME/KEY: misc_feature
<222> LOCATION: (11)..(11)
<223> OTHER INFORMATION: Nucleotide is non-modified or
      phosphorothioated.
<220> FEATURE:
<221> NAME/KEY: misc_feature
<222> LOCATION: (12)..(13)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (14)..(14)
<223> OTHER INFORMATION: Nucleotide is non-modified or
      phosphorothioated.
<220> FEATURE:
<221> NAME/KEY: misc_feature
<222> LOCATION: (15)..(15)
<223> OTHER INFORMATION: ribonucleotide or deoxyribonucleotide
<220> FEATURE:
<221> NAME/KEY: misc_feature
<222> LOCATION: (15)..(15)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (15)..(15)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (16)..(16)
<223> OTHER INFORMATION: ribonucleotide
<220> FEATURE:
<221> NAME/KEY: misc_feature
<222> LOCATION: (16)..(16)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (17)..(17)
<223> OTHER INFORMATION: ribonucleotide or deoxyribonucleotide
<220> FEATURE:
<221> NAME/KEY: misc_feature
<222> LOCATION: (17)..(17)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (18)..(18)
<223> OTHER INFORMATION: ribonucleotide
<220> FEATURE:
<221> NAME/KEY: misc_feature
<222> LOCATION: (18)..(18)
<223> OTHER INFORMATION: ucleotide is non-modified or phosphorothioated,
      or when the nucleotide is a ribonucleotide, a hydroxyl group at
      the 2'-position of ribose therein is substituted by an O-methyl
      group.
<220> FEATURE:
<221> NAME/KEY: misc_feature
<222> LOCATION: (19)..(19)
<223> OTHER INFORMATION: ribonucleotide or deoxyribonucleotide
<220> FEATURE:
<221> NAME/KEY: misc_feature
<222> LOCATION: (19)..(19)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
```

```
<221> NAME/KEY: misc_feature
<222> LOCATION: (20)..(20)
<223> OTHER INFORMATION: ribonucleotide
<220> FEATURE:
<221> NAME/KEY: misc_feature
<222> LOCATION: (20)..(20)
<223> OTHER INFORMATION: The base is adenine or guanine.
<220> FEATURE:
<221> NAME/KEY: misc_feature
<222> LOCATION: (20)..(21)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (21)..(21)
<223> OTHER INFORMATION: ribonucleotide or deoxyribonucleotide
<220> FEATURE:
<221> NAME/KEY: misc_feature
<222> LOCATION: (22)..(25)
<223> OTHER INFORMATION: ribonucleotide
<220> FEATURE:
<221> NAME/KEY: misc_feature
<222> LOCATION: (22)..(25)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (26)..(29)
<223> OTHER INFORMATION: ribonucleotide or deoxyribonucleotide
<220> FEATURE:
<221> NAME/KEY: misc_feature
<222> LOCATION: (26)..(26)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (26)..(26)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (27)..(29)
<223> OTHER INFORMATION: When the nucleotide is a ribonucleotide, a
      hydroxyl group at the 2'-position of ribose therein is substituted
      by an O-methyl group.

<400> SEQUENCE: 106
gguagccgga ggagncagnr aucgguacc                                    29

<210> SEQ ID NO 107
<211> LENGTH: 27
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(2)
<223> OTHER INFORMATION: ribonucleotide
<220> FEATURE:
<221> NAME/KEY: misc_feature
<222> LOCATION: (1)..(3)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (3)..(4)
<223> OTHER INFORMATION: ribonucleotide or deoxyribonucleotide
<220> FEATURE:
<221> NAME/KEY: misc_feature
<222> LOCATION: (4)..(4)
<223> OTHER INFORMATION: Nucleotide is non-modified or
```

```
       phosphorothioated, or when the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (5)..(6)
<223> OTHER INFORMATION: ribonucleotide
<220> FEATURE:
<221> NAME/KEY: misc_feature
<222> LOCATION: (5)..(6)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (7)..(7)
<223> OTHER INFORMATION: ribonucleotide or deoxyribonucleotide
<220> FEATURE:
<221> NAME/KEY: misc_feature
<222> LOCATION: (8)..(8)
<223> OTHER INFORMATION: ribonucleotide
<220> FEATURE:
<221> NAME/KEY: misc_feature
<222> LOCATION: (8)..(8)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (9)..(9)
<223> OTHER INFORMATION: ribonucleotide or deoxyribonucleotide
<220> FEATURE:
<221> NAME/KEY: misc_feature
<222> LOCATION: (9)..(9)
<223> OTHER INFORMATION: Nucleotide is non-modified, or when the
       nucleotide is a ribonucleotide, a hydroxyl group at the 2'-
       position of ribose therein is substituted by a fluorine atom or an
       O-methyl group.
<220> FEATURE:
<221> NAME/KEY: misc_feature
<222> LOCATION: (10)..(11)
<223> OTHER INFORMATION: ribonucleotide
<220> FEATURE:
<221> NAME/KEY: misc_feature
<222> LOCATION: (10)..(10)
<223> OTHER INFORMATION: Nucleotide is non-modified or
       phosphorothioated.
<220> FEATURE:
<221> NAME/KEY: misc_feature
<222> LOCATION: (11)..(12)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (13)..(13)
<223> OTHER INFORMATION: Nucleotide is non-modified or
       phosphorothioated.
<220> FEATURE:
<221> NAME/KEY: misc_feature
<222> LOCATION: (14)..(14)
<223> OTHER INFORMATION: ribonucleotide or deoxyribonucleotide
<220> FEATURE:
<221> NAME/KEY: misc_feature
<222> LOCATION: (14)..(14)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (14)..(14)
<223> OTHER INFORMATION: a ribonucleotide wherein the base is uracil, a
       deoxyribonucleotide wherein the base is uracil or a
       deoxyribonucleotide wherein the base is thymine
<220> FEATURE:
<221> NAME/KEY: misc_feature
<222> LOCATION: (15)..(15)
<223> OTHER INFORMATION: ribonucleotide
<220> FEATURE:
```

```
<220> FEATURE:
<221> NAME/KEY: misc_feature
<222> LOCATION: (15)..(15)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (16)..(16)
<223> OTHER INFORMATION: ribonucleotide or deoxyribonucleotide
<220> FEATURE:
<221> NAME/KEY: misc_feature
<222> LOCATION: (16)..(16)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (17)..(17)
<223> OTHER INFORMATION: ribonucleotide
<220> FEATURE:
<221> NAME/KEY: misc_feature
<222> LOCATION: (17)..(17)
<223> OTHER INFORMATION: ucleotide is non-modified or phosphorothioated,
      or when the nucleotide is a ribonucleotide, a hydroxyl group at
      the 2'-position of ribose therein is substituted by an O-methyl
      group.
<220> FEATURE:
<221> NAME/KEY: misc_feature
<222> LOCATION: (18)..(18)
<223> OTHER INFORMATION: ribonucleotide or deoxyribonucleotide
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (18)..(18)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (19)..(19)
<223> OTHER INFORMATION: The base is adenine or guanine.
<220> FEATURE:
<221> NAME/KEY: misc_feature
<222> LOCATION: (19)..(20)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (20)..(20)
<223> OTHER INFORMATION: ribonucleotide or deoxyribonucleotide
<220> FEATURE:
<221> NAME/KEY: misc_feature
<222> LOCATION: (21)..(24)
<223> OTHER INFORMATION: ribonucleotide
<220> FEATURE:
<221> NAME/KEY: misc_feature
<222> LOCATION: (21)..(24)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (25)..(27)
<223> OTHER INFORMATION: ribonucleotide or deoxyribonucleotide
<220> FEATURE:
<221> NAME/KEY: misc_feature
<222> LOCATION: (25)..(25)
<223> OTHER INFORMATION: When nucleotide is a ribonucleotide, a hydroxyl
      group at the 2'-position of ribose therein is substituted by a
```

```
          fluorine atom or an O-methyl group.
<220> FEATURE:
<221> NAME/KEY: misc_feature
<222> LOCATION: (25)..(25)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (26)..(27)
<223> OTHER INFORMATION: When the nucleotide is a ribonucleotide, a
      hydroxyl group at the 2'-position of ribose therein is substituted
      by an O-methyl group.

<400> SEQUENCE: 107
guagccggag gagncagnra ucgguac                                               27

<210> SEQ ID NO 108
<211> LENGTH: 25
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(1)
<223> OTHER INFORMATION: ribonucleotide
<220> FEATURE:
<221> NAME/KEY: misc_feature
<222> LOCATION: (1)..(2)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (2)..(3)
<223> OTHER INFORMATION: ribonucleotide or deoxyribonucleotide
<220> FEATURE:
<221> NAME/KEY: misc_feature
<222> LOCATION: (3)..(3)
<223> OTHER INFORMATION: Nucleotide is non-modified or
      phosphorothioated, or when the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (4)..(5)
<223> OTHER INFORMATION: ribonucleotide
<220> FEATURE:
<221> NAME/KEY: misc_feature
<222> LOCATION: (4)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (6)..(6)
<223> OTHER INFORMATION: ribonucleotide or deoxyribonucleotide
<220> FEATURE:
<221> NAME/KEY: misc_feature
<222> LOCATION: (7)..(7)
<223> OTHER INFORMATION: ribonucleotide
<220> FEATURE:
<221> NAME/KEY: misc_feature
<222> LOCATION: (7)..(7)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (8)..(8)
<223> OTHER INFORMATION: ribonucleotide or deoxyribonucleotide
<220> FEATURE:
<221> NAME/KEY: misc_feature
<222> LOCATION: (8)..(8)
<223> OTHER INFORMATION: Nucleotide is non-modified, or when the
      nucleotide is a ribonucleotide, a hydroxyl group at the 2'-
```

```
       position of ribose therein is substituted by a fluorine atom or an
       O-methyl group.
<220> FEATURE:
<221> NAME/KEY: misc_feature
<222> LOCATION: (9)..(10)
<223> OTHER INFORMATION: ribonucleotide
<220> FEATURE:
<221> NAME/KEY: misc_feature
<222> LOCATION: (9)..(9)
<223> OTHER INFORMATION: Nucleotide is non-modified or
       phosphorothioated.
<220> FEATURE:
<221> NAME/KEY: misc_feature
<222> LOCATION: (10)..(11)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (12)..(12)
<223> OTHER INFORMATION: Nucleotide is non-modified or
       phosphorothioated.
<220> FEATURE:
<221> NAME/KEY: misc_feature
<222> LOCATION: (13)..(13)
<223> OTHER INFORMATION: ribonucleotide or deoxyribonucleotide
<220> FEATURE:
<221> NAME/KEY: misc_feature
<222> LOCATION: (13)..(13)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (13)..(13)
<223> OTHER INFORMATION: a ribonucleotide wherein the base is uracil, a
       deoxyribonucleotide wherein the base is uracil or a
       deoxyribonucleotide wherein the base is thymine
<220> FEATURE:
<221> NAME/KEY: misc_feature
<222> LOCATION: (14)..(14)
<223> OTHER INFORMATION: ribonucleotide
<220> FEATURE:
<221> NAME/KEY: misc_feature
<222> LOCATION: (14)..(14)
<223> OTHER INFORMATION: When nucleotide is a ribonucleotide, a hydroxyl
       group at the 2'-position of ribose therein is substituted by a
       fluorine atom or an O-methyl group.
<220> FEATURE:
<221> NAME/KEY: misc_feature
<222> LOCATION: (15)..(15)
<223> OTHER INFORMATION: ribonucleotide or deoxyribonucleotide
<220> FEATURE:
<221> NAME/KEY: misc_feature
<222> LOCATION: (15)..(15)
<223> OTHER INFORMATION: Nucleotide is non-modified, or when the
       nucleotide is a ribonucleotide, a hydroxyl group at the 2'-
       position of ribose therein is substituted by a fluorine atom.
<220> FEATURE:
<221> NAME/KEY: misc_feature
<222> LOCATION: (16)..(16)
<223> OTHER INFORMATION: ribonucleotide
<220> FEATURE:
<221> NAME/KEY: misc_feature
<222> LOCATION: (16)..(16)
<223> OTHER INFORMATION: ucleotide is non-modified or phosphorothioated,
       or when the nucleotide is a ribonucleotide, a hydroxyl group at
       the 2'-position of ribose therein is substituted by an O-methyl
       group.
<220> FEATURE:
<221> NAME/KEY: misc_feature
<222> LOCATION: (17)..(17)
<223> OTHER INFORMATION: ribonucleotide or deoxyribonucleotide
<220> FEATURE:
<221> NAME/KEY: misc_feature
<222> LOCATION: (17)..(17)
<223> OTHER INFORMATION: When the nucleotide is a ribonucleotide, a
       hydroxyl group at the 2'-position of ribose therein is substituted
       by a fluorine atom.
```

```
<220> FEATURE:
<221> NAME/KEY: misc_feature
<222> LOCATION: (17)..(17)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (18)..(18)
<223> OTHER INFORMATION: ribonucleotide
<220> FEATURE:
<221> NAME/KEY: misc_feature
<222> LOCATION: (18)..(18)
<223> OTHER INFORMATION: The base is adenine or guanine.
<220> FEATURE:
<221> NAME/KEY: misc_feature
<222> LOCATION: (18)..(19)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (19)..(19)
<223> OTHER INFORMATION: ribonucleotide or deoxyribonucleotide
<220> FEATURE:
<221> NAME/KEY: misc_feature
<222> LOCATION: (20)..(23)
<223> OTHER INFORMATION: ribonucleotide
<220> FEATURE:
<221> NAME/KEY: misc_feature
<222> LOCATION: (20)..(23)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (24)..(26)
<223> OTHER INFORMATION: ribonucleotide or deoxyribonucleotide
<220> FEATURE:
<221> NAME/KEY: misc_feature
<222> LOCATION: (24)..(24)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (24)..(24)
<223> OTHER INFORMATION: a ribonucleotide wherein the base is uracil, a
      deoxyribonucleotide wherein the base is uracil or a
      deoxyribonucleotide wherein the base is thymine
<220> FEATURE:
<221> NAME/KEY: misc_feature
<222> LOCATION: (25)..(25)
<223> OTHER INFORMATION: When the nucleotide is a ribonucleotide, a
      hydroxyl group at the 2'-position of ribose therein is substituted
      by an O-methyl group.

<400> SEQUENCE: 108
uagccggagg agncagnrau cggua                                              25

<210> SEQ ID NO 109
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(8)
<223> OTHER INFORMATION: ribonucleotide
<220> FEATURE:
<221> NAME/KEY: misc_feature
<222> LOCATION: (1)..(3)
<223> OTHER INFORMATION: Nucleotide is modified with Locked Nucleic Acid
      (LNA), or when the nucleotide is a ribonucleotide, a hydroxyl
      group at the 2'-position of ribose therein is substituted by an
      O-methyl group.
```

```
<220> FEATURE:
<221> NAME/KEY: misc_feature
<222> LOCATION: (4)..(4)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (6)..(6)
<223> OTHER INFORMATION: When nucleotide is a ribonucleotide, it is
      phosphorothioated.
<220> FEATURE:
<221> NAME/KEY: misc_feature
<222> LOCATION: (7)..(8)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (9)..(9)
<223> OTHER INFORMATION: ribonucleotide or deoxyribonucleotide
<220> FEATURE:
<221> NAME/KEY: misc_feature
<222> LOCATION: (9)..(9)
<223> OTHER INFORMATION: When nucleotide is a ribonucleotide, it is
      phosphorothioated.
<220> FEATURE:
<221> NAME/KEY: misc_feature
<222> LOCATION: (10)..(28)
<223> OTHER INFORMATION: ribonucleotide
<220> FEATURE:
<221> NAME/KEY: misc_feature
<222> LOCATION: (10)..(10)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (16)..(17)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (20)..(20)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (23)..(24)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (27)..(27)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (29)..(31)
<223> OTHER INFORMATION: ribonucleotide or deoxyribonucleotide
<220> FEATURE:
<221> NAME/KEY: misc_feature
<222> LOCATION: (29)..(31)
<223> OTHER INFORMATION: Nucleotide is non-modified, or modified with
      LNA.

<400> SEQUENCE: 109
ggguagccgg aggagucagu aaucgguacc c                                  31

<210> SEQ ID NO 110
<211> LENGTH: 29
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(7)
<223> OTHER INFORMATION: ribonucleotide
```

```
<220> FEATURE:
<221> NAME/KEY: misc_feature
<222> LOCATION: (1)..(2)
<223> OTHER INFORMATION: Nucleotide is modified with Locked Nucleic Acid
      (LNA), or when the nucleotide is a ribonucleotide, a hydroxyl
      group at the 2'-position of ribose therein is substituted by an
      O-methyl group.
<220> FEATURE:
<221> NAME/KEY: misc_feature
<222> LOCATION: (3)..(3)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (5)..(5)
<223> OTHER INFORMATION: When nucleotide is a ribonucleotide, it is
      phosphorothioated.
<220> FEATURE:
<221> NAME/KEY: misc_feature
<222> LOCATION: (6)..(7)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (8)..(8)
<223> OTHER INFORMATION: ribonucleotide or deoxyribonucleotide
<220> FEATURE:
<221> NAME/KEY: misc_feature
<222> LOCATION: (8)..(8)
<223> OTHER INFORMATION: When nucleotide is a ribonucleotide, it is
      phosphorothioated.
<220> FEATURE:
<221> NAME/KEY: misc_feature
<222> LOCATION: (9)..(27)
<223> OTHER INFORMATION: ribonucleotide
<220> FEATURE:
<221> NAME/KEY: misc_feature
<222> LOCATION: (9)..(9)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (15)..(16)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (19)..(19)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (22)..(23)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (26)..(26)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (28)..(29)
<223> OTHER INFORMATION: ribonucleotide or deoxyribonucleotide
<220> FEATURE:
<221> NAME/KEY: misc_feature
<222> LOCATION: (28)..(29)
<223> OTHER INFORMATION: Nucleotide is non-modified, or modified with
      LNA.

<400> SEQUENCE: 110
gguagccgga ggagucagua aucgguacc                                      29

<210> SEQ ID NO 111
<211> LENGTH: 27
<212> TYPE: DNA
```

```
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(6)
<223> OTHER INFORMATION: ribonucleotide
<220> FEATURE:
<221> NAME/KEY: misc_feature
<222> LOCATION: (1)..(1)
<223> OTHER INFORMATION: Nucleotide is modified with Locked Nucleic Acid
      (LNA), or when the nucleotide is a ribonucleotide, a hydroxyl
      group at the 2'-position of ribose therein is substituted by an
      O-methyl group.
<220> FEATURE:
<221> NAME/KEY: misc_feature
<222> LOCATION: (2)..(2)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (3)..(3)
<223> OTHER INFORMATION: When nucleotide is a ribonucleotide, it is
      phosphorothioated.
<220> FEATURE:
<221> NAME/KEY: misc_feature
<222> LOCATION: (5)..(6)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (7)..(7)
<223> OTHER INFORMATION: ribonucleotide or deoxyribonucleotide
<220> FEATURE:
<221> NAME/KEY: misc_feature
<222> LOCATION: (7)..(7)
<223> OTHER INFORMATION: When nucleotide is a ribonucleotide, it is
      phosphorothioated.
<220> FEATURE:
<221> NAME/KEY: misc_feature
<222> LOCATION: (8)..(26)
<223> OTHER INFORMATION: ribonucleotide
<220> FEATURE:
<221> NAME/KEY: misc_feature
<222> LOCATION: (8)..(8)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (14)..(15)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (18)..(18)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (21)..(22)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (25)..(25)
<223> OTHER INFORMATION: A hydroxyl group at the 2'-position of ribose
      in the nucleotide is substituted by a fluorine atom.
<220> FEATURE:
<221> NAME/KEY: misc_feature
<222> LOCATION: (27)..(27)
<223> OTHER INFORMATION: ribonucleotide or deoxyribonucleotide
<220> FEATURE:
<221> NAME/KEY: misc_feature
<222> LOCATION: (27)..(27)
<223> OTHER INFORMATION: Nucleotide is non-modified, or modified with
      LNA.

<400> SEQUENCE: 111
```
guagccggag gagucaguaa ucgguac                                    27

<210> SEQ ID NO 112
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: ribonucleotide or deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is non-modified or
      phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: Nucleotide is non-modified, or when the
      nucleotide is a ribonucleotide, a hydroxyl group at the 2'-
      position of ribose therein is substituted by a fluorine atom or an
      O-methyl group.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is non-modified or
      phosphorothioated.
<220> FEATURE:
<221> NAME/KEY: misc_feature
<222> LOCATION: (16)..(16)
<223> OTHER INFORMATION: ribonucleotide or deoxyribonucleotide
<220> FEATURE:
<221> NAME/KEY: misc_feature
<222> LOCATION: (16)..(16)
<223> OTHER INFORMATION: When the nucleotide is a ribonucleotide, a hydroxyl group at the 2'-position of ribose therein is substituted
       by a fluorine atom.
<220> FEATURE:
<221> NAME/KEY: misc_feature
<222> LOCATION: (17)..(19)
<223> OTHER INFORMATION: ribonucleotide
<220> FEATURE:
<221> NAME/KEY: misc_feature
<222> LOCATION: (17)..(17)
<223> OTHER INFORMATION: When nucleotide is a ribonucleotide, a hydroxyl
       group at the 2'-position of ribose therein is substituted by a
       fluorine atom or an O-methyl group.
<220> FEATURE:
<221> NAME/KEY: misc_feature
<222> LOCATION: (18)..(18)
<223> OTHER INFORMATION: Nucleotide is non-modified, or when the
       nucleotide is a ribonucleotide, a hydroxyl group at the 2'-
       position of ribose therein is substituted by a fluorine atom.
<220> FEATURE:
<221> NAME/KEY: misc_feature
<222> LOCATION: (19)..(19)
<223> OTHER INFORMATION: Nucleotide is non-modified or
       phosphorothioated.
<220> FEATURE:
<221> NAME/KEY: misc_feature
<222> LOCATION: (20)..(20)
<223> OTHER INFORMATION: ribonucleotide or deoxyribonucleotide
<220> FEATURE:
<221> NAME/KEY: misc_feature
<222> LOCATION: (20)..(20)
<223> OTHER INFORMATION: When the nucleotide is a ribonucleotide, a
       hydroxyl group at the 2'-position of ribose therein is substituted
       by a fluorine atom.
<220> FEATURE:
<221> NAME/KEY: misc_feature
<222> LOCATION: (21)..(28)
<223> OTHER INFORMATION: ribonucleotide
<220> FEATURE:
<221> NAME/KEY: misc_feature
<222> LOCATION: (21)..(21)
<223> OTHER INFORMATION: The base is adenine or guanine.
<220> FEATURE:
<221> NAME/KEY: misc_feature
<222> LOCATION: (21)..(22)
<223> OTHER INFORMATION: Nucleotide is non-modified, or when the
       nucleotide is a ribonucleotide, a hydroxyl group at the 2'-
       position of ribose therein is substituted by an O-methyl group.
<220> FEATURE:
<221> NAME/KEY: misc_feature
<222> LOCATION: (23)..(26)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (27)..(27)
<223> OTHER INFORMATION: When nucleotide is a ribonucleotide, a hydroxyl
       group at the 2'-position of ribose therein is substituted by a
       fluorine atom or an O-methyl group.
<220> FEATURE:
<221> NAME/KEY: misc_feature
<222> LOCATION: (28)..(31)
<223> OTHER INFORMATION: When the nucleotide is a ribonucleotide, a
       hydroxyl group at the 2'-position of ribose therein is substituted
       by an O-methyl group.
<220> FEATURE:
<221> NAME/KEY: misc_feature
<222> LOCATION: (29)..(31)
<223> OTHER INFORMATION: ribonucleotide or deoxyribonucleotide

<400> SEQUENCE: 112
ggguagccgg aggagncagn raucgguacc c                                    31

<210> SEQ ID NO 113
<211> LENGTH: 31
<212> TYPE: DNA
<213> ORGANISM: Artificial Sequence

```
<220> FEATURE:
<223> OTHER INFORMATION: Aptamer against interleukin-17
<220> FEATURE:
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(6)
<223> OTHER INFORMATION: ribonucleotide or deoxyribonucleotode
<220> FEATURE:
<221> NAME/KEY: misc_feature
<222> LOCATION: (6)..(6)
<223> OTHER INFORMATION: Nucleotide is non-modified or
      phosphorothioated, or when the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (7)..(8)
<223> OTHER INFORMATION: ribonucleotide
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: ribonucleotide or deoxyribonucleotode
<220> FEATURE:
<221> NAME/KEY: misc_feature
<222> LOCATION: (10)..(10)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: ribonucleotide or deoxyribonucleotode
<220> FEATURE:
<221> NAME/KEY: misc_feature
<222> LOCATION: (11)..(11)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (12)..(15)
<223> OTHER INFORMATION: ribonucleotide
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (16)..(16)
<223> OTHER INFORMATION: ribonucleotide or deoxyribonucleotode
<220> FEATURE:
<221> NAME/KEY: misc_feature
<222> LOCATION: (16)..(17)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
```

```
<222> LOCATION: (17)..(17)
<223> OTHER INFORMATION: ribonucleotide
<220> FEATURE:
<221> NAME/KEY: misc_feature
<222> LOCATION: (18)..(18)
<223> OTHER INFORMATION: ribonucleotide or deoxyribonucleotode
<220> FEATURE:
<221> NAME/KEY: misc_feature
<222> LOCATION: (18)..(18)
<223> OTHER INFORMATION: Nucleotide is non-modified, or when the
      nucleotide is a ribonucleotide, a hydroxyl group at the 2'-
      position of ribose therein is substituted by a fluorine atom.
<220> FEATURE:
<221> NAME/KEY: misc_feature
<222> LOCATION: (19)..(19)
<223> OTHER INFORMATION: ribonucleotide
<220> FEATURE:
<221> NAME/KEY: misc_feature
<222> LOCATION: (20)..(20)
<223> OTHER INFORMATION: ribonucleotide or deoxyribonucleotode
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (21)..(22)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (22)..(22)
<223> OTHER INFORMATION: ribonucleotide or deoxyribonucleotode
<220> FEATURE:
<221> NAME/KEY: misc_feature
<222> LOCATION: (23)..(26)
<223> OTHER INFORMATION: ribonucleotide
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(31)
<223> OTHER INFORMATION: ribonucleotide or deoxyribonucleotode
<220> FEATURE:
<221> NAME/KEY: misc_feature
<222> LOCATION: (27)..(27)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 113
ggguagccgg aggagncagn aaucggnacc c                                  31

<210> SEQ ID NO 114
<211> LENGTH: 31
<212> TYPE: DNA
<213> ORGANISM: Artificial Sequence
<220> FEATURE:
<223> OTHER INFORMATION: Aptamer against interleukin-17
<220> FEATURE:
```

```
<221> NAME/KEY: misc_feature
<222> LOCATION: (1)..(4)
<223> OTHER INFORMATION: ribonucleotide
<220> FEATURE:
<221> NAME/KEY: misc_feature
<222> LOCATION: (1)..(5)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (5)..(5)
<223> OTHER INFORMATION: ribonucleotide or deoxyribonucleotide
<220> FEATURE:
<221> NAME/KEY: misc_feature
<222> LOCATION: (6)..(8)
<223> OTHER INFORMATION: ribonucleotide
<220> FEATURE:
<221> NAME/KEY: misc_feature
<222> LOCATION: (6)..(6)
<223> OTHER INFORMATION: Nucleotide is non-modified or
      phosphorothioated.
<220> FEATURE:
<221> NAME/KEY: misc_feature
<222> LOCATION: (7)..(8)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (9)..(9)
<223> OTHER INFORMATION: deoxyribonucleotide
<220> FEATURE:
<221> NAME/KEY: misc_feature
<222> LOCATION: (10)..(15)
<223> OTHER INFORMATION: ribonucleotide
<220> FEATURE:
<221> NAME/KEY: misc_feature
<222> LOCATION: (10)..(10)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (11)..(11)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (12)..(12)
<223> OTHER INFORMATION: Nucleotide is non-modified or
      phosphorothioated.
<220> FEATURE:
<221> NAME/KEY: misc_feature
<222> LOCATION: (13)..(14)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (15)..(15)
<223> OTHER INFORMATION: Nucleotide is non-modified or
      phosphorothioated.
<220> FEATURE:
<221> NAME/KEY: misc_feature
<222> LOCATION: (16)..(16)
<223> OTHER INFORMATION: ribonucleotide or deoxyribonucleotide
<220> FEATURE:
<221> NAME/KEY: misc_feature
<222> LOCATION: (16)..(16)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (17)..(19)
<223> OTHER INFORMATION: ribonucleotide
<220> FEATURE:
```

```
<221> NAME/KEY: misc_feature
<222> LOCATION: (17)..(17)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (18)..(18)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (19)..(19)
<223> OTHER INFORMATION: Nucleotide is non-modified or
      phosphorothioated, or when the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (20)..(20)
<223> OTHER INFORMATION: ribonucleotide or deoxyribonucleotide
<220> FEATURE:
<221> NAME/KEY: misc_feature
<222> LOCATION: (20)..(20)
<223> OTHER INFORMATION: When the nucleotide is a ribonucleotide, a
      hydroxyl group at the 2'-position of ribose therein is substituted
      by a fluorine atom.
<220> FEATURE:
<221> NAME/KEY: misc_feature
<222> LOCATION: (21)..(27)
<223> OTHER INFORMATION: ribonucleotide
<220> FEATURE:
<221> NAME/KEY: misc_feature
<222> LOCATION: (21)..(21)
<223> OTHER INFORMATION: The base is adenine or guanine.
<220> FEATURE:
<221> NAME/KEY: misc_feature
<222> LOCATION: (21)..(22)
<223> OTHER INFORMATION: Nucleotide is non-modified, or when the
      nucleotide is a ribonucleotide, a hydroxyl group at the 2'-
      position of ribose therein is substituted by an O-methyl group.
<220> FEATURE:
<221> NAME/KEY: misc_feature
<222> LOCATION: (23)..(26)
<223> OTHER INFORMATION: When the nucleotide is a ribonucleotide, a
      hydroxyl group at the 2'-position of ribose therein is substituted
      by an O-methyl group.
<220> FEATURE:
<221> NAME/KEY: misc_feature
<222> LOCATION: (27)..(27)
<223> OTHER INFORMATION: When nucleotide is a ribonucleotide, a hydroxyl
      group at the 2'-position of ribose therein is substituted by a
      fluorine atom or an O-methyl group.
<220> FEATURE:
<221> NAME/KEY: misc_feature
<222> LOCATION: (28)..(31)
<223> OTHER INFORMATION: ribonucleotide or deoxyribonucleotide
<220> FEATURE:
<221> NAME/KEY: misc_feature
<222> LOCATION: (28)..(31)
<223> OTHER INFORMATION: When the nucleotide is a ribonucleotide, a
      hydroxyl group at the 2'-position of ribose therein is substituted
      by an O-methyl group.

<400> SEQUENCE: 114
ggguagccgg aggagncagn raucgguacc c                                       31
```

ANTI-IL-17 APTAMER HAVING IMPROVED RETENTION IN BLOOD

SEQUENCE LISTING

The instant application contains a Sequence Listing which has been submitted electronically in ASCII format and is hereby incorporated by reference in its entirety. Said ASCII copy, created on Nov. 12, 2018, is named P54660_SL.TXT and is 322,855 bytes in size.

TECHNICAL FIELD

The present invention relates to an aptamer against interleukin-17 (IL-17), a method of utilizing the same, and the like.

BACKGROUND ART

The present inventors previously successfully produced an anti-IL-17 aptamer having an extremely high quality and a remarkably high inhibitory activity against binding between IL-17 and IL-17 receptor as compared to conventionally-known anti-IL-17 aptamers, and capable of inhibiting the physiological activity of IL-17, and disclosed same in patent document 1.

The active body of the aptamer is a nucleic acid. When the aptamer is administered as it is to a living organism, it is excreted from the kidney in several minutes and disappears from the blood. Thus, cholesterol and polyethylene glycol (PEG) and the like are added to delay excretion from the kidney and ensure blood retention property. PEG has many branches and it is also known that the blood retention property is improved as the molecular weight becomes larger (straight chain<2 branched<4 branched, 20 kDa<40 kDa<80 kDa). However, it is not sufficiently satisfactory (patent documents 2, 3). Moreover, there is a problem that the cost increases in proportion to the number of branches and the molecular weight of PEG, and PEG that can be actually used is limited. While there are reports on the improvement of blood retention property by adding PEG to each terminal by adding a functional group branched into two in advance to the nucleic acid (patent document 4) or utilizing a dendric structure (patent document 5), no specific data relating to the nucleic acid part is available. In the case of nucleic acid, it is known that the activity may be attenuated by the addition of PEG.

DOCUMENT LIST

Patent Documents patent document 1: WO 2014/148638
patent document 2: WO 2006/029258
patent document 3: US 20030114647
patent document 4: WO 2008/048079
patent document 5: National Publication of International Patent Application No. 2009-517414

SUMMARY OF THE INVENTION

Problems to be Solved by the Invention

The present invention aims to provide an anti-IL-17 aptamer having improved blood retention property in the body, which is the largest problem for the aptamer pharmaceutical products.

Means of Solving the Problems

In patent document 1, structural optimization in anti-IL-17 aptamer by enhancing binding activity and enhancing resistance to nucleic acid degrading enzyme (nuclease) in blood were studied. For administration to living organisms such as mouse and human, it is necessary to improve blood retention property by delaying excretion from the kidney by adding PEG or the like having a large molecular weight. However, half-life in blood, which is an index of blood retention property when 2 to 4 branched 40 kDa PEG in a known technique is used, is about 7 hr, and improvement is desired.

The present inventors have conducted intensive studies and found that unexpectedly higher blood retention property can be ensured by newly introducing a "branched structure" into the anti-IL-17 aptamer by a brancher and binding a 40 kDa PEG to each terminal via this portion to make the total 80 kDa, rather than directly attaching a 80 kDa PEG. The present inventors have also found that even if a branched structure is introduced, the blood retention property is not improved when the PEG added is linear, and the PEG itself needs to be branched. The present inventors conducted further studies based on these findings and completed the present invention.

Accordingly, the present invention is as described below.
[1] A compound represented by the following formula (I):

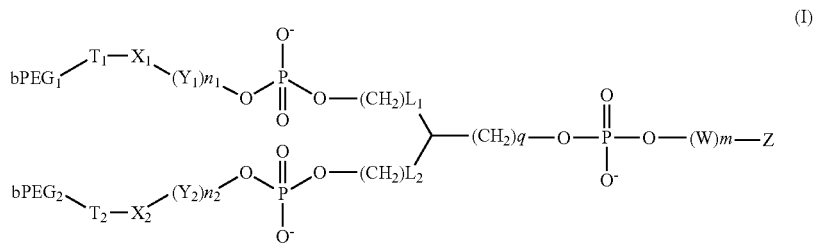

wherein m is 0 or 1, $n_1$ and $n_2$ are the same or different and each is 0 or 1, $L_1$ and $L_2$ are the same or different and each is an integer of 1-6, q is an integer of 0-6, $T_1$ and $T_2$ are the same or different and each is —C(O)—NH—, or

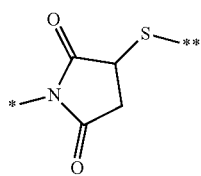

(* shows the bonding position of $bPEG_1$ or $bPEG_2$, ** shows the bonding position of $X_1$ or $X_2$), $X_1$ and $X_2$ are the same or different and each is $-(CH_2)_3-$, $-(CH_2)_6-$, $-(CH_2)_2OC(=O)NH(CH_2)_6-$, $-(CH_2)_2NHC(=O)O(CH_2)_6-$, or $-(CH_2)_2-[O(CH_2)_2]_g-$ (wherein g is an integer of 2-5), $Y_1$ and $Y_2$ are the same or different and each is $-OP(=O)(O^-)O(CH_2)_3-$, $-OP(=O)(O^-)O(CH_2)_6-$, $-OP(=O)(O^-)O(CH_2)_{12}-$, or $-OP(=O)(O^-)-[O(CH_2)_2]_j-$ (wherein j is an integer of 2-6), W is $-(CH_2)_3OP(=O)(O^-)O-$, $-(CH_2)_6OP(=O)(O^-)O-$, $-(CH_2)_{12}OP(=O)(O^-)O-$, or $-[O(CH_2)_2]_j-OP(=O)(O^-)-$ (wherein j is an integer of 2-6), $bPEG_1$ and $bPEG_2$ are the same or different and each is 10-80 kDa polyethylene glycol having a branched chain, Z is an aptamer comprising a sequence represented by the following formula (Ia):

```
                                          (SEQ ID NO: 105)
g(M)g(M)g(M)u(M)a'(M)g'(X1)c(M)c(M)g'g(M)a'(X4)

g(X5)g(M)a(M)g(X5)u'(F)c(X7)a'(X2)g(X6)u'(F)r(X3)

a'(X3)u(M)c(M)g(M)g(M)u'(X7)a'(M)c'(M)c'(M)c'(M)
``` or the following formula (Ib):

```
                                          (SEQ ID NO: 106)
g(M)g(M)u(M)a'(M)g'(X1)c(M)c(M)g'g(M)a'(X4)

g(X5)g(M)a(M)g(X5)u'(F)c(X7)a'(X2)g(X6)u'(F)r(X3)

a'(X3)u(M)c(M)g(M)g(M)u'(X7)a'(M)c'(M)c'(M)c'(M)
``` or the following formula (Ic):

```
                                          (SEQ ID NO: 107)
g(M)u(M)a'(M)g'(X1)c(M)c(M)g'g(M)a'(X4)g(X5)g(M)a (M)g(X5)u'(F)c(X7)a'(X2)g(X6)u'(F)r(X3)a'(X3)u(M)c (M)g(M)g(M)u'(X7)a'(M)c'(M)
``` or the following formula (Id):

```
                                          (SEQ ID NO: 108)
u(M)a'(M)g'(X1)c(M)c(M)g'g(M)a'(X4)g(X5)g(M)a(M)g (X5)u'(F)c(X7)a'(X2)g(X6)u'(F)r(X3)a'(X3)u(M)c(M)g (M)g(M)u'(X7)a'(M)
```

{in the above-mentioned formulas (Ia), (Ib), (Ic) and (Id),
a, g, c and u are each a ribonucleotide wherein the base is adenine, guanine, cytosine and uracil, respectively,
r is a ribonucleotide wherein the base is adenine or guanine,
a', g' and c' are each a ribonucleotide or deoxyribonucleotide wherein the base is adenine, guanine and cytosine, respectively,
u' is a ribonucleotide wherein the base is uracil, a deoxyribonucleotide wherein the base is uracil or a deoxyribonucleotide wherein the base is thymine, parentheses in nucleotide indicate modification of the nucleotide, (M) indicates that, when the nucleotide is a ribonucleotide, a hydroxyl group at the 2'-position of ribose therein is substituted by an O-methyl group, (F) indicates that, when the nucleotide is a ribonucleotide, a hydroxyl group at the 2'-position of ribose therein is substituted by a fluorine atom, ($X_1$) indicates that nucleotide is unmodified or phosphorothioated, or when the nucleotide is a ribonucleotide, a hydroxyl group at the 2'-position of ribose therein is substituted by a fluorine atom, ($X_2$) indicates that nucleotide is unmodified, or when the nucleotide is a ribonucleotide, a hydroxyl group at the 2'-position of ribose therein is substituted by a fluorine atom, ($X_3$) indicates that nucleotide is unmodified, or when the nucleotide is a ribonucleotide, a hydroxyl group at the 2'-position of ribose therein is substituted by an O-methyl group, ($X_4$) indicates that nucleotide is unmodified, or when the nucleotide is a ribonucleotide, a hydroxyl group at the 2'-position of ribose therein is substituted by a fluorine atom or an O-methyl group, ($X_5$) indicates that nucleotide is unmodified or phosphorothioated, ($X_6$) indicates that nucleotide is unmodified or phosphorothioated, or when the nucleotide is a ribonucleotide, a hydroxyl group at the 2'-position of ribose therein is substituted by an O-methyl group, and ($X_7$) indicates that when nucleotide is a ribonucleotide, a hydroxyl group at the 2'-position of ribose therein is substituted by a fluorine atom or an O-methyl group,} or the following formula (IIa):

```
g(x1)g(x1)g(x1)u(F)ag(S)c(F)c(F)g'(S)g(x2)aggagu(F)
    c(F)agu(F)aau(F)c(F)ggu(F)ac'(x3)c'(x3)c'(x(SEQ ID NO: 109)
``` or the following formula (IIb):

```
                                          (SEQ ID NO: 110)
g(x1)g(x1)u(F)ag(S)c(F)c(F)g'(S)g (x2)aggagu(F)c(F)agu(F)aau(F)c(F)

ggu(F)ac'(x3)c'(x3)
``` or the following formula (IIc):

```
                                          (SEQ ID NO: 111)
g(x1)u(F)ag(S)c(F)c(F)g'(S)g(x2)agg agu(F)c(F)agu(F)aau(F)c(F)ggu(F)

ac'(x3)
```

{in the above-mentioned formulas (IIa), (IIb) and (IIc),
(S) indicates that, when nucleotide is a ribonucleotide, it is phosphorothioated, ($x_1$) indicates that nucleotide is Locked Nucleic Acid (LNA)-modified, or when the nucleotide is a ribonucleotide, a hydroxyl group at the 2'-position of ribose therein is substituted by an O-methyl group, ($x_2$) indicates that nucleotide is unmodified, or when the nucleotide is a ribonucleotide, a hydroxyl group at the 2'-position of ribose therein is substituted by an O-methyl group, ($x_3$) indicates that nucleotide is unmodified, or LNA-modified, and other symbols are as defined above}, or a pharmaceutically acceptable salt, solvate or hydrate thereof.

[2] The compound of the above-mentioned [1], wherein
m is 0,
$n_1$ and $n_2$ are each, 0 or 1,
$L_1$ and $L_2$ are each 1,
q is 0,
$T_1$ and $T_2$ are the same or different and each is —C(O)—NH—, or,

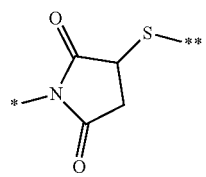

(* shows the bonding position of $bPEG_1$ or $bPEG_2$, ** shows the bonding position of $X_1$ or $X_2$),
$X_1$ and $X_2$ are the same and —$(CH_2)_6$—, —$(CH_2)_2OC(=O)NH(CH_2)_6$—, —$(CH_2)_2NHC(=O)O(CH_2)_6$—, or —$(CH_2)_2$—$[O(CH_2)_2]_3$—, and
$Y_1$ and $Y_2$ are each —OP(=O)(O⁻)O$(CH_2)_3$—, —OP(=O)(O⁻)O$(CH_2)_6$—, —OP(=O)(O⁻)O$(CH_2)_{12}$—, or —OP(=O)(O⁻)—$[O(CH_2)_2]_3$—,
or a pharmaceutically acceptable salt, solvate or hydrate thereof.

[3] The compound of the above-mentioned [1], wherein
m is 0,
$n_1$ and $n_2$ are each 0 or 1,
$L_1$ and $L_2$ are each 1,
q is 0,
$T_1$ and $T_2$ are each —C(O)—NH—,
$X_1$ and $X_2$ are each —$(CH_2)_6$—, —$(CH_2)_2OC(=O)NH(CH_2)_6$—, —$(CH_2)_2NHC(=O)O(CH_2)_6$—, or —$(CH_2)_2$—$[O(CH_2)_2]_3$—, and
$Y_1$ and $Y_2$ are each —OP(=O)(O⁻)O$(CH_2)_3$—, —OP(=O)(O⁻)O$(CH_2)_6$—, —OP(=O)(O⁻)O$(CH_2)_{12}$—, or —OP(=O)(O⁻)—$[O(CH_2)_2]_3$—,
or a pharmaceutically acceptable salt, solvate or hydrate thereof.

[4] The compound of the above-mentioned [1], wherein
m is 0,
$n_1$ and $n_2$ are each 1,
$L_1$ and $L_2$ are each 1,
q is 0,
$T_1$ and $T_2$ are each —C(O)—NH—,
$X_1$ and $X_2$ are each —$(CH_2)_6$—, or —$(CH_2)_2OC(=O)NH(CH_2)_6$—, and
$Y_1$ and $Y_2$ are each —OP(=O)(O⁻)—$[O(CH_2)_2]_3$—,
or a pharmaceutically acceptable salt, solvate or hydrate thereof.

[5] The compound of the above-mentioned [1], wherein
m is 0,
$n_1$ and $n_2$ are each 0,
$L_1$ and $L_2$ are each 1,
q is 0, and
$T_1$ and $T_2$ are each —C(O)—NH—,
$X_1$ and $X_2$ are each —$(CH_2)_6$—, —$(CH_2)_2OC(=O)NH(CH_2)_6$—, or —$(CH_2)_2$—$[O(CH_2)_2]_3$—,
or a pharmaceutically acceptable salt, solvate or hydrate thereof.

[6] The compound of any of the above-mentioned [1]-[5], wherein Z is an aptamer comprising a sequence shown in any of SEQ ID NO: 1-104, or a pharmaceutically acceptable salt, solvate or hydrate thereof.

[7] The compound of any of the above-mentioned [1]-[6], wherein $bPEG_1$ and $bPEG_2$ are each 15-45 kDa polyethylene glycol having a branched chain, and
Z is an aptamer comprising a sequence shown in any of SEQ ID NO: 1-104, or a pharmaceutically acceptable salt, solvate or hydrate thereof.

[8] The compound of any of the above-mentioned [1]-[7], wherein $bPEG_1$ and $bPEG_2$ are each 35-45 kDa polyethylene glycol having a branched chain, or a pharmaceutically acceptable salt, solvate or hydrate thereof.

[9] A medicament comprising the compound of any of the above-mentioned [1]-[8], or a pharmaceutically acceptable salt, solvate or hydrate thereof.

[10] The medicament of the above-mentioned [9] for use in the treatment or prophylaxis relating to inflammatory disease, autoimmune disease, cancer, allergy, or infection.

Effect of the Invention

According to the present invention, an anti-IL-17 aptamer having improved blood retention property in vivo is provided. The aptamer of the present invention can drastically extend the half-life in blood from the conventional limit of about 10-20 hr to, for example, about 100 hr in monkey, while retaining the binding activity to IL-17 and maintaining efficacy for diseases in animals. Therefore, therapeutic possibility for diseases such as psoriasis and the like by systemic administration of an aptamer having the structure can be provided.

BRIEF DESCRIPTION OF THE DRAWINGS

FIG. 1 shows the structures of the aptamers used in Examples. In the Figure, the nucleic acids in the oligomer part are the sequences shown in Example sequences 1-4.

FIG. 2-1 shows the outline of the synthesis procedure of the aptamer in Example.

FIG. 2-2 shows the MALDI-TOF-MS analysis results of PEGylated oligonucleotide of Example sequence 4 as a confirmation example of the final product of aptamer synthesis in Example.

DESCRIPTION OF EMBODIMENTS

Figure 2:
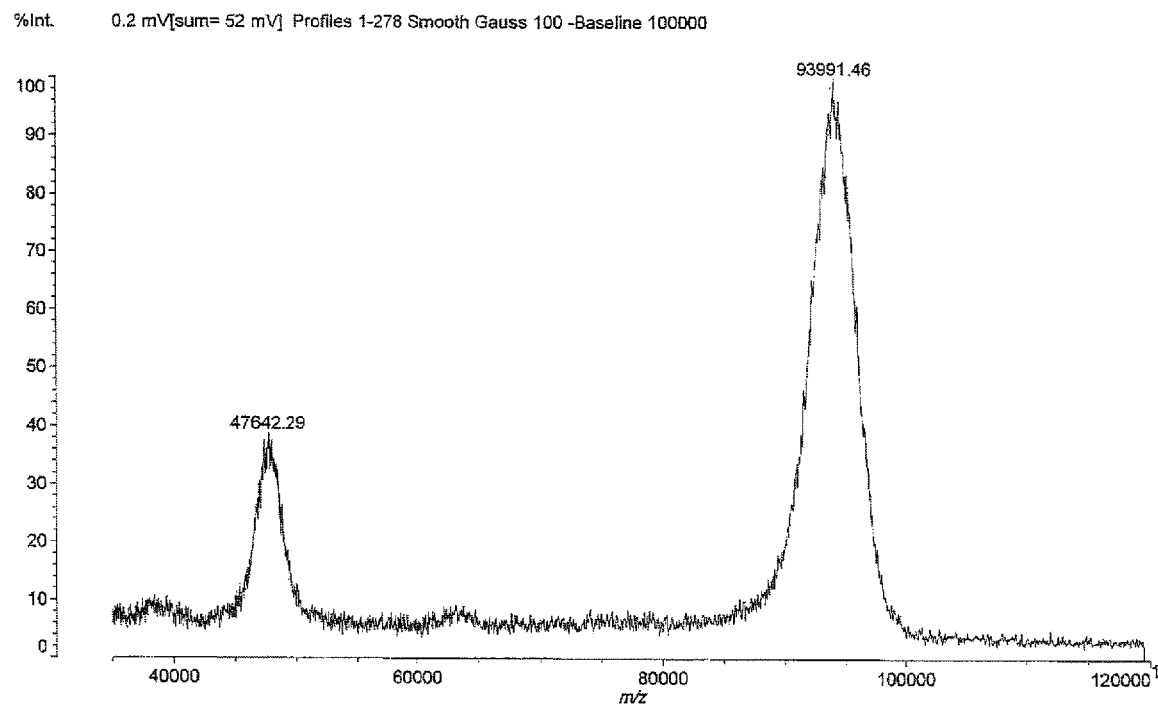

The present invention provides a compound represented by the following formula (I):

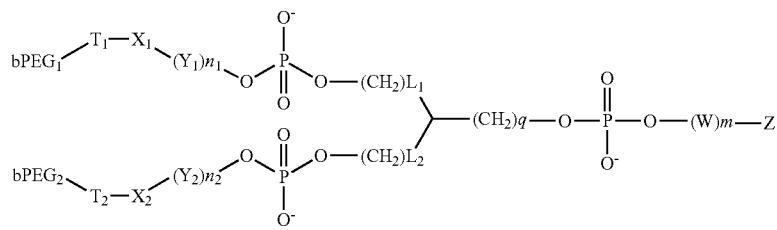

(wherein each symbol is as defined below) or a pharmaceutically acceptable salt, solvate or hydrate thereof (hereinafter these are also generically referred to as the compound of the present invention).

In the formula (I), m is 0 or 1.

$n_1$ and $n_2$ are the same or different and each is 0 or 1. Preferably, both $n_1$ and $n_2$ are each 0 or 1, more preferably, both $n_1$ and $n_2$ are each 1 from the aspect of PEGylation yield during synthesis.

$T_1$ and $T_2$ are the same or different and each is —C(O)—NH—, or

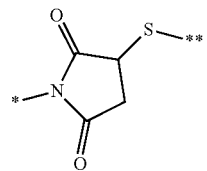

(* shows the bonding position of $bPEG_1$ or $bPEG_2$ and ** shows the bonding position of $X_1$ or $X_2$). $T_1$ and $T_2$ are preferably the same, more preferably both —C(O)—NH—.

$X_1$ and $X_2$ are the same or different and each is —(CH$_2$)$_3$—, —(CH$_2$)$_6$—, —(CH$_2$)$_2$OC(=O)NH(CH$_2$)$_6$—, —(CH$_2$)$_2$NHC(=O)O(CH$_2$)$_6$—, or —(CH$_2$)$_2$—[O(CH$_2$)$_2$]$_g$— (wherein g is an integer of 2-5). Preferably, $X_1$ and $X_2$ are the same.

$Y_1$ and $Y_2$ are the same or different and each is —OP(=O)(O$^-$)O(CH$_2$)$_3$—, —OP(=O)(O$^-$)O(CH$_2$)$_6$—, —OP(=O)(O$^-$)O(CH$_2$)$_{12}$—, or —OP(=O)(O$^-$)—[O(CH$_2$)$_2$]$_j$— (wherein j is an integer of 2-6). Preferably, $Y_1$ and $Y_2$ are the same.

W is —(CH$_2$)$_3$OP(=O)(O$^-$)O—, —(CH$_2$)$_6$OP(=O)(O$^-$)O—, —(CH$_2$)$_{12}$OP(=O)(O$^-$)O—, or —[O(CH$_2$)$_2$]$_j$—OP(=O)(O$^-$)— (wherein j is an integer of 2-6).

As mentioned above, in the compound of the present invention, a branched structure (branch structure) is imparted by a brancher, and therefore, two PEG chains can be added to the aptamer. The brancher may have a structure shown by the following formula.

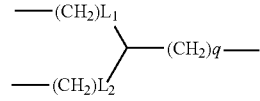

As used herein, $L_1$ and $L_2$ are the same or different and each is an integer of 1-6. Preferably, $L_1$ and $L_2$ are the same.

q is an integer of 0-6.

As shown in the above-mentioned formula (I), the compound of the present invention contains, in addition to an aptamer structure (Z in the formula (I)), a linker ($X_1$, $X_2$ in the formula (I)) and, optionally, a spacer ($Y_1$, $Y_2$, W in the formula (I)).

In one embodiment, in the above-mentioned formula (I), both $T_1$ and $T_2$ are —C(O)—NH—, $X_1$ and $X_2$ are the same or different and each is —(CH$_2$)$_3$—, —(CH$_2$)$_6$—, —(CH$_2$)$_2$OC(=O)NH(CH$_2$)$_6$—, or —(CH$_2$)(CH$_2$)$_2$—[O(CH$_2$)$_2$]$_g$— (wherein g is an integer of 2-5), and Z is an aptamer containing a sequence represented by the formula (Ia) or the formula (IIa). In the embodiment, for example, (1) m is 0, both $n_1$ and $n_2$ are each 1, $L_1$ and $L_2$ are each 1, q is 0, $X_1$ and $X_2$ are the same, —(CH$_2$)$_6$—, —(CH$_2$)$_2$OC(=O)NH(CH$_2$)$_6$—, or —(CH$_2$)$_2$—[O(CH$_2$)$_2$]$_3$—, and $Y_1$ and $Y_2$ are each —OP(=O)(O$^-$)—[O(CH$_2$)$_2$]$_3$—, or, (2) m is 0, $n_1$ and $n_2$ are each 0, $L_1$ and $L_2$ are each 1, q is 0, and $X_1$ and $X_2$ are the same, —(CH$_2$)$_6$—, —(CH$_2$)$_2$OC(=O)NH(CH$_2$)$_6$—, or —(CH$_2$)$_2$—[O(CH$_2$)$_2$]$_3$—.

In a preferable embodiment, m is 0, $n_1$ and $n_2$ are each 0 or 1, $L_1$ and $L_2$ are each 1, q is 0, $T_1$ and $T_2$ are each —C(O)—NH—, $X_1$ and $X_2$ are each —(CH$_2$)$_6$—, —(CH$_2$)$_2$ OC(=O)NH(CH$_2$)$_6$—, —(CH$_2$)$_2$NHC(=O)O(CH$_2$)$_6$—, or —(CH$_2$)$_2$—[O(CH$_2$)$_2$]$_3$—, and Y$_1$ and Y$_2$ are each —OP(=O)(O$^-$)—[O(CH$_2$)$_2$]$_3$—. In another preferable embodiment, m is 0, n$_1$ and n$_2$ are each 0, L$_1$ and L$_2$ are each 1, q is 0, T$_1$ and T$_2$ are each —C(O)—NH—, and X$_1$ and X$_2$ are each —(CH$_2$)$_6$—, —(CH$_2$)$_2$OC(=O)NH(CH$_2$)$_6$—, —(CH$_2$)$_2$NHC(=O)O(CH$_2$)$_6$—, or —(CH$_2$)$_2$—[O(CH$_2$)$_2$]$_3$—.

bPEG$_1$ and bPEG$_2$ are the same or different and each is 10-80 kDa polyethylene glycol having a branched chain (branched PEG, bPEG). The species of branching of PEG may be any and may be, for example, conventional 2-branched chain type, 3-branched chain type, 4-branched chain type or the like.

PEG is preferably PEG of 10-80 kDa having a branched chain, more preferably PEG of 15-45 kDa having a branched chain, furthermore preferably PEG of 35-45 kDa (e.g., about 40 kDa) having a branched chain.

As such PEG, those of ordinary skill in the art can appropriately select and use commercially available or known PEG (see, e.g., http://www.peg-drug.com/peg product/branched.html). Specific preferable examples of PEG to be applied to the aptamer of the present invention include 2-branched GS type PEG having a molecular weight of 40000 (SUNBRIGHT GL2-400GS2 manufactured by NOF CORPORATION), 2-branched TS type PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), 4-branched TS type PEG having a molecular weight of 80000 (SUNBRIGHT GL4-800TS manufactured by NOF CORPORATION), Y-shape 40 kDa PEG having a molecular weight of 40000 and branched into 2 chains by an amide structure (manufactured by JenKem), and the like.

Z is an aptamer containing a sequence represented by the following formula (Ia):

(SEQ ID NO: 105)
g(M)g(M)g(M)u(M)a'(M)g'(X$_1$)c(M)c(M)

g'g(M)a'(X$_4$)g(X$_5$)g(M)a(M)g(X$_5$)u'(F)

c(X$_7$)a'(X$_2$)g(X$_6$)u'(F)r(X$_3$)a'(X$_3$)u (M)c(M)g(M)g(M)u'(X$_7$)a'(M)c'(M)c'

(M)c'(M)

or the following formula (Ib):

SEQ ID NO: 106
g(M)g(M)u(M)a'(M)g'(X$_1$)c(M)c(M)g'g (M)a'(X$_4$)g(X$_5$)g(M)a(M)g(X$_5$)u'(F)c (X$_7$)a'(X$_2$)g(X$_6$)u'(F)r(X$_3$)a'(X$_3$)u(M)

c(M)g(M)g(M)u'(X$_7$)a'(M)c'(M)c'(M)

or the following formula (Ic):

(SEQ ID NO: 107)
g(M)u(M)a'(M)g'(X$_1$)c(M)c(M)g'g(M)a'(X$_4$)g(X$_5$)g(M)a (M)g(X$_5$)u'(F)c(X$_7$)a'(X$_2$)g(X$_6$)u'(F)r(X$_3$)a'(X$_3$)u(M)

c(M)g(M)g(M)u'(X$_7$)af(M)c'(M)

or the following formula (Id):

(SEQ ID NO: 108)
u(M)a'(M)g'(X$_1$)c(M)c(M)g'g(M)a'(X$_4$)g(X$_5$)g(M)a(M)g (X$_5$)u'(F)c(X$_7$)a'(X$_2$)g(X$_6$)u'(F)r(X$_3$)a'(X$_3$)u(M)c (M)g(M)g(M)u'(X$_7$)a'(M)

or the following formula (IIa):

(SEQ ID NO: 109)
g(x$_1$)g(x$_1$)g(x$_1$)u(F)ag(S)c(F)c(F)g'(S)g(x$_2$)aggagu (F)c(F)agu(F)aau(F)c(F)ggu(F)ac'(x$_3$)c'(x$_3$)c'(x$_3$)

or the following formula (IIb):

(SEQ ID NO: 110)
g(x$_1$)g(x$_1$)u(F)ag(S)c(F)c(F)g'(S)g(x$_2$)aggagu(F)c(F)

agu(F)aau(F)c(F)ggu(F)ac'(x$_3$)c'(x$_3$)

or the following formula (IIc):

(SEQ ID NO: 111)
g(x$_1$)u(F)ag(S)c(F)c(F)g'(S)g(x$_2$)aggagu(F)c(F)agu (F)aau(F)c(F)ggu(F)ac'(x$_3$)

(wherein the symbols are as mentioned above).

In a preferable embodiment, Z is an aptamer containing a sequence represented by the following formula (Ia'):

(SEQ ID NO: 112)
g(M)g(M)g(M)u(M)a'(M)g(X$_5$)c(M)c(M)Gg(M)a(X$_4$)gg(M)a (M)g(X$_5$)u'(F)c(X$_7$)a(X$_2$)g(X$_5$)ur(F)r(X$_3$)a(X$_3$)u(M)c (M)g(M)g(M)u(X$_7$)a(M)c'(M)c'(M)c'(M)

wherein a, g, c, u and r, a', c' and u', and (M), (F) and (X$_2$)-(X$_5$) and (X$_7$) as defined for the formula (Ia), and G is a deoxyribonucleotide having guanine as a base.

In a preferable embodiment, moreover, Z is an aptamer containing a sequence represented by the following formula (Ia'''):

(SEQ ID NO: 113)
g(M)g(M)g(M)u(M)a'(M)g'(X$_1$)c(M)c(M)g'g(M)a'(X$_2$)gg (M)a(M)gu'(F)c(F)a'(X$_2$)gu'(F)a(X$_3$)a'(X$_3$)u(M)c(M)g (N)g(M)u'(F)a'(M)cr(M)c'(M)c'(M)

wherein a, g, c and u, a', g', c' and u', and (M), (F) and (X$_1$)-(X$_3$) are as defined for the formula (Ia).

In a preferable embodiment, Z is an aptamer containing a sequence represented by the following formula (Ia''):

(SEQ ID NO: 114)
g(M)g(M)g(M)u(M)a'(M)g(X$_5$)c(M)c(M)Gg(M)a(X$_7$)g(X$_5$)

g(M)a(M)g(X$_5$)u'(F)c(X$_7$)a(F)g(X$_5$)u'(F)r(X$_3$)a(X$_3$)u (M)c(M)g(M)g(M)u(X$_7$)a'(M)c'(M)c'(M)c'(M)

wherein a, g, c, u and r, a', c' and u', and (M), (F), (X$_3$) and (X$_5$)-(X$_7$) are as defined for the formula (Ia), and G is a deoxyribonucleotide having guanine as a base.

In a preferable embodiment, moreover, Z is an aptamer wherein, in the formula (Ia''), c'(M)c'(M)c'(M) on the 3'-terminal side is c(M)c(M)c(M).

An aptamer refers to a nucleic acid molecule having a binding activity for a particular target molecule. The aptamer can inhibit the activity of a particular target molecule by binding to the particular target molecule. In the present invention, the aptamer may be a ribonucleotide, a deoxyribonucleotide, a modified nucleic acid or a chimera thereof. The aptamer can also be in a linear or circular form.

In the present invention, the aptamer can bind to IL-17 to inhibit the binding between IL-17 and IL-17 receptor. IL-17 refers to a cytokine secreted by Th17 cells and the like, and is, for example, a protein having the amino acid sequence shown by Accession code AAH67505 or NP002181. IL-17 is sometimes called IL-17A or CTLA-8. In addition to being produced in animal bodies, IL-17 as used in the present invention can be produced by using mouse and other mammalian cells, insect cells, cells of *Escherichia coli* and the like, and can also be prepared by chemical synthesis. When IL-17 is prepared by cell culture or chemical synthesis, a variant can easily be prepared. Here, a variant means a sequence wherein several amino acids have been substituted or a partial amino acid sequence, and means a protein or peptide having at least one or more of the activities essentially possessed by IL-17. When an amino acid is substituted, the substituent amino acid may be a naturally occurring amino acid, or may be a non-naturally occurring amino acid. As mentioned in the present invention, IL-17 includes these variants.

An IL-17 receptor means a cell surface protein to which IL-17 binds and a protein that mediates intracellular signaling. As members of the IL-17 receptor family, IL-17RA, IL-17RB, IL-17RC, IL-17RD, and IL-17RE are known. As mentioned in the present invention, the IL-17 receptor may be a protein comprising a naturally occurring amino acid sequence, or may be a variant thereof. Here, a variant means a sequence wherein several amino acids have been substituted or a partial amino acid sequence, and means a protein or peptide possessing binding activity for IL-17. The compound of the present invention can inhibit the binding between IL-17 and IL-17 receptor. The binding inhibitory activity can be measured by a method known per se such as Biacore test and the like (see, e.g., WO 2014/148638).

In a preferable embodiment, the aptamer, accordingly, the compound of the present invention, binds to IL-17 to inhibit the binding between IL-17 and IL-17 receptor, whereby it can inhibit a signaling activity of IL-17 derived from any mammal. Examples of the mammal include primates (e.g., humans, monkeys), rodents (e.g., mice, rats, guinea pigs), and companion animals, domestic animals and work animals (e.g., dogs, cats, horses, cattles, goats, sheep, pigs).

Inhibition of IL-17 signaling activity means an inhibitory capacity against any signaling activity that IL-17 has. For example, IL-17 is known to bind to IL-17 receptor, and activates NF-κB pathway and MAP kinase pathway via TRAF6 and the like, and then production of various cytokines and chemokines is induced via such signal transduction pathways. Therefore, the IL-17 signaling inhibitory activity refers to an activity that inhibits the production of these cytokines, chemokines and the like, which are present at the downstream of the IL-17 signal transduction pathway. Since the expression of these cytokines and chemokines induces the migration and activation of inflammatory cells, signaling inhibitory activity against IL-17 also means inhibition of such activities.

The IL-17 signaling inhibitory activity can be evaluated by, for example, the following test.

In a test using cultured cells, the amount of IL-6 released by the stimulation of IL-17 and TNF to cells in cultured cells is measured.

Human IL-17 and each aptamer are pre-incubated at 37° C. for 30 min, and added to NIH3T3 cells with mouse TNFα. Then, after incubation for 24 hr, the culture supernatant is collected, the amount of produced IL-6 is measured by ELISA method and IC$_{50}$ is calculated.

In a test using a mouse air pouch inflammation model, the measurement is performed as follows.

Air (2.5 mL) is subcutaneously injected into the back of male mouse of C57BL/6J mouse every two days, and aptamer is intraperitoneally administered 3 days later. One hour later, 2% aqueous carbomethylcellulose solution containing IL-17 (0.5 μg) is administered in air pouch. After 24 hr, the exudate in the air pouch is collected and the amount of IL-6 in the exudate is measured by ELISA (e.g., Biochemical Pharmacology 77, 878-887 2009).

In a test using collagen arthritis model in mice, the measurement is performed as follows.

Bovine type II collagen emulsified with complete adjuvant is intradermally administered into the tail base of male DBA/1 mouse and, 22 days later, booster immunization with bovine type II collagen emulsified with incomplete adjuvant is performed, along with which aptamer is intraperitoneally administered once every two days. The animal is observed every day, the inflammation of each limb was scored in 5 levels from 0 (no symptom) to 4 (redness of whole limb and maximum swelling), and the efficacy of the aptamer of the present invention on arthritis is evaluated (e.g., Arthritis Res Ther 12, R92 (2010)).

A lower numerical value is judged to mean strong inhibition of IL-17 signaling activity by the aptamer.

In the present specification, nucleotide being unmodified means that a hydroxyl group at the 2'-position of ribose in a ribonucleotide, or hydrogen at the 2'-position of ribose in a deoxyribonucleotide is not substituted by other element, and nucleotide being modified means, for example, that a hydroxyl group at the 2'-position of ribose in a ribonucleotide is substituted by a fluorine atom or an O-methyl group, nucleotide is phosphorothioated, Locked Nucleic Acid (LNA)-modified and the like. The "nucleotide is phosphorothioated" means that a phosphate group in a binding site between adjacent nucleotides is sulfurated, that is, a phosphodiester bond is converted to a phosphorothioate bond, and being LNA-modified means that an oxygen atom at the 2'-position and a carbon atom at the 4'-position of ribose in a nucleotide are methylene crosslinked.

Various modifications shown by the formulas (Ia)-(Id), (Ia'), (Ia'''), (Ia'') and (IIa)-(IIc) can be performed according to a method known per se (see, e.g., Sproat et al., (1991), Nucl. Acid. Res. 19, 733-738; Cotton et al., (1991), Nucl. Acid. Res. 19, 2629-2635; Hobbs et al., (1973), Biochemistry 12, 5138-5145 and the like).

Z may also be an aptamer wherein a nucleotide having guanine or uracil as a base is added to the 5'-terminal, and/or a nucleotide having cytosine or adenine as a base is added to the 3'-terminal of a sequence represented by the above-mentioned formulas (Ia)-(Id), (Ia'), (Ia'''), (Ia'') or (IIa)-(IIc), and, when it is a ribonucleotide, a hydroxyl group at the 2'-position of ribose therein may be substituted by an O-methyl group.

Preferably, the aptamer may be an aptamer containing a sequence selected from any of aptamer No. 1-104 shown below, or a conjugate of a plurality of such aptamers as long as it binds to IL-17 and inhibits the binding between IL-17 and IL-17 receptor.

In the above-mentioned conjugate of a plurality of such aptamers, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$-linker, —(CH$_2$CH$_2$O)$_n$-linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described plural conjugates is not particularly limited, as long as it is two or more, and the plurality can be, for example, 2, 3 or 4.

In the tandem binding of the above-mentioned conjugate of a plurality of aptamers, a spacer may also be used to mainly elongate the aptamer length. As the spacer, a structure considered to be not directly involved in the binding activity of the aptamer is mostly used. Examples thereof include nucleotide chain (e.g., 1-about 20 nucleotides), and non-nucleotide chain (e.g., —OP(=O)(O$^-$)O(CH$_2$)$_3$-spacer, spacer containing other —OPO$_3$-bond etc.). The plurality as mentioned in the above-described conjugate of a plurality of aptamer is not particularly limited as long as it is, similar to the linker, two or more, and the plurality can be, for example, 2, 3 or 4.

The above-mentioned linker and spacer can be contained in the structure of the compound of the present invention, and are not limited to the tandem binding of conjugate of a plurality of aptamers.

The length of the aptamer is not particularly limited, and can usually be not more than about 200 nucleotides. When the total number of nucleotides is smaller, chemical synthesis and mass-production will be easier, and there is a more advantage in terms of cost. It is also considered that chemical modification is easier, and stability in the body is higher. Therefore, from the aspects of application to the use of a pharmaceutical product, the aptamer more desirably has a shorter base length than 70 nucleotides, preferably not more than about 50 nucleotides, more preferably not more than about 40 nucleotides (e.g., not more than 40 nucleotides, not more than 39 nucleotides, not more than 38 nucleotides, not more than 37 nucleotides, not more than 36 nucleotides), most preferably not more than about 35 nucleotides (e.g., not more than 35 nucleotides, not more than 34 nucleotides, not more than 33 nucleotides).

In the compound of the present invention, nucleic acid base may be further altered (e.g., chemical substitution) to enhance binding property to IL-17, inhibitory activity against binding between IL-17 and IL-17 receptor, stability, and the like. Such alteration includes that of 3'-terminus and/or 5'-terminus such as capping.

An alteration can further be performed by adding, to 3'-terminal and/or 5'-terminal of a polyethyleneglycol, amino acid, peptide, inverted dT, nucleic acid, nucleosides, polynucleotide, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin, various linkers and the like. For such alterations, see, for example, U.S. Pat. Nos. 5,660,985 and 5,756,703.

The linker, spacer and brancher for PEG and the aptamer are not particularly limited, and carbon chain number, functional group and the like can be appropriately selected according to the species of PEG and the like. Examples of such linker include a linker having an amino group, a linker having a sulfhydryl group. Specifically, TFA Amino C-6 lcaa CPG (ChemGenes), Thiol Modifier Hexyl CED Phosphoramidite (ChemGenes) and the like can be mentioned. When a linker having an amino group is selected, for example, an active group of N-hydroxysuccinimide is added to PEG, and reacted with an amino group on the linker side, whereby the aptamer can be bound to PEG via the linker. Alternatively, when a linker having a sulfhydryl group is selected, PEG and the linker can be easily bonded when an active group of Maleimide is added to PEG. Examples of the brancher include Synmmetrical-branching Phosphoramidite (ChemGenes) and the like.

As PEG, linker, spacer and brancher, commercially available products can be preferably used. The reaction conditions and the like relating to the binding of PEG, a linker, a spacer, a brancher and an aptamer can be appropriately determined by those of ordinary skill in the art.

A preferable specific aptamer for Z includes aptamer No. 1-104 containing the following sequence. In aptamer No. 1-104, preferably, idT (inverted deoxy thymidine) is added to the 3'-terminal. The head of each sequence is the 5'-terminal and the end is the 3'-terminal. a, g, c, u each show ribonucleotide wherein the base is adenine, guanine, cytosine or uracil, respectively, A, G, C, U, T each show deoxyribonucleotide wherein the base is adenine, guanine, cytosine, uracil and thymine, respectively, and mc is a ribonucleotide wherein the base is methylcytosine. Parentheses in nucleotide indicate modification of the nucleotide, (M) indicates that, when the nucleotide is a ribonucleotide, a hydroxyl group at the 2'-position of ribose therein is substituted by an O-methyl group, and (F) indicates that, when the nucleotide is a ribonucleotide, a hydroxyl group at the 2'-position of ribose therein is substituted by a fluorine atom. (S) indicates that nucleotide is phosphorothioated and (L) indicates that it is LNA-modified. For example, c(F) shows cytidine wherein a hydroxyl group at the 2'-position of ribose therein is substituted by a fluorine atom, a(M) shows adenosine wherein 2'-position of ribose is substituted by O-methyl group, and g(M) shows guanosine wherein the 2'-position of ribose therein is substituted by O-methyl group (hereinafter similarly described).

```
aptamer No. 1:
                                                     (SEQ ID NO: 1)
g(L)g(L)g(L)u(F)ag(S)c(F)c(F)g(S)gaggagu(F)c(F)agu(F)aau(F)c(F)

ggu(F)amc(L)mc(L)mc(L)

aptamer No. 2:
                                                     (SEQ ID NO: 2)
g(M)g(M)g(M)u(F)ag(S)c(F)c(F)Gg(M)aggagu(F)c(F)agu(F)aau(F)c(F)

ggu(F)aCCC
```

-continued aptamer No. 3:
(SEQ ID NO: 3)
g(M)g(M)g(M)u(M)a(M)gc(M)c(M)Gg(M)a(F)gg(M)a(M)gu(F)c(F)a(F)gu (F)a(M)a(M)u(M)c(M)g(M)g(M)u(F)ACCC aptamer No. 4:
(SEQ ID NO: 4)
g(M)g(M)g(M)u(M)Ag(S)c(M)c(M)Gg(M)a(F)gg(M)a(M)gu(F)c(F)a(F)gu (F)a(M)a(M)u(M)c(M)g(M)g(M)u(F)a(M)CCC aptamer No. 5:
(SEQ ID NO: 5)
g(M)g(M)g(M)g(M)u(M)a(M)g(S)c(M)c(M)Gg(M)a(F)gg(M)a(M)gTc(F)a (F)gTa(M)a(M)u(M)c(M)g(M)g(M)u(F)ACCCC aptamer No. 6:
(SEQ ID NO: 6)
g(M)g(M)g(M)u(M)a(M)g(S)c(M)c(M)Gg(M)Agg(M)a(M)gTc(F)a(F)gTa(M)

a(M)u(M)c(M)g(M)g(M)u(F)ACCC aptamer No. 7:
(SEQ ID NO: 7)
g(M)g(M)g(M)u(M)Ag(S)c(M)c(M)Gg(M)a(F)gg(M)a(M)gu(F)c(F)a(F)gu (F)aau(M)c(M)g(M)g(M)u(F)a(M)CCC aptamer No. 8 (Example sequence 1):
(SEQ ID NO: 8)
g(M)g(M)g(M)u(M)Ag(S)c(M)c(M)Gg(M)a(F)gg(M)a(M)gTc(F)a(F)gTaau (M)c(M)g(M)g(M)u(F)a(M)CCC aptamer No. 9:
(SEQ ID NO: 9)
g(M)g(M)g(M)u(M)Ag(S)c(M)c(M)Gg(M)a(F)gg(M)a(M)gTc(F)a(F)gTa(M)

a(M)u(M)c(M)g(M)g(M)u(F)a(M)CCC aptamer No. 10:
(SEQ ID NO: 10)
g(M)g(M)g(M)u(M)a(M)g(S)c(M)c(M)Gg(M)a(F)gg(M)a(M)gTc(F)a(F)gTa (M)Au(M)c(M)g(M)g(M)u(F)ACCC aptamer No. 11:
(SEQ ID NO: 11)
g(M)g(M)g(M)u(M)Ag(S)c(M)c(M)Gg(M)a(F)gg(M)a(M)gTc(F)a(F)gTa(M)

Au(M)c(M)g(M)g(M)u(F)a(M)CCC aptamer No. 12:
(SEQ ID NO: 12)
g(M)g(M)g(M)u(M)Agc(M)c(M)Gg(M)a(F)gg(M)a(M)gTc(F)a(F)gTa(M)a (M)u(M)c(M)g(M)g(M)u(F)a(M)CCC aptamer No. 13:
(SEQ ID NO: 13)
g(M)g(M)g(M)u(M)Agc(M)c(M)Gg(M)a(F)gg(M)a(M)gTc(F)a(F)gTa(M)Au (M)c(M)g(M)g(M)u(F)a(M)CCC aptamer No. 14:
(SEQ ID NO: 14)
g(M)g(M)g(M)u(M)Ag(F)c(M)c(M)Gg(M)a(F)gg(M)a(M)gTc(F)a(F)gTa(M)

a(M)u(M)c(M)g(M)g(M)u(F)a(M)CCC aptamer No. 15:
(SEQ ID NO: 15)
g(M)g(M)g(M)u(M)Ag(F)c(M)c(M)Gg(M)a(F)gg(M)a(M)gTc(F)a(F)gTa(M)

Au(M)c(M)g(M)g(M)u(F)a(M)CCC aptamer No. 16:

-continued (SEQ ID NO: 16)
g(M)g(M)g(M)g(M)u(M)Ag(S)c(M)c(M)Gg(M)a(F)gg(M)a(M)gTc(F)a(F)gT a(M)a(M)u(M)c(M)g(M)g(M)u(F)a(M)CCCC aptamer No. 17:
(SEQ ID NO: 17)
g(M)g(M)g(M)g(M)u(M)Ag(S)c(M)c(M)Gg(M)a(F)gg(M)a(M)gTc(F)a(F)gT a(M)Au(M)c(M)g(M)g(M)u(F)a(M)CCCC aptamer No. 18:
(SEQ ID NO: 18)
g(M)g(M)g(M)g(M)u(M)Ag(S)c(M)c(M)Gg(M)a(F)gg(M)a(M)gTc(F)a(F)gT aau(M)c(M)g(M)g(M)u(F)a(M)CCCC aptamer No. 19:
(SEQ ID NO: 19)
g(M)g(M)g(M)u(M)Ag(S)c(M)c(M)Gg(M)Agg(M)a(M)gTc(F)a(F)gTa(M)a (M)u(M)c(M)g(M)g(M)u(F)a(M)CCC aptamer No. 20:
(SEQ ID NO: 20)
g(M)g(M)g(M)u(M)Ag(S)c(M)c(M)Gg(M)Agg(M)a(M)gTc(F)a(F)gTa(M)Au (M)c(M)g(M)g(M)u(F)a(M)CCC aptamer No. 21:
(SEQ ID NO: 21)
g(M)g(M)g(M)u(M)Ag(S)c(M)c(M)gg(M)Agg(M)a(M)gTc(F)agTaau(M)c(M)

g(M)g(M)Ta(M)c(M)c(M)c(M)

aptamer No. 22:
(SEQ ID NO: 22)
g(M)g(M)g(M)u(M)Agc(M)c(M)gg(M)Agg(M)a(M)gTc(F)agTaau(M)c(M)g (M)g(M)Ta(M)c(M)c(M)c(M)

aptamer No. 23:
(SEQ ID NO: 23)
g(M)g(M)g(M)u(M)Ag(S)c(M)c(M)gg(M)Agg(M)a(M)gTc(F)agTaau(M)c(M)

g(M)g(M)TAc(M)c(M)c(M)

aptamer No. 24:
(SEQ ID NO: 24)
g(M)g(M)g(M)u(M)Agc(M)c(M)gg(M)Agg(M)a(M)gTc(F)agTaau(M)c(M)g (M)g(M)TAc(M)c(M)c(M)

aptamer No. 25:
(SEQ ID NO: 25)
g(M)g(M)g(M)u(M)Agc(M)c(M)gg(M)Agg(M)a(M)gTc(F)agTa(M)Au(M)c(M)

g(M)g(M)TAc(M)c(M)c(M)

aptamer No. 26:
(SEQ ID NO: 26)
g(M)g(M)g(M)u(M)Ag(S)c(M)c(M)Gg(M)Agg(M)a(M)gTc(F)agTaau(M)c(M)

g(M)g(M)Ta(M)c(M)c(M)c(M)

aptamer No. 27:
(SEQ ID NO: 27)
g(M)g(M)g(M)u(M)Ag(S)c(M)c(M)Gg(M)Agg(M)a(M)gTc(F)agTa(M)Au(M)c (M)g(M)g(M)Ta(M)c(M)c(M)c(M)

aptamer No. 28:
(SEQ ID NO: 28)
g(M)g(M)g(M)u(M)Agc(M)c(M)Gg(M)Agg(M)a(M)gTc(F)agTaau(M)c(M)g (M)g(M)Ta(M)c(M)c(M)c(M)

aptamer No. 29:
(SEQ ID NO: 29)
g(M)g(M)g(M)u(M)Agc(M)c(M)Gg(M)Agg(M)a(M)gTc(F)agTa(M)a(M)u(M)c -continued (M)g(M)g(M)Ta(M)c(M)c(M)

aptamer No. 30:
(SEQ ID NO: 30)
g(M)g(M)g(M)u(M)Agc(M)c(M)Gg(M)Agg(M)a(M)gTc(F)agTa(M)Au(M)c(M)

g(M)g(M)Ta(M)c(M)c(M)c(M)

aptamer No. 31:
(SEQ ID NO: 31)
g(M)g(M)g(M)u(M)Ag(S)c(M)c(M)Gg(M)Agg(M)a(M)gTc(F)agTaau(M)c(M)

g(M)g(M)TAc(M)c(M)c(M)

aptamer No. 32:
(SEQ ID NO: 32)
g(M)g(M)g(M)u(M)Agc(M)c(M)gg(M)Agg(M)a(M)gTc(F)agTa(M)a(M)u(M)c (M)g(M)g(M)TACCC aptamer No. 33:
(SEQ ID NO: 33)
g(M)g(M)g(M)u(M)Agc(M)c(M)gg(M)Agg(M)a(M)gTc(F)agTa(M)Au(M)c(M)

g(M)g(M)TACCC aptamer No. 34:
(SEQ ID NO: 34)
g(M)g(M)g(M)u(M)Agc(M)c(M)Gg(M)Agg(M)a(M)gTc(F)AgTa(M)a(M)u(M)c (M)g(M)g(M)Ta(M)c(M)c(M)c(M)

aptamer No. 35:
(SEQ ID NO: 35)
g(M)g(M)g(M)u(M)Agc(M)c(M)Gg(M)Agg(M)a(M)gTc(F)AgTa(M)Au(M)c(M)

g(M)g(M)Ta(M)c(M)c(M)c(M)

aptamer No. 36:
(SEQ ID NO: 36)
g(M)g(M)g(M)u(M)AGc(M)c(M)Gg(M)Agg(M)a(M)gTc(F)agTa(M)Au(M)c(M)

g(M)g(M)Ta(M)c(M)c(M)c(M)

aptamer No. 37:
(SEQ ID NO: 37)
g(M)g(M)g(M)u(M)Agc(M)c(M)Gg(M)Agg(M)a(M)gTc(F)agTaAu(M)c(M)g (M)g(M)Ta(M)c(M)c(M)c(M)

aptamer No. 38:
(SEQ ID NO: 38)
g(M)g(M)g(M)u(M)Agc(M)c(M)Gg(M)Agg(M)a(M)gTc(F)agTa(M)au(M)c(M)

g(M)g(M)Ta(M)c(M)c(M)c(M)

aptamer No. 39:
(SEQ ID NO: 39)
g(M)g(M)g(M)u(M)Agc(M)c(M)Gg(M)Agg(M)a(M)gTc(F)AgTaa(M)u(M)c(M)

g(M)g(M)Ta(M)c(M)c(M)c(M)

aptamer No. 40:
(SEQ ID NO: 40)
g(M)g(M)g(M)u(M)Agc(M)c(M)Gg(M)Agg(M)a(M)gTc(F)AgTa(M)au(M)c(M)

g(M)g(M)Ta(M)c(M)c(M)c(M)

aptamer No. 41:
(SEQ ID NO: 41)
g(M)g(M)g(M)u(M)Agc(M)c(M)Gg(M)agg(M)a(M)gTc(F)agTaau(M)c(M)g (M)g(M)Ta(M)c(M)c(M)c(M)

aptamer No. 42:
(SEQ ID NO: 42)
g(M)g(M)g(M)u(M)Agc(M)c(M)Gg(M)agg(M)a(M)gTc(F)agTaAu(M)c(M)g (M)g(M)Ta(M)c(M)c(M)c(M)

aptamer No. 43:

-continued aptamer No. 43:
(SEQ ID NO: 43)
g(M)g(M)g(M)u(M)Agc(M)c(M)Gg(M)agg(M)a(M)gTc(F)agTa(M)au(M)c(M)
g(M)g(M)Ta(M)c(M)c(M)c(M)

aptamer No. 44:
(SEQ ID NO: 44)
g(M)g(M)g(M)u(M)Agc(M)c(M)Gg(M)agg(M)a(M)gTc(F)AgTa(M)au(M)c(M)
g(M)g(M)Ta(M)c(M)c(M)c(M)

aptamer No. 45:
(SEQ ID NO: 45)
g(M)g(M)g(M)u(M)Ag(S)c(M)c(M)Gg(M)agg(M)a(M)gTc(F)agTaau(M)c(M)
g(M)g(M)u(F)a(M)CCC aptamer No. 46:
(SEQ ID NO: 46)
g(M)g(M)g(M)u(M)Ag(S)c(M)c(M)Gg(M)Agg(M)a(M)gTc(F)agTaau(M)c(M)
g(M)g(M)u(F)a(M)CCC aptamer No. 47:
(SEQ ID NO: 47)
g(M)g(M)g(M)u(M)Agc(M)c(M)Gg(M)a(F)gg(M)a(M)gTc(F)a(F)gTaau(M)c
(M)g(M)g(M)u(F)a(M)CCC aptamer No. 48 (Example sequence 2):
(SEQ ID NO: 48)
g(M)g(M)g(M)u(M)Agc(M)c(M)Gg(M)agg(M)a(M)gTc(F)agTaau(M)c(M)g
(M)g(M)u(F)a(M)CCC aptamer No. 49:
(SEQ ID NO: 49)
g(M)g(M)g(M)u(M)Agc(M)c(M)Gg(M)Agg(M)a(M)gTc(F)agTaau(M)c(M)g
(M)g(M)u(F)a(M)CCC aptamer No. 50:
(SEQ ID NO: 50)
g(M)g(M)g(M)u(M)Ag(S)c(M)c(M)Gg(M)a(F)gg(M)a(M)g(S)Tc(F)a(F)gTa
(M)a(M)u(M)c(M)g(M)g(M)u(F)a(M)CCC aptamer No. 51:
(SEQ ID NO: 51)
g(M)g(M)g(M)u(M)Ag(S)c(M)c(M)Gg(M)a(F)gg(M)a(M)gTc(F)a(F)g(S)Ta
(M)a(M)u(M)c(M)g(M)g(M)u(F)a(M)CCC aptamer No. 52:
(SEQ ID NO: 52)
g(M)g(M)g(M)u(M)Ag(S)c(M)c(M)Gg(M)a(F)gg(M)a(M)gUc(F)a(F)gUa(M)
a(M)u(M)c(M)g(M)g(M)u(F)a(M)CCC aptamer No. 53:
(SEQ ID NO: 53)
g(M)g(M)g(M)u(M)Ag(S)c(M)c(M)Gg(M)a(F)gg(M)a(M)gTc(F)a(F)gTgau
(M)c(M)g(M)g(M)u(F)a(M)CCC aptamer No. 54:
(SEQ ID NO: 54)
g(M)g(M)g(M)u(M)Ag(S)c(M)c(M)Gg(M)a(F)gg(M)a(M)g(S)Tc(F)a(F)g
(S)Ta(M)a(M)u(M)c(M)g(M)g(M)u(F)a(M)CCC aptamer No. 55:
(SEQ ID NO: 55)
g(M)g(M)g(M)u(M)Ag(S)c(M)c(M)Gg(M)a(F)gg(M)a(M)g(S)Tc(F)a(F)g
(M)Ta(M)a(M)u(M)c(M)g(M)g(M)u(F)a(M)CCC aptamer No. 56:
(SEQ ID NO: 56)
g(M)g(M)g(M)u(M)Ag(S)c(M)c(M)Gg(M)a(F)g(S)g(M)a(M)g(S)Tc(F)a(F)

-continued g(M)Ta(M)a(M)u(M)c(M)g(M)g(M)u(F)a(M)CCC aptamer No. 57:
(SEQ ID NO: 57)
g(M)g(M)g(M)u(M)Ag(S)c(M)c(M)Gg(M)a(F)gg(M)a(M)g(S)Tc(F)a(F)g (M)Ta(M)a(M)u(M)c(M)g(M)g(M)u(F)a(M)c(M)c(M)c(M)

aptamer No. 58:
(SEQ ID NO: 58)
g(M)g(M)g(M)u(M)a(M)g(S)c(M)c(M)Gg(M)a(F)gg(M)a(M)g(S)Tc(F)a(F)

g(M)Ta(M)a(M)u(M)c(M)g(M)g(M)u(F)a(M)c(M)c(M)c(M)

aptamer No. 59:
(SEQ ID NO: 59)
g(M)g(M)g(M)u(M)Ag(S)c(M)c(M)Gg(M)a(M)gg(M)a(M)g(S)Tc(F)a(F)g (M)Ta(M)a(M)u(M)c(M)g(M)g(M)u(F)a(M)CCC aptamer No. 60:
(SEQ ID NO: 60)
g(M)g(M)g(M)u(M)a(M)g(S)c(M)c(M)Gg(M)a(F)gg(M)a(M)gTc(F)a(F)gTa (M)a(M)u(M)c(M)g(M)g(M)u(F)a(M)c(M)c(M)c(M)

aptamer No. 61:
(SEQ ID NO: 61)
g(M)g(M)g(M)u(M)a(M)g(S)c(M)c(M)Gg(M)a(F)gg(M)a(M)g(S)Tc(F)a(F)

g(S)Ta(M)a(M)u(M)c(M)g(M)g(M)u(F)a(M)c(M)c(M)c(M)

aptamer No. 62:
(SEQ ID NO: 62)
g(M)g(M)g(M)u(M)a(M)g(S)c(M)c(M)Gg(M)a(F)gg(M)a(M)g(S)Tc(M)a(F)

g(S)Ta(M)a(M)u(M)c(M)g(M)g(M)u(F)a(M)c(M)c(M)c(M)

aptamer No. 63:
(SEQ ID NO: 63)
g(M)g(M)g(M)u(M)a(M)g(S)c(M)c(M)Gg(M)a(F)gg(M)a(M)gTc(F)a(F)gTa (M)a(M)u(M)c(M)g(M)g(M)u(M)a(M)c(M)c(M)c(M)

aptamer No. 64:
(SEQ ID NO: 64)
g(M)g(M)g(M)u(M)a(M)g(S)c(M)c(M)Gg(M)a(F)gg(M)a(M)g(S)Tc(F)a(F)

g(S)Ta(M)a(M)u(M)c(M)g(M)g(M)u(M)a(M)c(M)c(M)c(M)

aptamer No. 65:
(SEQ ID NO: 65)
g(M)g(M)g(M)u(M)a(M)g(S)c(M)c(M)Gg(M)a(F)gg(M)a(M)g(S)Tc(M)a(F)

g(S)Ta(M)a(M)u(M)c(M)g(M)g(M)u(M)a(M)c(M)c(M)c(M)

aptamer No. 66:
(SEQ ID NO: 66)
g(M)g(M)g(M)u(M)a(M)g(S)c(M)c(M)Gg(M)a(F)gg(M)a(M)g(S)u(F)c(F)a (F)g(S)u(F)a(M)a(M)u(M)c(M)g(M)g(M)u(F)Ac(M)c(M)c(M)

aptamer No. 67:
(SEQ ID NO: 67)
g(M)g(M)g(M)u(M)a(M)g(S)c(M)c(M)Gg(M)a(F)gg(M)a(M)gu(F)c(F)a(F)

gu(F)a(M)a(M)u(M)c(M)g(M)g(M)u(F)a(M)c(M)c(M)c(M)

aptamer No. 68:
(SEQ ID NO: 68)
g(M)g(M)g(M)u(M)a(M)g(S)c(M)c(M)Gg(M)a(F)gg(M)a(M)g(S)u(F)c(F)a (F)g(S)u(F)a(M)a(M)u(M)c(M)g(M)g(M)u(F)a(M)c(M)c(M)c(M)

aptamer No. 69:
(SEQ ID NO: 69)
g(M)g(M)g(M)u(M)a(M)g(S)c(M)c(M)Gg(M)a(F)gg(M)a(M)g(S)u(F)c(M)a (F)g(S)u(F)a(M)a(M)u(M)c(M)g(M)g(M)u(F)a(M)c(M)c(M)c(M)

aptamer No. 70:

-continued aptamer No. 70:
(SEQ ID NO: 70)
g(M)g(M)g(M)u(M)a(M)g(S)c(M)c(M)Gg(M)a(F)gg(M)a(M)gu(F)c(F)a(F)

gu(F)a(M)a(M)u(M)c(M)g(M)g(M)u(M)a(M)c(M)c(M)c(M)

aptamer No. 71:
(SEQ ID NO: 71)
g(M)g(M)g(M)u(M)a(M)g(S)c(M)c(M)Gg(M)a(F)gg(M)a(M)g(S)u(F)c(F)a (F)g(S)u(F)a(M)a(M)u(M)c(M)g(M)g(M)u(M)a(M)c(M)c(M)c(M)

aptamer No. 72:
(SEQ ID NO: 72)
g(M)g(M)g(M)u(M)a(M)gc(M)c(M)Gg(M)a(F)g(M)a(M)gTc(F)a(F)gTa(M)

a(M)u(M)c(M)g(M)g(M)u(F)a(M)c(M)c(M)c(M)

aptamer No. 73:
(SEQ ID NO: 73)
g(M)g(M)g(M)u(M)a(M)gc(M)c(M)gg(M)a(F)gg(M)a(M)gTc(F)a(F)gTa(M)

a(M)u(M)c(M)g(M)g(M)u(F)a(M)c(M)c(M)c(M)

aptamer No. 74:
(SEQ ID NO: 74)
g(M)g(M)g(M)u(M)a(M)gc(M)c(M)Gg(M)a(F)gg(M)a(M)gu(F)c(F)a(F)gu (F)a(M)a(M)u(M)c(M)g(M)g(M)u(F)Ac(M)c(M)c(M)

aptamer No. 75:
(SEQ ID NO: 75)
g(M)g(M)g(M)u(M)a(M)gc(M)c(M)gg(M)a(F)gg(M)a(M)gu(F)c(F)a(F)gu (F)a(M)a(M)u(M)c(M)g(M)g(M)u(F)Ac(M)c(M)c(M)

aptamer No. 76:
(SEQ ID NO: 76)
g(M)g(M)g(M)u(M)a(M)gc(M)c(M)Gg(M)a(F)gg(M)a(M)gTc(F)a(F)gTa(M)

a(M)u(M)c(M)g(M)g(M)u(M)a(M)c(M)c(M)c(M)

aptamer No. 77:
(SEQ ID NO: 77)
g(M)g(M)g(M)u(M)a(M)gc(M)c(M)gg(M)a(F)gg(M)a(M)gu(F)c(F)a(F)gu (F)a(M)a(M)u(M)c(M)g(M)g(M)u(M)a(M)c(M)c(M)c(M)

aptamer No. 78:
(SEQ ID NO: 78)
g(M)g(M)g(M)u(M)a(M)g(S)c(M)c(M)Gg(M)a(F)gg(M)a(M)gu(F)c(F)a(F)

gu(F)a(M)a(M)u(M)c(M)g(M)g(M)u(F)Ac(M)c(M)c(M)

aptamer No. 79:
(SEQ ID NO: 79)
g(M)g(M)g(M)u(M)a(M)g(S)c(M)c(M)Gg(M)a(M)gg(M)a(M)g(S)Tc(M)a(F)

g(S)Ta(M)a(M)u(M)c(M)g(M)g(M)u(M)a(M)c(M)c(M)c(M)

aptamer No. 80:
(SEQ ID NO: 80)
g(M)g(M)g(M)u(M)a(M)g(S)c(M)c(M)Gg(M)a(M)gg(M)a(M)g(S)Tc(F)a(F)

g(S)Ta(M)a(M)u(M)c(M)g(M)g(M)u(M)a(M)c(M)c(M)c(M)

aptamer No. 81:
(SEQ ID NO: 81)
g(M)g(M)g(M)u(M)a(M)g(S)c(M)c(M)Gg(M)a(M)gg(M)a(M)g(S)u(F)c(M)a (F)g(S)u(F)a(M)a(M)u(M)c(M)g(M)g(M)u(F)a(M)c(M)c(M)c(M)

aptamer No. 82:
(SEQ ID NO: 82)
g(M)g(M)g(M)u(M)a(M)g(S)c(M)c(M)Gg(M)a(M)gg(M)a(M)g(S)u(F)c(F)a (F)g(S)u(F)a(M)a(M)u(M)c(M)g(M)g(M)u(M)a(M)c(M)c(M)c(M)

aptamer No. 83:
(SEQ ID NO: 83)
g(M)g(M)g(M)u(M)a(M)g(S)c(M)c(M)Gg(M)a(M)gg(M)a(M)g(S)u(F)c(F)a -continued (F)g(S)u(F)a(M)a(M)u(M)c(M)g(M)g(M)u(F)a(M)c(M)c(M)c(M)

aptamer No. 84:
(SEQ ID NO: 84)
g(M)g(M)g(M)u(M)a(M)g(S)c(M)c(M)Gg(M)a(M)gg(M)a(M)g(S)Tc(M)a(F)

g(S)Tg(M)a(M)u(M)c(M)g(M)g(M)u(M)a(M)c(M)c(M)c(M)

aptamer No. 85:
(SEQ ID NO: 85)
g(M)g(M)g(M)u(M)a(M)g(S)c(M)c(M)Gg(M)a(M)gg(M)a(M)g(S)Tc(M)a(F)

g(S)Tga(M)u(M)c(M)g(M)g(M)u(M)a(M)c(M)c(M)c(M)

aptamer No. 86:
(SEQ ID NO: 86)
g(M)g(M)g(M)u(M)a(M)g(S)c(M)c(M)Gg(M)a(M)gg(M)a(M)g(S)u(F)c(M)a (F)g(S)u(F)ga(M)u(M)c(M)g(M)g(M)u(F)a(M)c(M)c(M)c(M)

aptamer No. 87:
(SEQ ID NO: 87)
g(M)g(M)g(M)u(M)a(M)g(S)c(M)c(M)Gg(M)a(M)gg(M)a(M)g(S)Tc(M)a(F)

g(S)Taa(M)u(M)c(M)g(M)g(M)u(M)a(M)c(M)c(M)c(M)

aptamer No. 88 (Example sequence 3):
(SEQ ID NO: 88)
g(M)g(M)g(M)u(M)a(M)g(S)c(M)c(M)Gg(M)a(M)gg(M)a(M)g(S)Tc(M)a(F)

g(S)Ta(M)au(M)c(M)g(M)g(M)u(M)a(M)c(M)c(M)c(M)

aptamer No. 89:
(SEQ ID NO: 89)
g(M)g(M)g(M)u(M)a(M)g(S)c(M)c(M)Gg(M)a(M)gg(M)a(M)g(S)Tc(M)a(F)

g(S)Taau(M)c(M)g(M)g(M)u(M)a(M)c(M)c(M)c(M)

aptamer No. 90:
(SEQ ID NO: 90)
g(M)g(M)g(M)u(M)a(M)g(S)c(M)c(M)Gg(M)a(M)gg(M)a(M)g(S)u(F)c(F)a (F)g(S)u(F)aa(M)u(M)c(M)g(M)g(M)u(F)a(M)c(M)c(M)c(M)

aptamer No. 91:
(SEQ ID NO: 91)
g(M)g(M)g(M)u(M)a(M)g(S)c(M)c(M)Gg(M)a(M)gg(M)a(M)g(S)u(F)c(F)a (F)g(S)u(F)a(M)au(M)c(M)g(M)g(M)u(M)a(M)c(M)c(M)c(M)

aptamer No. 92:
(SEQ ID NO: 92)
g(M)g(M)g(M)u(M)a(M)g(S)c(M)c(M)Gg(M)a(M)gg(M)a(M)g(S)u(F)c(F)a (F)g(S)u(F)aau(M)c(M)g(M)g(M)u(F)a(M)c(M)c(M)c(M)

aptamer No. 93:
(SEQ ID NO: 93)
g(M)g(M)g(M)u(M)Ag(S)c(M)c(M)Gg(M)a(F)gg(M)a(M)gTc(F)a(F)gTaau (M)c(M)g(M)g(M)u(F)a(M)c(M)c(M)c(M)

aptamer No. 94:
(SEQ ID NO: 94)
g(M)g(M)u(M)Ag(S)c(M)c(M)Gg(M)a(F)gg(M)a(M)gTc(F)a(F)gTaau(M)c (M)g(M)g(M)u(F)a(M)CC aptamer No. 95:
(SEQ ID NO: 95)
(g(M)u(M)Ag(S)c(M)c(M)Gg(M)a(F)gg(M)a(M)gTc(F)a(F)gTaau(M)c(M)g M)g(M)u(F)a(M)C aptamer No. 96:
(SEQ ID NO: 96)
(u(M)Ag(S)c(M)c(M)Gg(M)a(F)gg(M)a(M)gTc(F)a(F)gTaau(M)c(M)g(M)g M)u(F)a(M)

aptamer No. 97:

-continued aptamer No. 97:
(SEQ ID NO: 97)
g(M)g(M)u(M)Agc(M)c(M)Gg(M)agg(M)a(M)gTc(F)agTaau(M)c(M)g(M)g (M)u(F)a(M)CC aptamer No. 98:
(SEQ ID NO: 98)
g(M)u(M)Agc(M)c(M)Gg(M)agg(M)a(M)gTc(F)agTaau(M)c(M)g(M)g(M)u (F)a(M)C aptamer No. 99:
(SEQ ID NO: 99)
u(M)Agc(M)c(M)Gg(M)agg(M)a(M)gTc(F)agTaau(M)c(M)g(M)g(M)u(F)a(M)

aptamer No. 100:
(SEQ ID NO: 100)
g(M)g(M)u(M)a(M)g(S)c(M)c(M)Gg(M)a(M)gg(M)a(M)g(S)Tc(M)a(F)g(S)

Ta(M)au(M)c(M)g(M)g(M)u(M)a(M)c(M)c(M)

aptamer No. 101:
(SEQ ID NO: 101)
g(M)u(M)a(M)g(S)c(M)c(M)Gg(M)a(M)gg(M)a(M)g(S)Tc(M)a(F)g(S)Ta (M)au(M)c(M)g(M)g(M)u(M)a(M)c(M)

aptamer No. 102:
(SEQ ID NO: 102)
u(M)a(M)g(S)c(M)c(M)Gg(M)a(M)gg(M)a(M)g(S)Tc(M)a(F)g(S)Ta(M)au (M)c(M)g(M)g(M)u(M)a(M)

aptamer No. 103:
(SEQ ID NO: 103)
g(M)g(M)u(M)Ag(S)c(M)c(M)Gg(M)a(F)gg(M)a(M)gTc(F)a(F)gTaau(M)c (M)g(M)g(M)u(F)a(M)c(M)c(M)

aptamer No. 104:
(SEQ ID NO: 104)
g(M)u(M)Ag(S)c(M)c(M)Gg(M)a(F)gg(M)a(M)gTc(F)a(F)gTaau(M)c(M)g (M)g(M)u(F)a(M)c(M)

In the compound of the present invention, the pharmaceutically acceptable salt includes any salts and, salts with inorganic acids such as hydrochloric acid, hydrobromic acid and the like, salts with organic acids, salts with alkali metals, salts with organic bases and salts with amino acids can be mentioned.

When the compound of the present invention is provided in the form of a solvate, the solvent includes, for example, physiologically acceptable organic solvents such as ethanol, acetone, ethyl acetate and the like.

The compound of the present invention can be chemically synthesized as disclosed herein and by a method known per se in the art. Specifically, the compound of the present invention can be synthesized, for example, according to the following procedure. That is, first, an aptamer (Z) is synthesized in the direction of from the 3'-terminal to the 5'-terminal by a well-known oligonucleotide synthesis method such as phosphoramidite method (Nucleic Acids Research, 17, 7059-7071, 1989) and the like by using a commercially available oligonucleotide synthesizer (manufactured by ABI and the like). Then, using an automatic synthesizer similar to the above, a brancher is introduced into the 5'-terminal of the aptamer via a phosphodiester bond, or a brancher is introduced after addition of the aforementioned spacer (W). Phosphoramidite for synthesis to be the brancher can be synthesized by variously selecting $L_1$, $L_2$, and q in the above-mentioned formula (I) by a known method. For example, when $L_1$ and $L_2$ are 2 and q is 0, it can be synthesized according to the method described in National Publication of International Patent Application No. 2010-512421, and when $L_1$ and $L_2$ are 1 and q is 1, it can be synthesized according to the method described in National Publication of International Patent Application No. 2006-513244. Similarly, when $L_1$ and $L_2$ are 1, and q is 0, it can be synthesized according to the method described in a document (Chemistry A European Journal, 20, 12165-12171, 2014, Bioorganic and Medicinal Chemistry, 18, 8277-8282, 2010), or a commercially available product such as Symmetrical branching CED phosphoramidite (manufactured by ChemGenes) and the like can be used. The spacer (W) and the brancher are generally used in an amount of about 1-9 equivalents relative to 1 equivalent of the aptamer. Following the addition of the brancher, a spacer is added as mentioned above via a phosphodiester bond by generally using about 2-14 equivalents of spacer (Y) relative to 1 equivalent of the aptamer and similarly using an automatic synthesizer. Furthermore, a linker is added as mentioned above via a phosphodiester bond by generally using about 2-14 equivalents of linker (X) relative to 1 equivalent of the aptamer and similarly using an automatic synthesizer. After the addition up to the linker, the synthesized compound is released from the carrier by using an aqueous ammonia solution and the like, and the base part and the phosphate group part are deprotected. Then, the compound is purified by reversed-phase chromatography, ion exchange chromatography and the like to give a 5'-aminated oligonucleotide or 5'-mercapto oligonucleotide (may be a disulfide form for stabilization). Thereafter, the obtained 5'-aminated oligonucleotide or 5'-mercapto oligonucleotide (disulfide may be reduced when reacting) is reacted with the aforementioned branched PEG activated with N-hydroxysuccinimide (NHS) or branched PEG having maleimide easily reactive with a mercapto group in a suitable solution (e.g., phosphate buffer, sodium carbonate buffer, pH 6.5-9.0, 4-25° C.), for example, about 2-4 hr, whereby the branched PEG can be added to the 5'-terminal of each linker. After the reaction, purification by liquid chromatography and the like can afford the compound of the present invention.

In the compound of the present invention, the aptamer shown by Z may further contain one or more (e.g., 2 or 3) functional substances bonded thereto. The bond may be a covalent bond or noncovalent bond. The functional substance is not particularly limited, as far as it newly adds a certain function to the compound of the present invention, or is capable of changing (e.g., improving) a certain characteristic which the compound of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; those used for prolonging the half-life in blood by being bonded to a blood component such as ibuprofen and the like; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; *vinca* alkaloids such as vinblastine, vincristine or vinorelbine and analogues thereof; podophyllotoxin derivatives such as etoposide, taxanes, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, diphtheriatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction enzymes.

The compound of the present invention is superior in the blood retention property in the body of an animal as compared to conventional aptamers. Specifically, for example, the compound of the present invention can have a half-life in blood of not less than 10 hr, preferably not less than 15 hr, more preferably not less than 20 hr, in the body of the aforementioned target animals. Alternatively, the compound of the present invention can have a half-life in blood of not less than 1.2-fold, preferably not less than 1.5-fold, more preferably not less than 2-fold, in the aforementioned target animals, as compared to (i) aptamer having the same sequence, free of a brancher, and having the same branching manner of PEG and total PEG molecular weight, or (ii) aptamer having the same sequence, having a brancher and the same total PEG molecular weight, and unbranched PEG. The half-life in blood can be measured by, for example, dissolving a test substance in physiological saline (e.g., 0.2 mg/mL for mouse, 1 mg/mL for monkey), intravenously administering same to a target animal at 1 mg/kg and, after a given time, blood is collected over time. Plasma is separated, which is preserved at −70° C., and, according to the method of Judith M. Healy et al. (Pharmaceutical Research, December 2004, Volume 21, Issue 12, pp 2234-2246), the residual nucleic acid concentration of the test substance is measured by the ELOSA method (hybridization method).

The compound of the present invention can be used as, for example, a medicament, a diagnostic reagent, a test reagent or a reagent. Particularly, since the compound of the present invention has improved in vivo stability as compared to conventional aptamers, it is particularly useful as a medicament, among others, a medicament (e.g., medicament for prophylaxis or treatment) for inflammatory diseases, autoimmune diseases and the like requiring systemic administration.

Examples of the inflammatory diseases and autoimmune diseases and the like include multiple sclerosis (MS), systemic lupus erythematosus (SLE), ankylosing spondylitis (AS), Sjögren's syndrome, polymyositis (PM), dermatomyositis (DM), rheumatoid arthritis (RA), osteoarthritis (OA), inflammatory bowel disease (Crohn's disease, ulcerous *Escherichia coli* and the like), systemic sclerosis (SSc), scleroderma, periarteritis nodosa (PN), thyroid gland disease (Graves' disease, Hashimoto's thyroiditis, and the like), Guillain-Barré syndrome, primary biliary cirrhosis (PBC), idiopathic thrombocytopenic purpura, autoimmune hemolytic anemia, myasthenia gravis (MG), amyotrophic lateral sclerosis (ALS), type I diabetes mellitus, plaque psoriasis, pustular psoriasis, arthropathic psoriasis, psoriatic erythroderma, guttate psoriasis, asthma, neutrophil functional abnormalities, eosinophilic pneumonia, idiopathic pulmonary fibrosis, hypersensitive pneumonia, cancer (e.g., esophageal cancer, thyroid cancer, urinary bladder cancer, colorectal cancer, gastric cancer, pancreatic cancer, chest cancer, liver cancer, lung cancer, non-small cell lung cancer, breast cancer, neuroblastoma, glioblastoma, uterine cancer, cervical cancer, ovarian cancer, Wilms' tumor, prostate cancer, osteosarcoma), hypertrophic scar, keloid, transplantation disease (e.g., graft rejections, graft-versus-host disease), allergy (e.g., allergic rhinitis, atopic dermatitis, food hypersensitivity, urticaria, hypersensitivity pneumonitis), contact dermatitis, ANCA associated disease, Kawasaki disease, acute febrile mucocutaneous lymph node syndrome (MCLS), Duchenne muscular dystrophy, emphysema, pulmonary edema, pulmonary tuberculosis, pulmonary alveolar proteinosis, pulmonary lymphangioleiomyomatosis (LAM), pneumothorax, pleurisy, postoperative adhesion, endometriosis, adult periodontitis, bronchitis, chronic obstructive pulmonary diseases (COPD), infections, age-related macular degeneration, retinopathy, glaucoma, cataract, uveitis, Behcet's disease, hepatitis, cirrhosis, liver failure, renal infarction, nephritis, renal failure, cystitis, cerebral infarction, cerebral hemorrhage, intracranial hemorrhage, subarachnoid hemorrhage, hypertensive encephalopathy, cerebral embolism, transient cerebral ischemic attack, osteomyelitis, pyogenic arthritis, osteoporosis, hernia of intervertebral disk, gout, sweat gland abscess, palmoplantar pustulosis, circular shape alopecia, atherosclerosis, psoriasis keratoconjunctivitis (dry eye) and the like.

The compound of the present invention can also be used as a drug delivery vehicle, a probe for in vivo imaging, a probe for determination of blood concentrations of IL-17, a probe for histological staining, a probe for ELISA, and a ligand for separation and purification of IL-17.

IL-17 is known to act on various cells such as fibroblasts, endothelial cells, epithelial cells, chondrocytes, osteoblasts, dendritic cell progenitors, marrow-derived stromal cells, T cells, macrophages, and neutrophils. IL-17 induces the production and expression of various cytokines, chemokines, receptors, adhesion molecules, enzymes and the like by acting on these cells. Specifically, CXCL1 (KC or Groα), CXCL2 (MIP2 or Groβ), CXCL5 (LIX), CXCL6 (GCP-2), CXCL8 (IL-8), CXCL9 (MIG), CXCL10 (IP10), CXCL11 (I-TAC), CCL2 (MCP-1), CCL5 (RANTES), CCL7 (MCP-3), CCL11 (Eotaxin), CXCL12 (SDF-1), CCL20 (MIP3a), IL-1, IL-6, IL-19, TNF, CSF2 (GM-CSF), CSF3 (G-CSF), ICAM-1, VCAM-1, PTGS2 (COX2), NOS2 (iNOS), LCN2 (24p3), DEFB4 (BD2), S100A7 (Psoriasin), S100A8 (Calgranulin A), S100A9 (Calgranulin B), MUC5AC, MUC5B, EREG, SOCS3, TNFSF11 (RANKL), MMP1, MMP3, MMP9, MMP13, TIMP1, ADAMTS4, PGE2, SCF, CD80, CD86, MHC and the like can be mentioned. Therefore, the compound of the present invention can be used as a medicament, diagnostic drug, examination drug, or reagent for diseases associated with these cells and cytokines, chemokines and the like.

By binding to an IL-17 receptor, IL-17 activates Act1 and TRAF6, and activates the NF-κB pathway, MAP kinase pathway, C/EBP pathway and the like. Therefore, the compound of the present invention can be used as a medicament, diagnostic drug, examination drug, or reagent for diseases associated with the activation of these signal transduction pathways.

The medicament of the present invention can be one formulated with a pharmaceutically acceptable carrier. Examples of the pharmaceutically acceptable carrier include, but are not limited to, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as arginine, histidine, lysine, citric acid, sodium citrate, and acetic acid; suspension such as methylcellulose, polyvinylpyrrolidone, and aluminum stearate; dispersant such as surfactants; diluents such as water, saline, and orange juice; base waxes such as cacao butter, polyethylene glycol, and white kerosene; and the like.

Preparations suitable for oral administration are a solution prepared by dissolving an effective amount of ligand in a diluent such as water, saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be optionally coated by a method known per se for the purpose of taste masking, enteric dissolution, sustained release and the like. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., ferric oxide red, titanium dioxide and the like) and the like are used. The medicament may be any of a rapid-release preparation or sustained-release preparation. Examples of sustained-release bases include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration, transdermal administration and the like), aqueous and non-aqueous isotonic sterile injectable liquids are available, which may comprise an antioxidant, a buffer solution, a bactericidal agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, methods in which an active ingredient in a freeze-dried state is micronized and administered by inhalation using an appropriate inhalation device, or inhalation using a nebulizer or the like may be included. An inhalant can be mixed as appropriate with a conventionally used surfactant, oil, seasoning, cyclodextrin or derivative thereof and the like as required.

Here, examples of the surfactant include oleic acid, lecithin, diethylene glycol dioleate, tetrahydroflufuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monooleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, EPICLON), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like. Examples of the oil include corn oil, olive oil, cottonseed oil, sunflower oil and the like. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described compound of the present invention, blending it in an inhalation propellant and/or carrier, and filling them in an appropriate inhalation vessel. When the above-described compound of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

The dosage of the medicament of the present invention varies depending on the species and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the compound of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of allyldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying IL-17.

The compound of the present invention can be immobilized onto a solid phase carrier by a method known per se. For example, a method that introduces an affinity substance (e.g., those described above) or a predetermined functional group into the compound of the present invention, and then immobilizing the aptamer onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating IL-17. In particular, the present invention makes it possible to separate IL-17 from the proteins of other family proteins.

Therefore, in one embodiment, the present invention provides a purification method of IL-17, comprising (a) a step of contacting the compound of the present invention with a sample containing IL-17 to allow binding of IL-17 in the sample to the compound of the present invention, and (b) a step of separating IL-17 bound to the compound of the present invention from the sample.

The method of purification and concentration of the present invention can comprise adsorbing IL-17 to the solid phase carrier of the present invention, and eluting the adsorbed IL-17 with an eluent. Adsorption of IL-17 to the solid phase carrier of the present invention can be achieved by a method known per se. For example, an IL-17-containing sample (e.g., bacterial or cell culture, culture supernatant, or blood) is introduced into the solid phase carrier of the present invention or a composition containing the same. IL-17 can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, a potassium salt (e.g., KCl), a sodium salt (e.g., NaCl), a magnesium salt (e.g., $MgCl_2$), a surfactant (e.g., Tween 20, Triton, NP40), and glycerin. The method of purification and concentration of the present invention can further comprise washing the solid phase carrier using a washing solution after IL-17 adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The compound of the present invention can be utilized as a detection probe, particularly as a probe for detection of IL-17. The method of labeling the aptamer is not particularly limited; methods known per se can be applied. Such methods include, for example, labeling with a radioisotope, labeling with a fluorescent dye or fluorescent protein, and the like.

The present invention also provides a method of detecting and quantifying IL-17. In particular, the present invention makes it possible to detect and quantify IL-17 separately from the proteins of other family proteins. The method of detection and quantitation of the present invention can comprise measuring IL-17 by utilizing the compound of the present invention (e.g., by the use of the solid phase carrier of the present invention).

Therefore, in one embodiment, the present invention provides a detection method of IL-17, comprising (a) a step of contacting the compound of the present invention with a test sample to allow binding of IL-17 in the sample to the compound of the present invention, and (b) a step of detecting IL-17 bound to the compound of the present invention.

The method of detecting and quantifying IL-17 can be performed in the same manner as an immunological method, except that the compound of the present invention is used in place of an antibody. Therefore, by using the compound of the present invention in place of an antibody, in the same manner as such methods as enzyme immunoassay (EIA) (e.g., direct competitive ELISA, indirect competitive ELISA, sandwich ELISA), radioimmunoassay (RIA), fluorescence immunoassay (FIA), Western blotting (e.g., use in place of a secondary antibody in Western blotting), immunohistochemical staining method, and cell sorting method, detection and quantitation can be performed. These methods can be useful not only in, for example, measuring IL-17 contents in living organisms or biological samples, and in diagnosing a disease associated with IL-17, but also for objects other than disease diagnosis such as scientific object, experiment and study object, and the like, including detection or quantification of IL-17 by using the compound of the present invention instead of an antibody, and a biological sample derived from human or animal other than human, or a sample other than biological samples.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

Example 1: Synthesis (or Preparation) of Aptamer Conjugated with PEG-Linker-Spacer-Brancher The nucleic acid sequences used for the aptamers in the Examples are shown below. Example sequences 1-4 are sequences encompassed in the Claims of an earlier application, PCT/JP2014/057919 (WO 2014/148638).

```
Example sequence 1 (aptamer No. 8)
                                        (SEQ ID NO: 8)
g(M)g(M)g(M)u(M)Ag(S)c(M)c(M)Gg(M)a(F)gg(M)a(M)

gTc(F)a(F)gTaau(M)c(M)g(M)g(M)u(F)a(M)CCC_(t)

Example sequence 2 (aptamer No. 48)
                                        (SEQ ID NO: 48)
g(M)g(M)g(M)u(M)Agc(M)c(M)Gg(M)agg(M)a(M)gTc(F)ag Taau(M)c(M)g(M)g(M)u(F)a(M)CCC_(t)

Example sequence 3 (aptamer No. 88)
                                        (SEQ ID NO: 88)
g(M)g(M)g(M)u(M)a(M)g(S)c(M)c(M)Gg(M)a(M)gg(M)a(M)

g(S)Tc(M)a(F)g(S)Ta(M)au(M)c(M)g(M)u(M)a(M)c (M)c(M)c(M)_(t)

Example sequence 4 (aptamer No. 93)
                                        (SEQ ID NO: 93)
g(M)g(M)g(M)u(M)Ag(S)c(M)c(M)Gg(M)a(F)gg(M)a(M)

gTc(F)a(F)gTaau(M)c(M)g(M)g(M)u(F)a(M)c(M)c(M)c (M)_(t)
```

Note that a, g, c, u are each a ribonucleotide wherein the base is adenine, guanine, cytosine and uracil, respectively, A, G, C, T are each a deoxyribonucleotide wherein the base is adenine, guanine, cytosine and thymine, respectively. Parentheses in nucleotide indicate modification of the nucleotide, (M) indicates that, when the nucleotide is a ribonucleotide, a hydroxyl group at the 2'-position of ribose therein is substituted by an O-methyl group, and (F) indicates that, when the nucleotide is a ribonucleotide, a hydroxyl group at the 2'-position of ribose therein is substituted by a fluorine atom, and (S) indicates that nucleotide is phosphorothioated. (t) indicates idT (inverted deoxy thymidine) added to the 3'-terminal or 5-'terminal in the in vivo tests. When idT is added to the 3'-terminal, the head of the sequence is the 5'-terminal and the end is the 3'-terminal.

Each aptamer was synthesized using an oligonucleotide automatic synthesizer and according to a solid phase method using a phosphoramidite method.

Using the nucleotide at the 3'-terminal side of each nucleic acid sequence as a starting material, the nucleotide was supported on a synthesis carrier such that the amount at the time of start of the synthesis was 150 μmol as the initial charged amount, filled in a synthesis column, and set on an automatic synthesizer. According to the general automatic synthesis program, the nucleic acid sequence was elongated by one base in the 3'→5' direction and the sequence was synthesized up to 5'-OH as the terminal of the sequence.

The brancher, spacer and linker were also introduced into the aptamer in the same manner as above by a synthesis reaction using an automatic synthesizer. As the brancher, 6 equivalents, namely, 900 μmol, of Symmetrical branching CED phosphoramidite (manufactured by ChemGenes) was used to perform an addition reaction on the 5'-terminal side of the nucleic acid sequence via a phosphodiester bond. Subsequent to the addition of the brancher, a spacer (DMT-triethyloxy-Glycol phosphoramidite manufactured by ChemGenes) was added via a phosphodiester bond in the same manner by a synthesis reaction using an automatic synthesizer. Furthermore, to add an amino group to the 5'-terminal side, an ssH amino linker (ssH-Linker phosphoramidite manufactured by Sigma-Aldrich) was added via a phosphodiester bond. 9 equivalents (1350 mol) of these were used.

After the addition up to the ssH amino linker, the base part and the phosphate group part were deprotected by releasing from the synthesis carrier with an aqueous ammonia solution. Purification was performed by reversed-phase chromatography, ion exchange chromatography or the like to give the object 5'-aminated oligonucleotide.

An aqueous solution of the obtained 5'-aminated oligonucleotide (3 mmol/L) 4560 μL (13.68 μmol, 27.36 μmol of amino group) and PEG manufactured by Jemkem (Y-NHS-40K Y-shape PEG NHS Ester, MW40000, 5 mmol/L) 24624 μL (123.12 μmol) dissolved in DMSO:ACN=4:1 were reacted in 0.1 M sodium carbonate buffer (pH 9.0) at 25° C. for 2 hr. The final concentration of oligonucleotide at this time was 0.42 mmol/L, and the final concentration of PEG was 3.79 mmol/L. After the reaction, purification by liquid chromatography gave the object PEGylated oligonucleotide (see FIGS. 1, 2).

Experimental Example 1: Blood Pharmacokinetics of Aptamer Conjugated with PEG-Linker-Spacer-Brancher in Mice To examine the effect of the introduction of PEG-linker-spacer-brancher into an aptamer, an aptamer added with 2 branched PEG via a brancher (Example sequences 1, 2, 4, FIG. 1 structure 1), and an aptamer in which branched PEG was added to a conventionally-known structure without a brancher (the same, FIG. 1 structure 4) were synthesized, and blood pharmacokinetics were examined in mice. Each aptamer was dissolved at 0.2 mg/mL in saline, and intravenously administered to a male C57BL/6 mouse (Charles River Company) at 1 mg/kg. The blood was collected over time from 5 min to 72 hr later. The plasma was separated and preserved at −70° C., and the concentration of aptamer in plasma was measured according to the method reported by Judith M. Healy et al., (Pharmaceutical Research, December 2004, Volume 21, Issue 12, pp 2234-2246) and using the ELOSA method (hybridization method) The results are shown in the following Table 1.

TABLE 1

Blood pharmacokinetics of aptamer conjugated with PEG-
linker-spacer-brancher in mice (intravenous administration)

| aptamer*) | brancher | number of PEG per aptamer | molecular weight per one PEG | half-life in blood (hr) |
|---|---|---|---|---|
| Example sequence 1 | present | 2 | 40 kDa | 25.7 |
| | absent | 1 | 80 kDa | 17.1 |
| Example sequence 2 | present | 2 | 40 kDa | 22.5 |
| | absent | 1 | 80 kDa | 10.5 |
| Example sequence 4 | present | 2 | 40 kDa | 28.7 |
| | absent | 1 | 80 kDa | 17.5 |

*)total molecular weight of branched PEG added to one aptamer is 80 kDa

As a result of the measurement, in the aptamers newly introduced with a brancher (Example sequence 1, 2, 4, FIG. 1 structure 1), the half-life in blood was extended 2-fold or more at the maximum as compared to the conventionally-known aptamer (the same, FIG. 1 structure 4). Therefore, it was confirmed that connecting nucleic acid sequence and PEG by using a linker-spacer-brancher is highly useful for the maintenance of the blood concentration of aptamer.

Experimental Example 2: Comparison of Blood Pharmacokinetics Due to Difference in Spacer.Linker Connecting PEG and Brancher in Mice The presence or absence and the species of spacer.linker connecting brancher and PEG were studied. An aptamer in which a brancher was added to the nucleic acid sequence of Example sequence 2, and a spacer and an ssH amino linker were used to connect 40 kDa 2 branched PEG (total PEG molecular weight: 80 kDa, FIG. 1 structure 1), an aptamer in which only an ssH amino linker were used without an intervening spacer (total PEG molecular weight: 80 kDa, FIG. 1 structure 2), and an aptamer in which "5'-MMT-Amino-Modifier-11-CE linker" as a linker (total PEG molecular weight: 80 kDa, FIG. 1 structure 3) were used were synthesized. Each aptamer was dissolved at 0.2 mg/mL in saline, and intravenously administered to a male C57BL/6 mouse (Charles River Company) at 1 mg/kg. The blood was collected over time from 5 min to 72 hr later. The plasma was separated and preserved at −70° C., and the concentration of aptamer of the present invention in plasma was measured according to the method reported by Judith M. Healy et al., (Pharmaceutical Research, December 2004, Volume 21, Issue 12, pp 2234-2246) and using the ELOSA method (hybridization method) The results are shown in the following Table 2.

TABLE 2

Evaluation of spacer · linker connecting brancher and
40 kDa 2 branched PEG (total PEG molecular weight: 80 kDa)

| aptamer | spacer | linker | half-life in blood (hr) |
|---|---|---|---|
| Example sequence 2 | present | ssH amino linker | 22.5 |
| | absent | ssH amino linker | 27.0 |
| | absent | 5'-MMT-Amino-Modifier-11-CE-linker | 21.8 |

As a result of the measurement, the half-life in blood of the aptamer in which ssH amino linker alone connected PEG and brancher (FIG. 1 structure 2) was extended most and was 27 hr. However, the half-life in blood of the aptamer in which spacer and ssH amino linker connected PEG and brancher (FIG. 1 structure 1) and the half-life in blood of the aptamer in which "5'-MMT-Amino-Modifier-11-CE linker" connected PEG and brancher (FIG. 1 structure 3) were 22.5 hr and 21.8 hr, and the three aptamers did not show a large difference in the half-life in blood.

From the above, it was confirmed that, in the structure of the PEG-linker-spacer-brancher clarified to maintain the blood concentration of aptamer for a markedly long term, a spacer is not necessarily required and the species of the linker does not need to be limited.

Experimental Example 3: Comparison of Blood Pharmacokinetics Due to Difference in the Species of PEG Added to Nucleic Acid Via Brancher-Spacer-Linker in Mice According to Experimental Example 1, aptamers in which a brancher, a spacer, an ssH amino linker were added to the nucleic acid sequence of Example sequence 3, and 40 kDa 2 branched PEG or 40 kDa unbranched PEG was added (both total PEG molecular weight: 80 kDa in total) were synthesized (FIG. 1 structure 1). Each aptamer was dissolved at 0.2 mg/mL in saline, and intravenously administered to a male C57BL/6 mouse (Charles River Company) at 1 mg/kg. The blood was collected over time from 5 min to 72 hr later. The plasma was separated and preserved at −70° C., and the concentration of aptamer of the present invention in plasma was measured according to the method reported by Judith M. Healy et al., (Pharmaceutical Research, December 2004, Volume 21, Issue 12, pp 2234-2246) and using the ELOSA method (hybridization method). The results are shown in the following Table 3.

TABLE 3

Evaluation of the species of PEG added to nucleic acid
via brancher-spacer-linker

| aptamer | number of branch in PEG | molecular weight | total PEG molecular weight | half-life in blood (hr) |
|---|---|---|---|---|
| Example sequence 3 | 2 | 40 kDa | 80 kDa | 22.8 |
| | not branched | 40 kDa | 80 kDa | 4.9 |

When PEG without branch was used, the half-life in blood of the aptamer was markedly short and was 4.9 hr as compared to use of 2 branched PEG (22.8 hr).

From the above, it could be confirmed that, in the structure of the PEG-linker-spacer-brancher clarified to maintain the blood concentration of aptamer for a markedly long term, PEG to be added was confirmed to preferably has at least two branched chains.

Experimental Example 4: Blood Pharmacokinetics of Aptamer Conjugated with PEG-Linker-Spacer-Brancher by Subcutaneous Administration to Mice According to Experimental Example 1, aptamers in which a brancher, a spacer, an ssH amino linker were added to the nucleic acid sequences of Example sequences 1, 2, 3 and 4, and 40 kDa 2 branched PEG was added (both total PEG molecular weight: 80 kDa) were synthesized (FIG. 1 structure 1). Each aptamer was dissolved at 0.1 mg/mL in saline, and subcutaneously administered to a male C57BL/6 mouse (Charles River Company) at 1 mg/kg. The blood was collected over time from 30 min to 72 hr later. The plasma was separated and preserved at −70° C., and the concentration of aptamer of the present invention in plasma was measured according to the method reported by Judith M. Healy et al., (Pharmaceutical Research, December 2004, Volume 21, Issue 12, pp 2234-2246) and using the ELOSA method (hybridization method). The results are shown in the following Table 4.

TABLE 4

Blood pharmacokinetics of aptamer conjugated with PEG-linker-spacer-brancher (subcutaneous administration) in mice

| aptamer | AUCinf (hr · ng/mL) | $t_{1/2}$ (hr) | Cmax (ng/mL) | Tmax (hr) |
|---|---|---|---|---|
| Example sequence 1 | 554000 | 30.1 | 9220 | 14 |
| Example sequence 2 | 301000 | 25.3 | 6450 | 12 |
| Example sequence 3 | 572000 | 29.8 | 9430 | 24 |
| Example sequence 4 | 626000 | 32.7 | 9520 | 16 |

It could be confirmed that an aptamer conjugated with PEG-linker-spacer-brancher transfers into blood even by subcutaneous administration, and can maintain a high blood concentration for a long time.

Experimental Example 5: Blood Pharmacokinetics of Aptamer Conjugated with PEG-Linker-Spacer-Brancher in Monkey To examine blood pharmacokinetics in monkey, in the same manner as in Experimental Example 4, aptamers in which a brancher, a spacer, an ssH amino linker were added to the nucleic acid sequences of Example sequences 1, 3 and 4, and 40 kDa 2 branched PEG was added (total PEG molecular weight: 80 kDa) were synthesized (FIG. 1 structure 1). These aptamers were intravenously or subcutaneously administered to Cynomolgus monkeys and blood pharmacokinetics was examined. The aptamer was dissolved at 1 mg/mL in saline, and intravenously administered to Cynomolgus monkeys at 1 mg/kg. The blood was collected from 5 min to 96 hr. The plasma was separated and preserved at −70° C., and the residual nucleic acid concentration in plasma was measured for the aptamer of the present invention according to the method reported by Judith M. Healy et al., (Pharmaceutical Research, December 2004, Volume 21, Issue 12, pp 2234-2246) and using the ELOSA method (hybridization method). Similarly, the aptamer was subcutaneously administered at 1 mg/kg/mL, and the blood was collected from 15 min to 120 hr. By a similar method, the plasma was separated and preserved at −70° C., and the aptamer concentration in plasma was measured by the ELOSA method.

Figure 3:
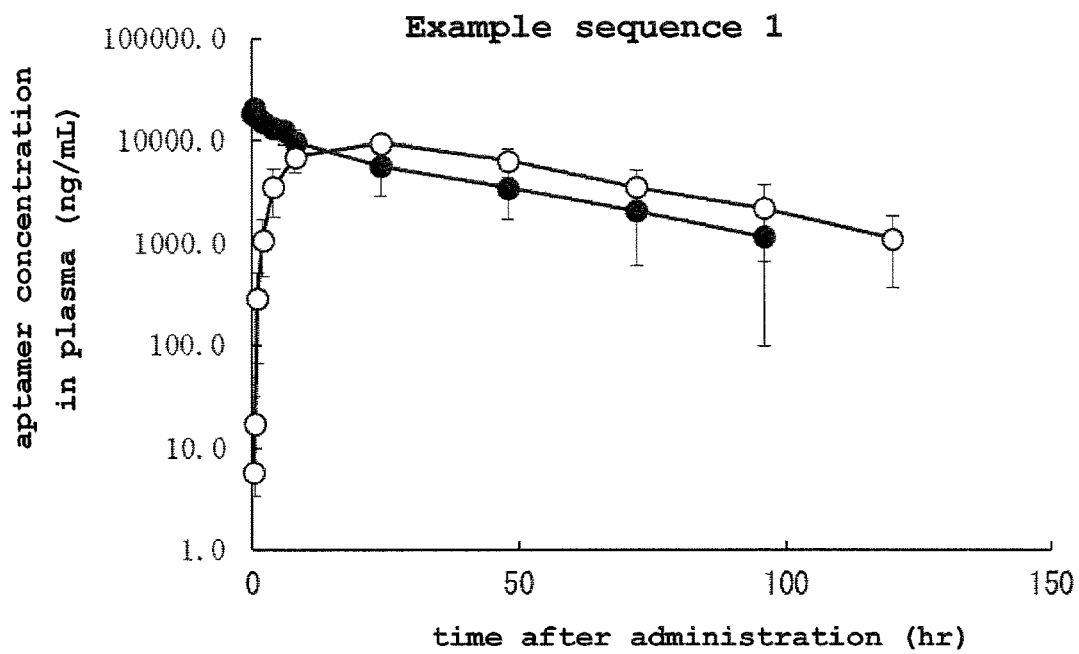
FIG. 3 shows a blood concentration profile of the aptamer (Example sequence 1) when it was intravenously administered (closed circle) or subcutaneously administered (open circle) to a monkey. Each value shows mean±standard deviation (n=3).
Figure 4:
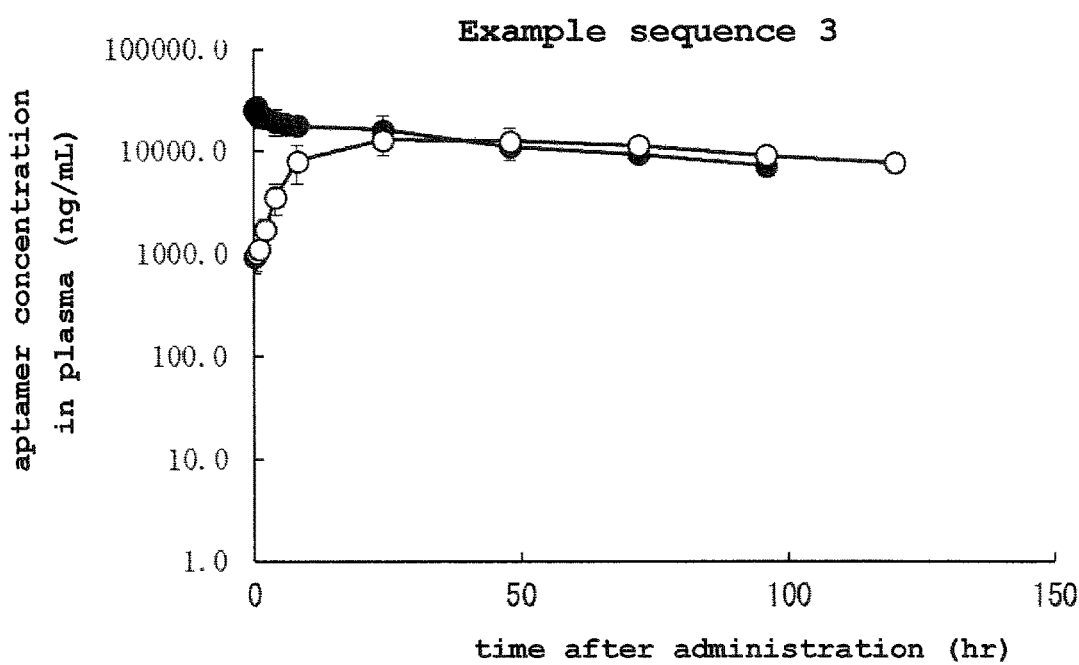
FIG. 4 shows a blood concentration profile of the aptamer (Example sequence 3) when it was intravenously administered (closed circle) or subcutaneously administered (open circle) to a monkey. Each value shows mean±standard deviation (n=3).
Figure 5:
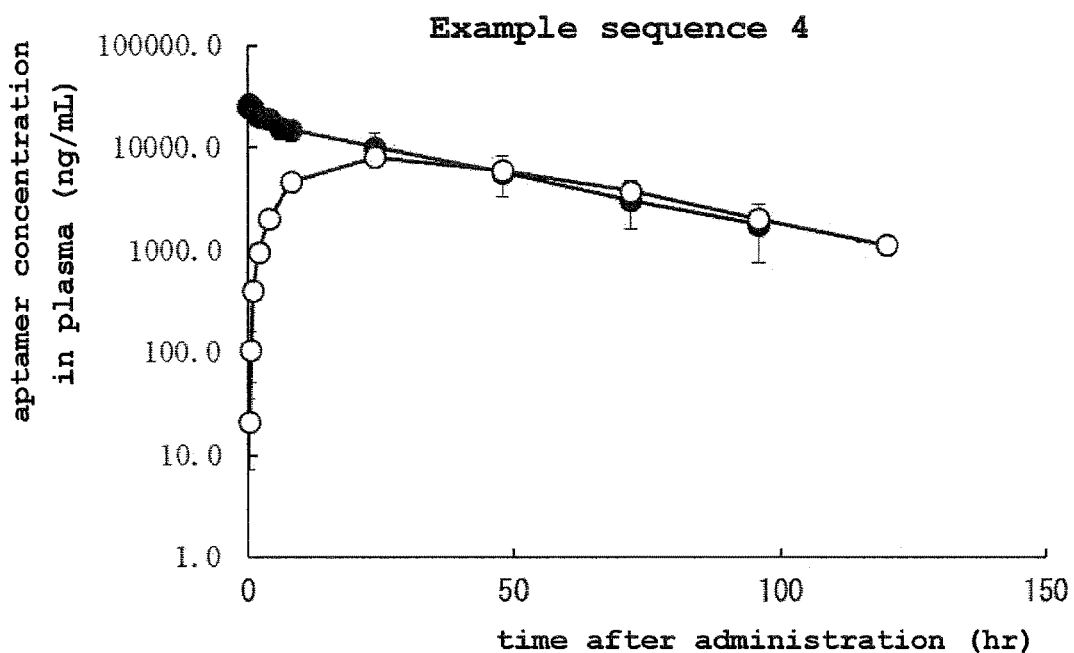
FIG. 5 shows a blood concentration profile of the aptamer (Example sequence 4) when it was intravenously administered (closed circle) or subcutaneously administered (open circle) to a monkey. Each value shows mean±standard deviation (n=3).

As a result of the measurement, as shown in FIG. 3, FIG. 4 and FIG. 5, it was found that the aptamer conjugated with PEG-linker-spacer-brancher can maintain a high blood concentration also in monkey for a very long term corresponding to day 1 to day 5 after administration. Particularly, in the aptamer of Example sequence 3, the half-life was drastically extended to 72.0 hr (intravenous administration) and 107.0 hr (subcutaneous administration) (FIG. 4).

Experimental Example 6: IL-17 Neutralization Activity (In Vitro) of Aptamer Conjugated with PEG-Linker-Spacer-Brancher Aptamers in which a brancher, a spacer, an ssH amino linker were added to the nucleic acid sequences of Example sequences 1, 2, 3 and 4, and 40 kDa 2 branched PEG was added (total PEG molecular weight: 80 kDa each) were synthesized (FIG. 1 structure 1). The IL-17 neutralization activity of each aptamer was measured along with the aptamer having the original nucleic acid sequence alone. The evaluation was based on the measurement of the amount of IL-6 released in the cultured cells by the stimulation of IL-17 and TNFα to the cells.

Human IL-17 (10 ng/mL) and aptamers diluted to various concentrations were pre-incubated at 37° C. for 30 min, and added to NIH3T3 cells (ATCC, CRL1658, $1.25\times10^5$ cell/mL) together with mouse TNF (2 ng/mL). Then, after incubation for 24 hr, the culture supernatant was collected. After preservation at −70° C., the amount of produced IL-6 was measured by the ELISA method. The IL-17 inhibitory action of each aptamer was evaluated from the amount of produced IL-6. The 50% inhibitory concentration ($IC_{50}$ value) is shown in the following Table 5.

An ELISA method for verifying IL-17 inhibitory action of aptamer was performed as follows.

A microtiter plate for ELISA was coated with rat anti-mouse IL-6 antibody (BD Biosciences, 2 μg/mL; 100 μL/well) diluted with PBS, and incubated at 4° C. overnight. The next day, the microtiter plate was washed 3 times with PBS/0.05% Tween 20, and blocked with PBS/1% BSA (200 μL/well) at room temperature for 2 hr. Then, the plate was washed 3 times with PBS/0.05% Tween 20. Recombinant mouse IL-6 (BD Biosciences; 100 μL/well) serially diluted with PBS/1% BSA/0.05% Tween 20 or culture supernatants (100 μL/well) were added to the plate. After incubation at room temperature for 2 hr, the plate was washed 3 times with PBS/0.05% Tween 20. Then, 100 μL/well of biotin conjugated rat anti-mouse IL-6 antibody (BD Biosciences) was added at final dilution of 1/500, and the mixture was reacted at room temperature for 1 hr. After washing 3 times with PBS/0.05% Tween 20, 100 μL/well of alkaline phosphatase conjugated streptavidin was added at final dilution of 1/1000. After 30 min at room temperature, the plate was again washed 4 times with PBS/0.05% Tween 20, and a substrate (1-Step PNPP; Thermo Fisher Scientific Inc; 100 μL/well) was added. After 15 min, aqueous sodium hydroxide solution (2N: 50 μL/well) was added to stop the reaction, and the plate was read on a microtiter reader (Bio-Rad) by using a 405 nm filter.

TABLE 5

IL-17 neutralization activity of aptamer conjugated with PEG-linker-spacer-brancher

| aptamer | $IC_{50}$ (nM) |
|---|---|
| Example sequence 1 | 0.041 |
| Example sequence 1*⁾ | 0.223 |
| Example sequence 2 | 0.18 |
| Example sequence 2*⁾ | 0.30 |
| Example sequence 4 | 0.060 |
| Example sequence 4*⁾ | 0.123 |

*⁾nucleic acid sequence alone

As a result of the measurement, the aptamer conjugated with PEG-linker-spacer-brancher inhibited IL-6 production induced by IL-17. Therefore, it was confirmed that the aptamer conjugated with PEG-linker-spacer-brancher of the present invention retains IL-17 neutralization activity.

Experimental Example 7-1: IL-17 Neutralization Activity Test (In Vivo) of Aptamer Conjugated with PEG-Linker-Spacer-Brancher Whether an aptamer conjugated with PEG-linker-spacer-brancher can inhibit the action of IL-17 in vivo was confirmed with murine air pouch inflammation model by reference to Biochemical Pharmacology 77, 878-887 (2009).

In the same manner as in Experimental Example 6, aptamers in which a brancher, a spacer, an ssH amino linker were added to the nucleic acid sequences of Example sequences 1, 3 and 4, and 40 kDa 2 branched PEG was added (total PEG molecular weight: 80 kDa) were synthesized (FIG. 1 structure 1). The back of a male C57BL/6J (7-week-old, Charles River Company) mouse was shaved and, the next day and 4 days later, air (2.5 mL) was subcutaneously injected into the back. At 3 days after the second air injection, the aptamer conjugated with PEG-linker-spacer-brancher of the present invention (0.3, 1, 3 mg/kg) or saline was intraperitoneally administered and, 1 hr later, 2% aqueous carbomethylcellulose solution containing IL-17 (0.5 μg) was administered into air pouch. The exudate in the air pouch was collected 24 hr after IL-17 injection. After preservation at −70° C., the amount of IL-6 in the exudate was measured by ELISA described in Experimental Example 6.

Figure 6:
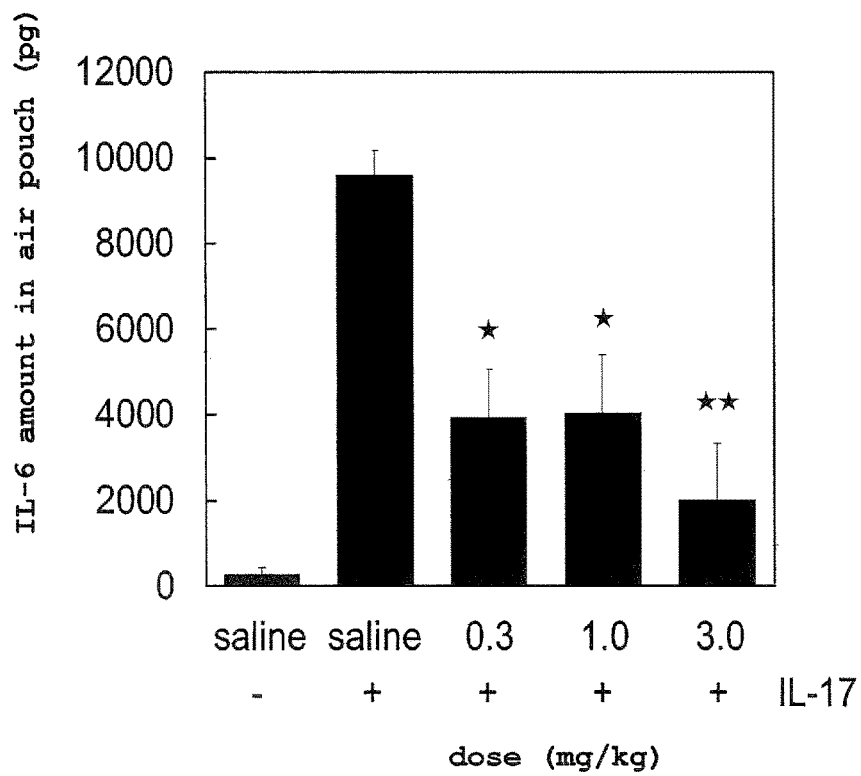
FIG. 6 shows in vivo IL-17 neutralization activity (air pouch inflammation model) of aptamer (Example sequence 1). Each value shows mean+standard error (n=7, 8). ★$p<0.01$, ★★$p<0.001$ (comparison with IL-17+, saline administration group, Dunnett's test). −: administration of 2% aqueous carboxymethylcellulose solution free of human IL-17. +: administration of 2% aqueous carboxymethylcellulose solution containing human IL-17 (0.5 μg).
Figure 7:
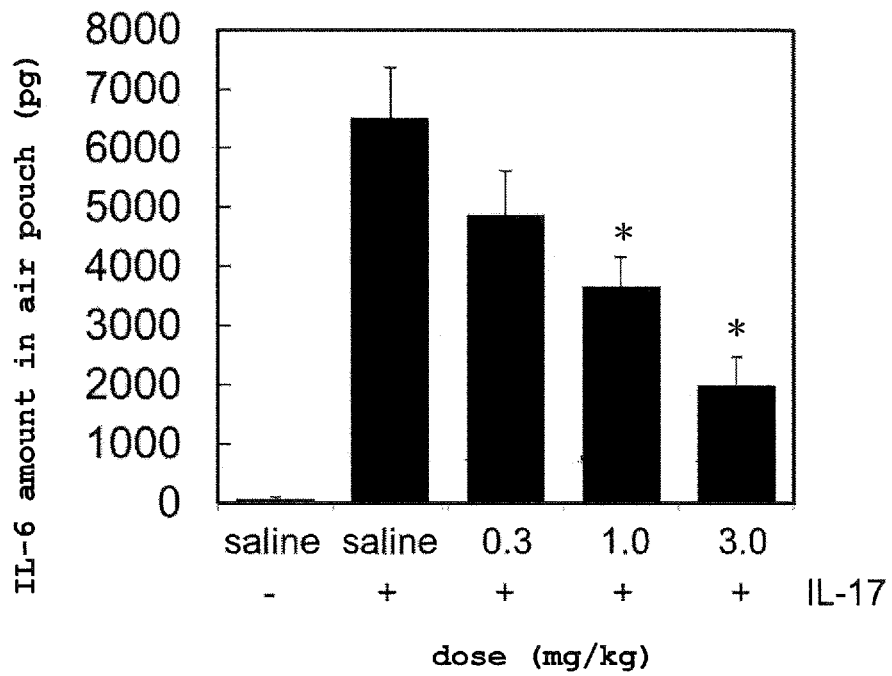
FIG. 7 shows in vivo IL-17 neutralization activity (air pouch inflammation model) of aptamer (Example sequence 3). Each value shows mean+standard error (n=7, 8). *p<0.001 (comparison with IL-17+, saline administration group, Dunnett's test). −: administration of 2% aqueous carboxymethylcellulose solution free of human IL-17. +: administration of 2% aqueous carboxymethylcellulose solution containing human IL-17 (0.5 μg).
Figure 8:
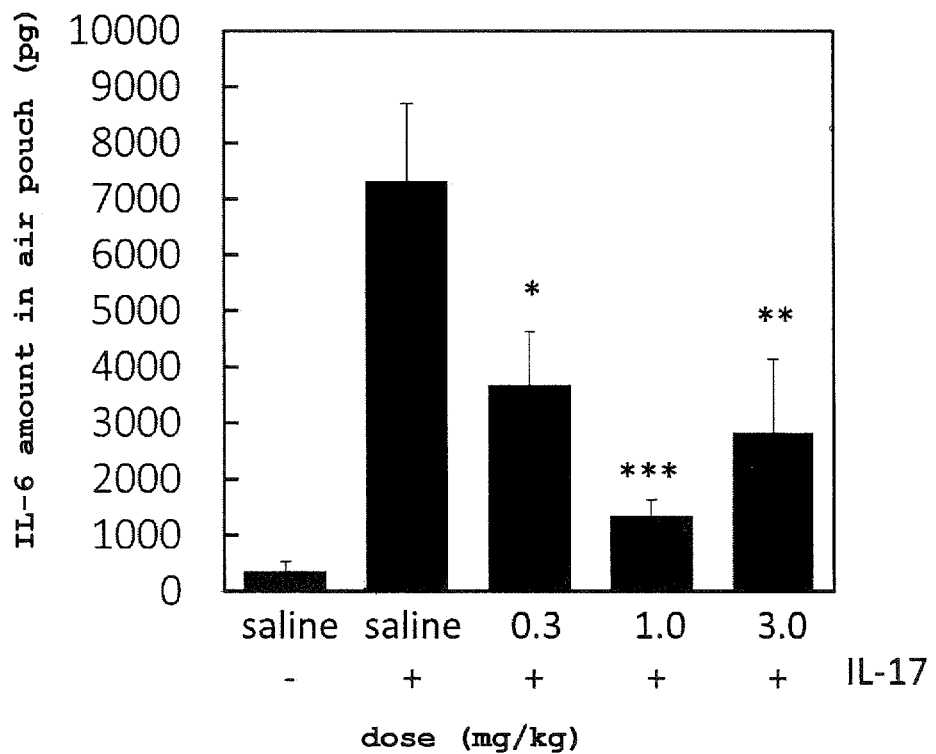
FIG. 8 shows in vivo IL-17 neutralization activity (air pouch inflammation model) of aptamer (Example sequence 4). Each value shows mean+standard error (n=8). *p<0.05, p<0.01, *p<0.001 (comparison with IL-17+, saline administration group, Dunnett's test). −: administration of 2% aqueous carboxymethylcellulose solution free of human IL-17. +: administration of 2% aqueous carboxymethylcellulose solution containing human IL-17 (0.5 μg).

As shown in FIGS. 6, 7, 8, the amount of IL-6 in air pouch was significantly low in the group administered with the aptamer of the present invention. Therefore, it was confirmed that the aptamer conjugated with PEG-linker-spacer-brancher of the present invention retains IL-17 neutralization activity also in vivo.

Experimental Examples 7-2: IL-17 Neutralization Activity Test (In Vivo) of Aptamer Conjugated with PEG-Linker-Spacer-Brancher The sustainability of the in vivo IL-17 neutralization activity of an aptamer conjugated with PEG-linker-spacer-brancher and an aptamer conjugated with a conventionally-used PEG-linker alone was compared in collagen-induced arthritis model mouse. In the same manner as in Experimental Example 6, aptamers in which a brancher, a spacer, an ssH amino linker were added to the nucleic acid sequence of Example sequence 1, and 40 kDa 2-branched PEG was added (total PEG molecular weight: 80 kDa) were synthesized (FIG. 1 structure 1). According to the method reported by S Toyama et al., (Arthritis Res Ther 12, R92 (2010)), the suppressive effect of the aptamer of the present invention on collagen-induced arthritis model was examined.

That is, a male DBA/1 mouse (8-week-old, Charles River Company) was intradermally administered at the base of tail with bovine Type II collagen (200 μg/head, Collagen Research Center) emulsified with complete adjuvant (Chondrex) (day 1 of experiment). On day 22 of the experiment, the mouse was boosted with bovine Type II collagen emulsified with incomplete adjuvant, and synthesized aptamer (3 mg/kg) was intraperitoneally administered once per two days. As a control, saline was intraperitoneally administered once per two days at the dose of 10 mL/kg. The animal was observed every day, the degree of inflammation of each limb was scored (maximum 16 per mouse) in 5 levels from 0 (no symptom) to 4 (redness of whole limb and maximum swelling), and the efficacy of the aptamer of the present invention on arthritis was evaluated.

Figure 9:
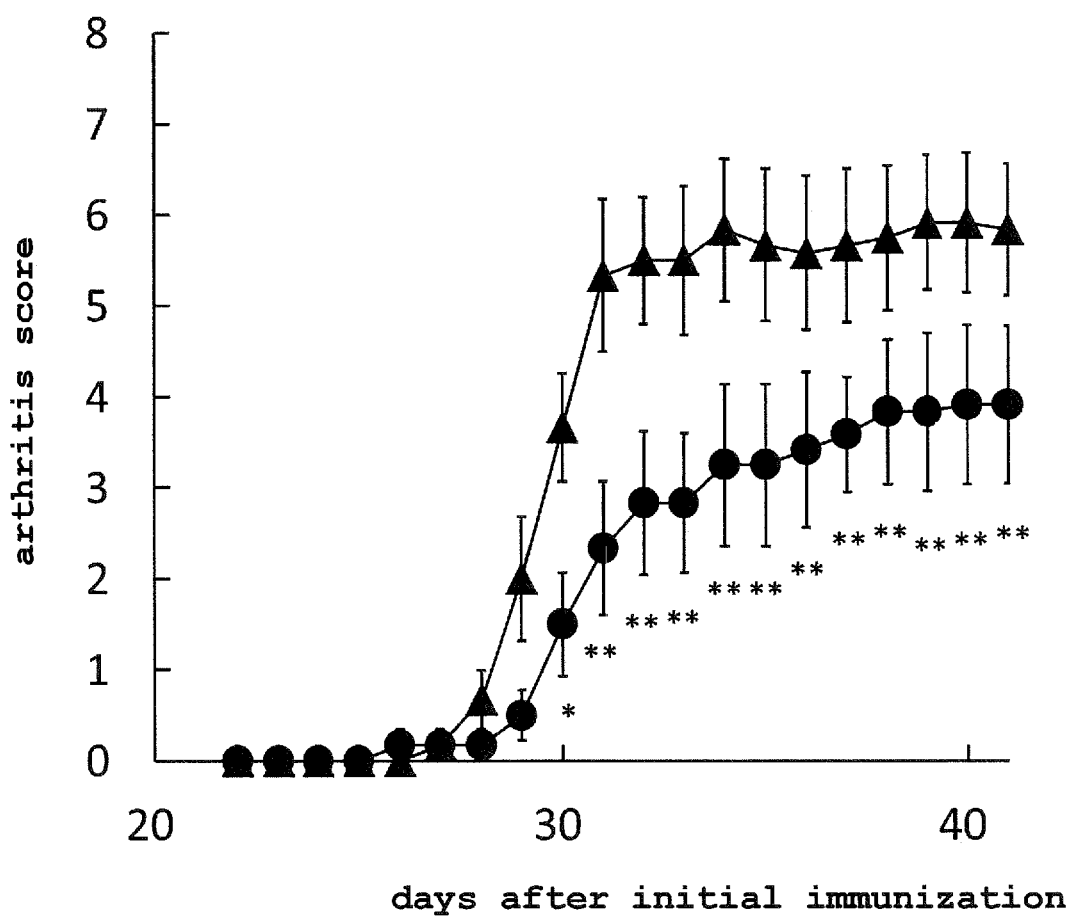
FIG. 9 shows in vivo IL-17 neutralization activity (collagen-induced arthritis model) of aptamer (Example sequence 1). Arthritis score (per one limb) 0: no symptom, 1: redness or swelling in only one joint, 2: redness or swelling in two or more joints, 3: swelling of entire limb, 4: maximum swelling of entire limb. Closed circle: with PEG-linker-spacer-brancher (total PEG molecular weight: 80 kDa), closed triangle: saline. Each value shows mean±standard error of arthritis score of four limbs (n=12). *p<0.01, **p<0.001 (comparison with saline administration group, Dunnett's test).

As shown in FIG. 9, in the group administered with the aptamer added with PEG via a brancher (the same, FIG. 1 structure 1), the arthritis score significantly decreased from day 30 after initial immunization as compared to the control group administered with saline. Therefore, it was confirmed that the aptamer conjugated with PEG-linker-spacer-brancher of the present invention retains IL-17 neutralization activity longer in vivo.

In the same test, the blood was collected 48 hr after the final administration. The plasma was separated and preserved at −70° C., and the residual nucleic acid concentration in the plasma was measured for the aptamer of the present invention according to the method reported by Judith M. Healy et al., (Pharmaceutical Research, December 2004, Volume 21, Issue 12, pp 2234-2246) and using the ELOSA method (hybridization method). The results of the aptamer concentration measurement are shown in the following Table 6.

TABLE 6

Comparison of concentration of aptamer in plasma

| aptamer | brancher | PEG number per one aptamer | molecular weight per one PEG | total PEG molecular weight | concentration in plasma (ng/mL) |
| --- | --- | --- | --- | --- | --- |
| Example sequence 1 | present | 2 | 40 kDa | 80 kDa | 20600 |
| | absent | 1 | 40 kDa | 40 kDa | 191 |

As a result of the measurement, the aptamer newly introduced with a brancher (Example sequence 1, FIG. 1 structure 1) shows a 100-fold or more higher concentration in plasma as compared to an aptamer free of brancher introduction. Therefore, it was confirmed that connecting a nucleic acid sequence and PEG via a linker-spacer-blancher is very useful for an aptamer to maintain blood concentration for a long term and exhibit efficacy.

This application is based on a patent application No. 2015-237491 filed in Japan (filing date: Dec. 4, 2015), the contents of which are incorporated in full herein.

The invention claimed is:

1. A compound represented by the following formula (I):

(I)

[Chemical structure showing: bPEG₁-T₁-X₁-(Y₁)n₁-O-P(=O)(O⁻)-O-(CH₂)L₁ and bPEG₂-T₂-X₂-(Y₂)n₂-O-P(=O)(O⁻)-O-(CH₂)L₂ connected to -(CH₂)q-O-P(=O)(O⁻)-O-(W)m-Z]

wherein
m is 0 or 1,
$n_1$ and $n_2$ are the same or different and each is 0 or 1,
$L_1$ and $L_2$ are the same or different and each is an integer of 1-6,
q is an integer of 0-6,
$T_1$ and $T_2$ are the same or different and each is —C(O)—NH—, or

[structure showing succinimide-thioether group]

(* shows the bonding position of $bPEG_1$ or $bPEG_2$, ** shows the bonding position of $X_1$ or $X_2$),
$X_1$ and $X_2$ are the same or different and each is —(CH₂)₃—, —(CH₂)₆—, —(CH₂)₂OC(=O)NH(CH₂)₆—, —(CH₂)₂NHC(=O)O(CH₂)₆—, or —(CH₂)₂—[O(CH₂)₂]g— (wherein g is an integer of 2-5),
$Y_1$ and $Y_2$ are the same or different and each is —OP(=O)(O⁻)O(CH₂)₃—, —OP(=O)(O⁻)O(CH₂)₆—, —OP(=O)(O⁻)O(CH₂)₁₂—, or —OP(=O)(O⁻)—[O(CH₂)₂]j— (wherein j is an integer of 2-6), W is —(CH₂)₃OP(=O)(O⁻)O—, —(CH₂)₆OP(=O)(O⁻)O—, —(CH₂)₁₂OP(=O)(O⁻)O—, or —[O(CH₂)₂]j—OP(=O)(O⁻)— (wherein j is an integer of 2-6),
$bPEG_1$ and $bPEG_2$ are the same or different and each is 10-80 kDa polyethylene glycol having a branched chain,
Z is an aptamer comprising a sequence represented by the following formula (Ia):

(SEQ ID NO: 105)
g(M)g(M)g(M)u(M)a'(M)g'(X₁)c(M)c(M)g'g(M)a'(X₄)
g(X₅)g(M)a(M)g(X₅)u'(F)c(X₇)a'(X₂)g(X₆)u'(F)r(X₃)
a'(X₃)u(M)c(M)g(M)g(M)u'(X₇)a'(M)c'(M)c'(M)c'(M)

or the following formula (Ib):

(SEQ ID NO: 106)
g(M)g(M)u(M)a'(M)g'(X₁)c(M)c(M)g'g(M)a'(X₄)g(X₅)g
(M)a(M)g(X₅)u'(F)c(X₇)a'(X₂)g(X₆)u'(F)r(X₃)a'(X₃)
u(M)c(M)g(M)g(M)u'(X₇)a'(M)c'(M)c'(M)

or the following formula (Ic):

(SEQ ID NO: 107)
g(M)u(M)a'(M)g'(X₁)c(M)c(M)g'g(M)a'(X₄)g(X₅)g(M)a
(M)g(X₅)u'(F)c(X₇)a'(X₂)g(X₆)u'(F)r(X₃)a'(X₃)u(M)
c(M)g(M)g(M)u'(X₇)a'(M)c'(M)

or the following formula (Id):

(SEQ ID NO: 108)
u(M)a'(M)g'(X₁)c(M)c(M)g'g(M)a'(X₄)g(X₅)g(M)a(M)
g(X₅)u'(F)c(X₇)a'(X₂)g(X₆)u'(F)r(X₃)a'(X₃)u(M)c(M)
g(M)g(M)u'(X₇)a'(M)

{in the above-mentioned formulas (Ia), (Ib), (Ic) and (Id),
a, g, c and u are each a ribonucleotide wherein the base is adenine, guanine, cytosine and uracil, respectively,
r is a ribonucleotide wherein the base is adenine or guanine,
a', g' and c' are each a ribonucleotide or deoxyribonucleotide wherein the base is adenine, guanine and cytosine, respectively,
u' is a ribonucleotide wherein the base is uracil, a deoxyribonucleotide wherein the base is uracil or a deoxyribonucleotide wherein the base is thymine,
parentheses in nucleotide indicate modification of the nucleotide,
(M) indicates that, when the nucleotide is a ribonucleotide, a hydroxyl group at the 2'-position of ribose therein is substituted by an O-methyl group,
(F) indicates that, when the nucleotide is a ribonucleotide, a hydroxyl group at the 2'-position of ribose therein is substituted by a fluorine atom,
($X_1$) indicates that nucleotide is unmodified or phosphorothioated, or when the nucleotide is a ribonucleotide, a hydroxyl group at the 2'-position of ribose therein is substituted by a fluorine atom,
($X_2$) indicates that nucleotide is unmodified, or when the nucleotide is a ribonucleotide, a hydroxyl group at the 2'-position of ribose therein is substituted by a fluorine atom,
($X_3$) indicates that nucleotide is unmodified, or when the nucleotide is a ribonucleotide, a hydroxyl group at the 2'-position of ribose therein is substituted by an O-methyl group,
($X_4$) indicates that nucleotide is unmodified, or when the nucleotide is a ribonucleotide, a hydroxyl group at the 2'-position of ribose therein is substituted by a fluorine atom or an O-methyl group,
($X_5$) indicates that nucleotide is unmodified or phosphorothioated,
($X_6$) indicates that nucleotide is unmodified or phosphorothioated, or when the nucleotide is a ribonucleotide, a hydroxyl group at the 2'-position of ribose therein is substituted by an O-methyl group, and
($X_7$) indicates that when nucleotide is a ribonucleotide, a hydroxyl group at the 2'-position of ribose therein is substituted by a fluorine atom or an O-methyl group,}or the following formula (IIa):

(SEQ ID NO: 109)
g(x₁)g(x₁)g(x₁)u(F)ag(S)c(F)c(F)g'(S)g(x₂)aggagu
(F)c(F)agu(F)aau(F)c(F)ggu(F)ac'(x₃)c'(x₃)c'(x₃)

or the following formula (IIb):

(SEQ ID NO: 110)
g(x₁)g(x₁)u(F)ag(S)c(F)c(F)g'(S)g(x₂)aggagu(F)c
(F)agu(F)aau(F)c(F)ggu(F)ac'(x₃)c'(x₃)

or the following formula (IIc):

(SEQ ID NO: 111)
g(x₁)u(F)ag(S)c(F)c(F)g'(S)g(x₂)aggagu(F)c(F)agu
(F)aau(F)c(F)ggu(F)ac'(x₃)

{in the above-mentioned formulas (IIa), (IIb) and (IIc),
(S) indicates that, when nucleotide is a ribonucleotide, it is phosphorothioated,
($x_1$) indicates that nucleotide is Locked Nucleic Acid (LNA)-modified, or when the nucleotide is a ribonucleotide, a hydroxyl group at the 2'-position of ribose therein is substituted by an O-methyl group,
($x_2$) indicates that nucleotide is unmodified, or when the nucleotide is a ribonucleotide, a hydroxyl group at the 2'-position of ribose therein is substituted by an O-methyl group,
($x_3$) indicates that nucleotide is unmodified, or LNA-modified, and
other symbols are as defined above},
or a pharmaceutically acceptable salt, solvate or hydrate thereof.

2. The compound according to claim 1, wherein
m is 0,
m and $n_2$ are each 0 or 1,
$L_1$ and $L_2$ are each 1,
q is 0,
$T_1$ and $T_2$ are the same or different and each is —C(O)—NH—, or,

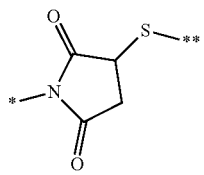

(* shows the bonding position of $bPEG_1$ or $bPEG_2$, ** shows the bonding position of $X_1$ or $X_2$),
$X_1$ and $X_2$ are the same and —(CH₂)₆—, —(CH₂)₂OC(=O)NH(CH₂)₆—, —(CH₂)₂NHC(=O)O(CH₂)₆—, or —(CH₂)₂—[O(CH₂)₂]₃—, and
$Y_1$ and $Y_2$ are each —OP(=O)(O⁻)O(CH₂)₃—, —OP(=O)(O⁻)O(CH₂)₆—, —OP(=O)(O⁻)O(CH₂)₁₂—, or —OP(=O)(O⁻)—[O(CH₂)₂]₃—,
or a pharmaceutically acceptable salt, solvate or hydrate thereof.

3. The compound according to claim 1, wherein
m is 0,
$n_1$ and $n_2$ are each 0 or 1,
$L_1$ and $L_2$ are each 1,
q is 0,
$T_1$ and $T_2$ are each —C(O)—NH—,
$X_1$ and $X_2$ are each —(CH₂)₆—, —(CH₂)₂OC(=O)NH(CH₂)₆—, —(CH₂)₂NHC(=O)O(CH₂)₆—, or —(CH₂)₂—[O(CH₂)₂]₃—, and
$Y_1$ and $Y_2$ are each —OP(=O)(O⁻)O(CH₂)₃—, —OP(=O)(O⁻)O(CH₂)₆—, —OP(=O)(O⁻)O(CH₂)₁₂—, or —OP(=O)(O⁻)—[O(CH₂)₂]₃—,
or a pharmaceutically acceptable salt, solvate or hydrate thereof.

4. The compound according to claim 1, wherein
m is 0,
m and $n_2$ are each 1,
$L_1$ and $L_2$ are each 1,
q is 0,
$T_1$ and $T_2$ are each —C(O)—NH—,
$X_1$ and $X_2$ are each —(CH₂)₆—, or —(CH₂)₂OC(=O)NH(CH₂)₆—, and
$Y_1$ and $Y_2$ are each —OP(=O)(O⁻)—[O(CH₂)₂]₃—,
or a pharmaceutically acceptable salt, solvate or hydrate thereof.

5. The compound according to claim 1, wherein
m is 0,
$n_1$ and $n_2$ are each 0,
$L_1$ and $L_2$ are each 1,
q is 0, and
$T_1$ and $T_2$ are each —C(O)—NH—,
$X_1$ and $X_2$ are each —(CH₂)₆—, —(CH₂)₂OC(=O)NH(CH₂)₆—, or —(CH₂)₂—[O(CH₂)₂]₃—,
or a pharmaceutically acceptable salt, solvate or hydrate thereof.

6. The compound according to claim 1, wherein Z is an aptamer comprising a sequence shown in any of SEQ ID NOs: 3-93, or a pharmaceutically acceptable salt, solvate or hydrate thereof.

7. The compound according to claim 1, wherein $bPEG_1$ and $bPEG_2$ are each 15-45 kDa polyethylene glycol having a branched chain, and
Z is an aptamer comprising a sequence shown in any of SEQ ID NOs: 3-93, or a pharmaceutically acceptable salt, solvate or hydrate thereof.

8. The compound according to claim 1, wherein $bPEG_1$ and $bPEG_2$ are each 35-45 kDa polyethylene glycol having a branched chain, or a pharmaceutically acceptable salt, solvate or hydrate thereof.

9. A medicament comprising the compound according to claim 1, or a pharmaceutically acceptable salt, solvate or hydrate thereof.

10. The compound according to claim 1, wherein Z is an aptamer comprising a sequence shown in any of SEQ ID NOs: 1-2, or a pharmaceutically acceptable salt, solvate or hydrate thereof.

11. The compound according to claim 1, wherein Z is an aptamer comprising a sequence shown in any of SEQ ID NOs: 94, 97, 100, and 103, or a pharmaceutically acceptable salt, solvate or hydrate thereof.

12. The compound according to claim 1, wherein Z is an aptamer comprising a sequence shown in any of SEQ ID NOs: 95, 98, 101, and 104, or a pharmaceutically acceptable salt, solvate or hydrate thereof.

13. The compound according to claim 1, wherein Z is an aptamer comprising a sequence shown in any of SEQ ID NOs: 96, 99, and 102, or a pharmaceutically acceptable salt, solvate or hydrate thereof.

* * * * *

UNITED STATES PATENT AND TRADEMARK OFFICE
CERTIFICATE OF CORRECTION

PATENT NO. : 11,013,756 B2  
APPLICATION NO. : 15/780464  
DATED : May 25, 2021  
INVENTOR(S) : Kazuhiko Haruta et al.

Page 1 of 1

It is certified that error appears in the above-identified patent and that said Letters Patent is hereby corrected as shown below:

In the Claims

Column 355, Line 16 Claim 1, Line 5 change "m" to -- $n_1$ --;

Column 357, Line 38 Claim 2, Line 3 change "m" to -- $n_1$ --; and

Column 358, Line 13 Claim 4, Line 3 change "m" to -- $n_1$ --.

Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*